US008828926B2

(12) United States Patent
Bastos et al.

(10) Patent No.: US 8,828,926 B2
(45) Date of Patent: Sep. 9, 2014

(54) USES OF NATRIURETIC PEPTIDE CONSTRUCTS

(71) Applicant: Palatin Technologies, Inc., Cranbury, NJ (US)

(72) Inventors: Margarita Bastos, Plainsboro, NJ (US); Jennifer Lata, New Hope, PA (US); Jeffrey D. Edelson, Berwyn, PA (US)

(73) Assignee: Palatin Technologies, Inc., Cranbury, NJ (US)

( * ) Notice: Subject to any disclaimer, the term of this patent is extended or adjusted under 35 U.S.C. 154(b) by 0 days.

(21) Appl. No.: 13/653,508

(22) Filed: Oct. 17, 2012

(65) Prior Publication Data

US 2013/0045928 A1 Feb. 21, 2013
US 2013/0274207 A9 Oct. 17, 2013

Related U.S. Application Data

(63) Continuation of application No. PCT/US2011/033366, filed on Apr. 21, 2011.

(60) Provisional application No. 61/326,302, filed on Apr. 21, 2010.

(51) Int. Cl.
| | |
|---|---|
| A61K 38/12 | (2006.01) |
| A61K 38/10 | (2006.01) |
| C07K 7/08 | (2006.01) |
| C07K 7/64 | (2006.01) |
| A61P 11/06 | (2006.01) |
| A61P 11/00 | (2006.01) |
| A61K 38/22 | (2006.01) |
| C07K 14/58 | (2006.01) |

(52) U.S. Cl.
CPC ............... A61K 38/12 (2013.01); *C07K 14/582* (2013.01); A61K 38/2242 (2013.01)
USPC .............................. 514/1.7; 530/317; 530/327

(58) Field of Classification Search
CPC . A61K 38/12; A61K 38/2242; C07K 14/582; A61N 5/1027; A61N 1/0587; A61N 2001/0585; A61N 2005/0612; A61N 2005/063; A61B 17/3468; A61B 17/3478; A61B 18/082; A61B 18/1477; A61B 18/1492; A61B 2017/00247; A61B 2018/00404; A61B 2018/00577; A61B 2018/1495; A61M 25/0069; A61M 25/065; A61M 2025/0042
See application file for complete search history.

(56) References Cited

U.S. PATENT DOCUMENTS 5,169,932 A 12/1992 Hoeger et al.
7,622,440 B2 * 11/2009 Sharma et al. .................. 514/1.1

2007/0265206 A1 * 11/2007 Sharma et al. .................. 514/15
2009/0069224 A1 3/2009 Sharma et al.
2010/0075895 A1 3/2010 Sharma et al.

FOREIGN PATENT DOCUMENTS

WO 2009033807 3/2009

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Definition of moiety, from http://dictionary.reference.com/browse/moieties, pp. 1-3, accessed Aug. 26, 2010.*
List of Respiratory diseases, from http://doctors-hospitals-medical-cape-town-south-africa.blaauwberg.net/details.php?id=831, pp. 1-3, accessed Oct. 22, 2013.*
Alphabetical List of Lung Disease, from http://www.lung.org/lung-disease/list.html?print=t, pp. 1-4, accessed Oct. 22, 2013.*
Communication—International Search Report—PCT/US2011/33366 (WO 2011/133735 A3); Published Oct. 31, 2011.
Akerman, M. J., et al., "Bronchodilator Effect of Infused B-Type Natriuretic Peptide in Asthma", Chest, vol. 130; Issue 1, (2006), 66-72.

(Continued)

*Primary Examiner* — Julie Ha
*Assistant Examiner* — Li Ni Komatsu
(74) *Attorney, Agent, or Firm* — Stephen A. Slusher

(57) ABSTRACT

Use of constructs which bind to one or more natriuretic peptide receptors and include a plurality of amino acid residues and at least one amino acid surrogate of formula I:

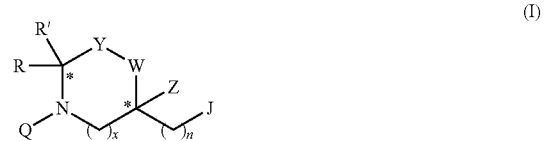

(I)

where R, R', Q, Y, W, Z, J, x and n are as defined in the specification, and optionally at least one prosthetic group, for the prophylaxis or treatment of airway diseases, including but not limited to inflammation-related airway diseases, acute asthma or chronic obstructive pulmonary disease, methods of prophylaxis and treatment of airway diseases and pharmaceutical compositions and formulations for the prophylaxis or treatment of airway diseases.

10 Claims, 4 Drawing Sheets

(56) References Cited

OTHER PUBLICATIONS

Angus, R. M., et al., "Effect of inhaled atrial natriuretic peptide and a neutral endopeptidase inhibitor on histamine induced bronchoconstriction", Am. J. Respir. Crit. Care Med., vol. 151, Issue 6, (1995), 2003-2005.

Fluge, T., et al., "Urodilatin (Ularitide, INN): a potent bronchodilator in asthmatic subjects", Eur. J. Clin. Invest., vol. 25, Issue 10, (1995), 728-736.

Hamad, A. M., et al., "Guanylyl cyclases, nitric oxide, natriuretic peptides, and airway smooth muscle function", Am. J. Physiol Lung Cell Mol. Physiol., vol. 285, Issue 5, (2003), 973-983.

Hruby, V. J., et al., "Emerging approaches in the molecular design of receptor-selective peptide ligands: conformational, topographical and dynamic considerations", Biochem J., vol. 268, Review Article, (1990), 249-262.

Leuchte, H. H., et al., "Preserved pulmonary vasodilative properties of aerosolized brain natriuretic peptide", Pulmonary Pharmacology & Therapeutics, vol. 22, Issue 6, (2009), 548-533.

Matera, M. G., et al., "Relaxant effect of brain natriuretic peptide in non sensitized and passively sensitized isolated human bronchi", Pulmonary Pharmacology & Therapeutics, vol. 2, Issue 6, (2009), 478-482.

* cited by examiner

SEQUENCE LISTING

```
<160> NUMBER OF SEQ ID NOS: 3

<210> SEQ ID NO 1
<211> LENGTH: 15
<212> TYPE: PRT
<213> ORGANISM: Artificial Sequence
<220> FEATURE:
<223> OTHER INFORMATION: Synthetic deriviative of human (homo sapiens)
      atrial natriuretic peptide
<220> FEATURE:
<221> NAME/KEY: DISULFID
<222> LOCATION: (2)..(13)
<220> FEATURE:
<221> NAME/KEY: MOD_RES
<222> LOCATION: (15)..(15)
```

```
<223> OTHER INFORMATION: AMIDATION

<400> SEQUENCE: 1

Met Cys His Phe Gly Gly Arg Met Asp Arg Ile Ser Cys Tyr Arg
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic deriviative of human (homo sapiens)
      atrial natriuretic peptide
<220> FEATURE:
<221> NAME/KEY: MISC_FEATURE
<222> LOCATION: (2)..(2)
<223> OTHER INFORMATION: Xaa is any amino acid forming a cyclic peptide
      with the amino acid in position 13
<220> FEATURE:
<221> NAME/KEY: MISC_FEATURE
<222> LOCATION: (13)..(13)
<223> OTHER INFORMATION: Xaa is any amino acid forming a cyclic peptide
      with the amino acid in position 2
<220> FEATURE:
<221> NAME/KEY: MOD_RES
<222> LOCATION: (15)..(15)
<223> OTHER INFORMATION: AMIDATION

<400> SEQUENCE: 2

Met Xaa His Phe Gly Gly Arg Met Asp Arg Ile Ser Xaa Tyr Arg
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: Synthetic deriviative of human (homo sapiens)
      atrial natriuretic peptide of the invention with N-terminal
      heptanoyl and C-terminal non-amino acid surrogate substituted
      keto-piperazine with guanidino group
<220> FEATURE:
<221> NAME/KEY: DISULFID
<222> LOCATION: (1)..(12)
<220> FEATURE:
<221> NAME/KEY: MISC_FEATURE
<222> LOCATION: (4)..(4)
<223> OTHER INFORMATION: D-Ala
<220> FEATURE:
<221> NAME/KEY: MISC_FEATURE
<222> LOCATION: (7)..(7)
<223> OTHER INFORMATION: D-Nle

<400> SEQUENCE: 3

Cys His Phe Xaa Gly Arg Xaa Asp Arg Ile Ser Cys Tyr
1               5                   10
```

USES OF NATRIURETIC PEPTIDE CONSTRUCTS

CROSS-REFERENCE TO RELATED APPLICATIONS

This application is a continuation of International Application No. PCT/US2011/033366, published as International Publication No. WO 2011/133735 A2, entitled "Uses of Natriuretic Peptide Constructs", filed on Apr. 21, 2011, which in turn claimed priority to and the benefit of the filing of U.S. Provisional Patent Application Ser. No. 61/326,302 entitled "Uses of Natriuretic Peptide Constructs", filed Apr. 21, 2010. The specification and claims of each of the foregoing applications are incorporated herein by reference.

BACKGROUND OF THE INVENTION

1. Field of the Invention (Technical Field)

The present invention relates to uses of natriuretic peptide constructs which include a plurality of amino acid residues and one or more ring-constrained amino acid surrogates and optionally one or more prosthetic groups, for the prophylaxis or treatment of airway diseases, including but not limited to acute asthma and COPD.

2. Background Art

The natriuretic peptide system has been extensively explored since the identification of the human atrial natriuretic peptide (ANP) sequence and gene structure in 1984. ANP is sometimes also called "ANF", or atrial natriuretic factor. ANP is part of the natriuretic peptide system, which in humans involves an ANP gene, which through differences in post-translational processing results in both ANP and urodilatin, a gene which produces BNP, or brain natriuretic peptide, and a gene which produces CNP, or c-type natriuretic peptide. ANP, urodilatin, BNP and CNP are each ring structures, with a 17 amino acid loop formed by a cysteine-cysteine disulfide linkage. ANP, urodilatin, BNP and CNP are closely related, differing by some five or six amino acids within the ring, though the N- and C-terminal tails are substantially different.

There are three known natriuretic peptide receptors called natriuretic peptide receptors A, B and C (NPRA, NPRB and NPRC). NPRA and NPRB are linked to guanylyl cyclases, while NPRC is a G-protein linked clearance receptor. ANP, BNP and CNP are the primary endogenous mammalian natriuretic peptides identified to date. However, there are a number of non-mammalian natriuretic peptides that have been identified and may have therapeutic application in mammals. Human ANP is also referred to as wild-type human ANP, hANP, ANP(1-28) and ANP(99-126) (the later referring to the relevant sequence within proANP(1-126), which is normally cleaved at $Arg^{98}$-$Ser^{99}$ in the C-terminal region during secretion).

Human ANP and BNP, including human BNP made by recombinant means, have been described as potentially having application in the treatment of asthma and related diseases, presumably through a mechanism related to increased guanylyl cyclase production, which in turn catalyzes the conversion of guanosine triphosphate (GTP) to 3',5'-cyclic guanosine monophosphate (cGMP), resulting in increased cGMP levels. See, for example, Leuchte, H. H.; Michalek, J. et al., "Preserved pulmonary vasodilative properties of aerosolized brain natriuretic peptide," *Pulmonary Pharmacology & Therapeutics* 22:548-533 (2009); Matera, M. G.; Calzetta, L. et al., "Relaxant effects of brain natriuretic peptide in nonsensitized and passively sensitized isolated human bronchi," *Pulmonary Pharmacology & Therapeutics* 22:478-482 (2009); and Hamad, A. M.; Clayton, A. et al., "Guanylyl cyclases, nitric oxide, natriuretic peptides, and airway smooth muscle function." *Am. J. Physiol. Lung Cell Mol. Physiol.* 285:973-983 (2003).

There are reports in the literature of human studies involving administration of human ANP and human BNP, such as by intravenous administration of BNP (Akerman, M. J.; Yaegashi, M. et al., "Bronchodilator Effect of Infused B-Type Natriuretic Peptide in Asthma." *Chest* 130:66-72 (2006)), intravenous administration of ANP (Flüge, T.; Fabel, H. et al., "Urodilatin (Ularitide, INN): a potent bronchodilator in asthmatic subjects." *Eur. J. Clin. Invest.* 25:728-36 (1995)), and inhaled ANP (Angus, R. M.; Millar, E. A. et al., "Effect of inhaled atrial natriuretic peptide and a neutral endopeptidase inhibitor on histamine induced bronchoconstriction." *Am. J. Respir. Crit. Care Med.* 151:2003-2005 (1995).

There are, however, no reports of studies for treatment of asthma or related indications with compounds with natriuretic peptide functions, but which have increased resistence to enzymatic degradation, increased circulation half life, increased bioavailability, increased efficacy, prolonged duration of effect and combinations of the foregoing compared to human ANP or human BNP. While some reports have utilized an inhibitor, such as a neutral endopeptidase inhibitor, in combination with human ANP (see R. Angus et al., cited above), no reports have utilized compounds with the desired pharmacological properties.

Notwithstanding the large number of compounds that have been developed, none have been commercialized for the prophylaxis or treatment of airway diseases, including but not limited to acute asthma and COPD, and no natriuretic peptide compositions are reported to be in in active clinical development for the prophylaxis or treatment of airway diseases, including but not limited to acute asthma and COPD. There is a substantial need for products with improved characteristics, including improved potency, half-life, modes of administration, bioavailability or prolonged duration of effect, which products are effective for one or more airway disease therapeutic indications.

BRIEF SUMMARY OF THE INVENTION

In one aspect the invention provides a method of prophylaxis or treatment of airway diseases, including but not limited to acute asthma and COPD, by administration of a pharmaceutically effective amount of a construct which binds to a receptor for a natriuretic peptide, including but not limited to a receptor for ANP, BNP, CNP, sCP, DNP, TNP-a, TNP-b or TNP-c, wherein such construct includes a plurality of amino acid residues and at least one amino acid surrogate of the general formula I:

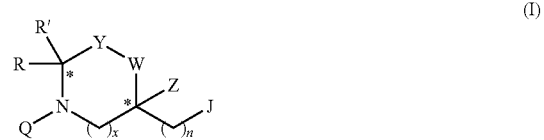

(I)

where R and R' are each independently H or a natural or unnatural amino acid side chain moiety or derivative of an amino acid side chain moiety; x is 1 or 2; Y is $CH_2$ or C=O; W is $CH_2$, NH or NR'''; Z is H or $CH_3$; n is 0, 1 or 2; J is —C(=O)— unless the surrogate is at the C-terminus position of the construct, in which case J is —H, —OH, —C(=O)—OH, —C(=O)—$NH_2$ or a C-terminus capping group; Q is a bond unless the surrogate is at the N-terminus position of the construct, in which case Q is —H or an amine capping group; R''' is an acyl, a $C_1$ to $C_{17}$ linear or branched alkyl chain, a $C_2$ to $C_{19}$ linear or branched alkyl acyl chain, a $C_1$ to $C_{17}$ linear or branched omega amino aliphatic, or a $C_1$ to $C_{17}$ linear or branched omega amino aliphatic acyl; optionally at least one prosthetic group covalently bonded to a reactive group in a side chain of at least one of the amino acid residues, to an amine capping group where the surrogate is at the N-terminus position of the construct, or to a C-terminus capping group where the surrogate is at the C-terminus position of the construct; and the carbon atoms marked with an asterisk can have any stereochemical configuration. The plurality of amino acid residues may include any amino acid residue selected from the group consisting of natural or unnatural α-amino acids, β-amino acids, α, α-disubstituted amino acids and N-substituted amino acids, including all (R) or (S) configurations of any of the foregoing.

The construct may be a cyclic construct, cyclized by a bond between side chains of two amino acid residues, between an amino acid residue side chain and an R or R' group of an amino acid surrogate, between R or R' groups of two amino acid surrogates, between a terminal group of the construct and an amino acid residue side chain, or between a terminal group of the construct and an R or R' group of an amino acid surrogate. Preferable the two amino acid residues forming a bond between the side chains thereof are separated by between about eight and ten amino acid residues and optionally zero, one or two amino acid surrogates.

The prosthetic group(s) may include polymeric groups comprising repeat units including one or more carbon and hydrogen atoms, and optionally other atoms, including oxygen. Such polymeric groups are preferably water-soluble polymers, and are preferably poly(alkylene oxide), poly(vinyl pyrrolidone), poly(vinyl alcohol), polyoxazoline or poly(acryloylmorpholine). A preferred poly(alkylene oxide) is poly(ethylene glycol) (PEG), optionally derivatized with a linking group.

In one aspect, J is a C-terminus capping group selected from
—$(CH_2)_m$—OH,
—C(=O)—$(CH_2)_m$—N($v_1$)($v_2$),
—C(=O)—O—$(CH_2)_m$—$CH_3$,
—O—$(CH_2)_m$—$CH_3$,
—O—$(CH_2)_m$—N($v_1$)($v_2$),
—O—$(CH_2)_m$—OH,
—C(=O)—NH—$(CH_2)_m$—S($v_1$),
—C(=O)—NH—$(CH_2)_m$—$CH_3$,
—C(=O)—NH—$(CH_2)_m$—N($v_1$)($v_2$),
C(=O)—N—(($CH_2)_m$—N($v_1$)($v_2$))$_2$,
—C(=O)—NH—CH(—C(=O)—OH)—$(CH_2)_m$—N($v_1$)($v_2$),
—C(=O)—NH—$(CH_2)_m$—NH—C(=O)—CH(N($v_1$)($v_2$))(($CH_2)_m$—N($v_1$)($v_2$)), or
—C(=O)—NH—CH(—C(=O)—N($v_1$)($v_2$))—$(CH_2)_m$—N($v_1$)($v_2$);
including all (R) or (S) configurations of the foregoing, where $v_1$ and $v_2$ are each independently H or a $C_1$ to $C_{17}$ linear or branched alkyl chain and m is in each instance independently 0 to 17.

In another aspect where the amino acid surrogate is at the C-terminus position of the construct, J is a C-terminus capping group consisting of an omega amino aliphatic, terminal aryl or aralkyl group or any single natural or unnatural α-amino acid, β-amino acid, α, α-disubstituted amino acid or N-substituted amino acid, including all (R) or (S) configurations of an α, α-disubstituted amino acid where the substituents are different, optionally in combination with a C-terminus capping group as defined above.

In another aspect, Q is an amine capping group selected from
—$(CH_2)_m$—N($v_3$)($v_4$),
$(CH_2)_m$—$CH_3$,
—$(CH_2)_m$—O($v_3$),
—$(CH_2)_m$—C(=O)—($v_3$),
—$(CH_2)_m$—C(=O)—O—($v_3$),
—$(CH_2)_m$—S($v_3$),
—C(=O)—$(CH_2)_m$—$CH_3$,
—C(=O)—$(CH_2)_m$—N($v_3$)($v_4$),
—C(=O)—$(CH_2)_m$—C(=O)—($v_3$),
—C(=O)—$(CH_2)_m$—O($v_3$), or
—C(=O)—$(CH_2)_m$—S($v_3$);
where $v_3$ and $v_4$ are each independently H, a $C_1$ to $C_{17}$ linear or branched alkyl chain or a $C_2$ to $C_{19}$ linear or branched alkyl acyl chain, on the proviso that if one of $v_3$ or $v_4$ is an alkyl acyl chain, then the other of $v_3$ or $v_4$ is H, and m is 0 to 17.

In a related aspect, an amino acid surrogate of formula I is at the C-terminus position of the construct, and at least one of R and R' is a natural or unnatural amino acid side chain moiety or derivative of an amino acid side chain moiety with a heteroatom group comprising at least one nitrogen atom, and the remaining one of R and R' is H or a natural or unnatural amino acid side chain moiety or derivative of an amino acid side chain moiety.

In a related embodiment, the invention provides a construct which binds to a receptor for a natriuretic peptide, including but not limited to a receptor for ANP, BNP, CNP, sCP, DNP, TNP-a, TNP-b or TNP-c, wherein such construct includes a plurality of amino acid residues and at least one amino acid surrogate located at any position other than the C-terminus position or N-terminus position and covalently bonded by two peptide bonds, and of formula II:

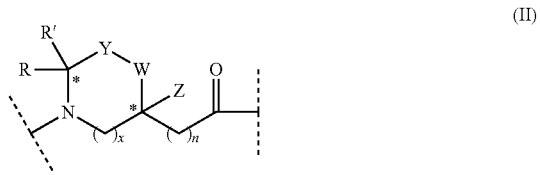

where R and R' are each independently H or a natural or unnatural amino acid side chain moiety or derivative of an amino acid side chain moiety; x is 1 or 2; Y is $CH_2$ or C=O; W is $CH_2$, NH or NR'''; Z is H or $CH_3$; R''' is an acyl, a $C_1$ to $C_{17}$ linear or branched alkyl chain, a $C_2$ to $C_{19}$ linear or branched alkyl acyl chain, a $C_1$ to $C_{17}$ linear or branched omega amino aliphatic, or a $C_1$ to $C_{17}$ linear or branched omega amino aliphatic acyl; n is 0, 1 or 2; the carbon atoms marked with an asterisk can have any stereochemical configuration; and the broken lines indicate the bond forming a peptide bond.

Where the surrogate of formula I is at the C-terminus of the construct, it is covalently bonded thereto by a single peptide bond, such that the surrogate has the formula:

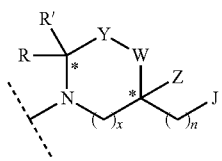

where the broken line indicates the bond forming a peptide bond. Where the surrogate is at the N-terminus of the construct it is preferably of formula I, and is covalently bonded thereto by a single bond peptide bond, such that the surrogate has the formula:

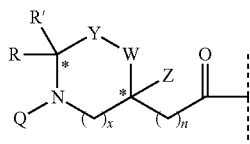

where the broken line indicates the bond forming a peptide bond. However, where the surrogate is at other than at the N-terminus or C-terminus of the construct, it is preferably of formula II and is covalently bonded thereto by two peptide bonds.

In different embodiments of the invention, one amino acid surrogate may be employed in a construct of the invention, two amino acid surrogates may be employed in a construct of the invention, or more than two amino acid surrogates may be employed in a construct of the invention.

A primary object of the present invention is to provide methods for the prophylaxis or treatment of airway diseases, including but not limited to acute asthma and COPD, utilizing natriuretic receptor-specific constructs.

Another object of the present invention is to provide methods for the prophylaxis or treatment of airway diseases, including but not limited to acute asthma and COPD, utilizing a natriuretic receptor-specific construct wherein the construct exhibits, upon administration to a mammal, one or more advantages relative to the corresponding amino acid sequence not comprising an amino acid surrogate, the advantages selected from the group consisting of increased resistance to enzymatic degradation, increased circulation half life, increased bioavailability, increased efficacy, prolonged duration of effect and combinations of the foregoing.

Another object of the present invention is to provide methods for the prophylaxis or treatment of airway diseases, including but not limited to acute asthma and COPD, utilizing a natriuretic receptor-specific construct wherein the construct has at least 10% of the maximal cGMP stimulating activity as the same concentration of the corresponding amino acid sequence not comprising an amino acid surrogate.

Another object of the present invention is to provide methods for the prophylaxis or treatment of airway diseases, including but not limited to acute asthma and COPD, utilizing a natriuretic receptor-specific construct wherein the construct has at least 50% of the maximal cGMP stimulating activity as the same concentration of the corresponding amino acid sequence not comprising an amino acid surrogate.

Another object of the present invention is to provide methods for the prophylaxis or treatment of airway diseases, including but not limited to acute asthma and COPD, utilizing a natriuretic receptor-specific construct wherein the construct has at least 100% of the maximal cGMP stimulating activity as the same concentration of the corresponding amino acid sequence not comprising an amino acid surrogate.

Another object of the present invention is to provide methods for the prophylaxis or treatment of airway diseases, including but not limited to acute asthma and COPD, utilizing a natriuretic receptor-specific construct wherein the construct has more than 100% of the maximal cGMP stimulating activity as the same concentration of the corresponding amino acid sequence not comprising an amino acid surrogate.

Another object of the present invention is to provide methods for the prophylaxis or treatment of airway diseases, including but not limited to acute asthma and COPD, utilizing a natriuretic receptor-specific construct wherein the construct has an equilibrium receptor binding affinity, determined by the Ki (nM) value, no greater than two log orders higher than the Ki (nM) value of the corresponding amino acid sequence not comprising an amino acid surrogate.

Another object of the present invention is to provide methods for the prophylaxis or treatment of airway diseases, including but not limited to acute asthma and COPD, utilizing a natriuretic receptor-specific construct wherein the construct has an equilibrium receptor binding affinity, determined by the Ki (nM) value, no greater than three times higher than the Ki (nM) value of the corresponding amino acid sequence not comprising an amino acid surrogate.

Another object of the present invention is to provide methods for the prophylaxis or treatment of airway diseases, including but not limited to acute asthma and COPD, utilizing a natriuretic receptor-specific construct wherein the construct has an equilibrium receptor binding affinity, determined by the Ki (nM) value, equal to or less than the Ki (nM) value of the corresponding amino acid sequence not comprising an amino acid surrogate.

Another object of the present invention is to provide methods for the prophylaxis or treatment of airway diseases, including but not limited to acute asthma and COPD, utilizing a natriuretic receptor-specific construct wherein the construct has an equilibrium receptor binding affinity, determined by the Ki (nM) value, less than the Ki (nM) value of the corresponding amino acid sequence not comprising an amino acid surrogate.

Another object of the present invention is to provide methods for the prophylaxis or treatment of airway diseases, including but not limited to acute asthma and COPD, utilizing a natriuretic receptor-specific construct wherein the construct has a receptor binding affinity with respect to a natriuretic peptide receptor greater than the receptor binding affinity of the corresponding amino acid sequence not comprising an amino acid surrogate.

Another object of the present invention is to provide methods for the prophylaxis or treatment of airway diseases, including but not limited to acute asthma and COPD, utilizing a natriuretic receptor-specific construct wherein the corresponding amino acid sequence not comprising an amino acid surrogate has at least about 60% homology with the sequence H-Met-cyclo(Cys-His-Phe-Gly-Gly-Arg-Met-Asp-Arg-Ile-Ser-Cys)-Tyr-Arg-NH$_2$ (SEQ ID NO:1).

Another object of the present invention is to provide methods for the prophylaxis or treatment of airway diseases, including but not limited to acute asthma and COPD, utilizing a natriuretic receptor-specific construct wherein the corresponding amino acid sequence not comprising an amino acid surrogate has at least about 80% homology with the sequence H-Met-cyclo(Cys-His-Phe-Gly-Gly-Arg-Met-Asp-Arg-Ile-Ser-Cys)-Tyr-Arg-NH$_2$ (SEQ ID NO:1).

Another object of the present invention is to provide methods for the prophylaxis or treatment of airway diseases, including but not limited to acute asthma and COPD, utilizing a natriuretic receptor-specific construct wherein the corresponding amino acid sequence not comprising an amino acid surrogate has at least about 60% homology with the sequence H-Met-cyclo(Xaa-His-Phe-Gly-Gly-Arg-Met-Asp-Arg-Ile-Ser-Xaa)-Tyr-Arg-NH$_2$ (SEQ ID NO:2), where Xaa are each independently any amino acid residue which together form a cyclic peptide.

Another object of the present invention is to provide methods for the prophylaxis or treatment of airway diseases, including but not limited to acute asthma and COPD, utilizing a natriuretic receptor-specific construct wherein the corresponding amino acid sequence not comprising an amino acid surrogate has at least about 80% homology with the sequence H-Met-cyclo(Xaa-His-Phe-Gly-Gly-Arg-Met-Asp-Arg-Ile-Ser-Xaa)-Tyr-Arg-NH$_2$ (SEQ ID NO:2), where Xaa are each independently any amino acid residue which together form a cyclic peptide.

Another object of the present invention is to provide natriuretic receptor-specific constructs which may be administered to patients with airway disease, including but not limited to acute asthma or COPD.

Another object of the present invention is to provide natriuretic receptor-specific constructs which may be administered for prophylaxis or therapy of airway diseases by inhalation.

Another object of the present invention is to provide natriuretic receptor-specific constructs which may be administered by subcutaneous or intravenous injection.

Another object of the present invention is to provide methods for the prophylaxis or treatment of airway diseases, including but not limited to acute asthma and COPD, utilizing natriuretic receptor-specific constructs with increased resistance to degradation but which have a significantly high binding affinity to its receptor.

Another object of the present invention is to provide methods for the prophylaxis or treatment of airway diseases, including but not limited to acute asthma and COPD, utilizing natriuretic receptor-specific constructs with reduced clearance through NPRC, compared to either ANP or BNP, and which preferably bind to NPRC with decreased affinity compared to binding to NPRA.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serves to explain the principles of the invention. The drawings are only for the purpose of illustrating one or more preferred embodiments of the invention and are not to be construed as limiting the invention.

DETAILED DESCRIPTION OF THE INVENTION

Figure 1:
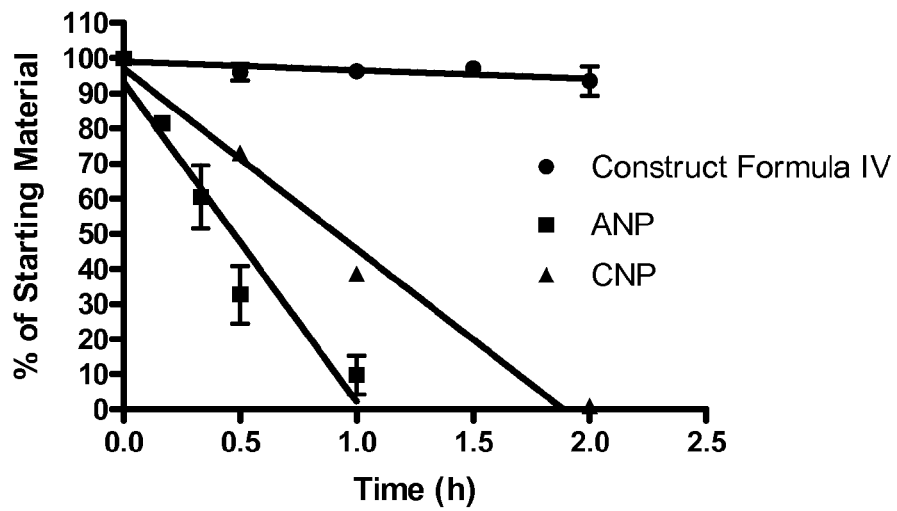
FIG. 1 is a plot of amounts of the construct of formula IV, hANP and hCNP remaining intact after incubation in a 50 μM solution of hNEP.

Natriuretic receptor-specific constructs made of a plurality of amino acid residues, at least one ring-constrained amino acid surrogate and optionally at least one prosthetic group, are described generally in U.S. patent application Ser. No. 11/694,260 entitled "Cyclic Natriuretic Peptide Constructs", filed on Mar. 30, 2007, now U.S. Pat. No. 7,622,440, issued on Nov. 24, 2009; U.S. patent application Ser. No. 11/694,358 entitled "Linear Natriuretic Peptide Constructs", filed on Mar. 30, 2007; U.S. patent application Ser. No. 11/694,181, entitled "Amino Acid Surrogates for Peptidic Constructs", filed on Mar. 30, 2007; U.S. Ser. No. 12/572,284 entitled "Amide Linkage Natriuretic Peptide Constructs", filed on Oct. 2, 2009; U.S. Provisional Patent Application Ser. No. 60/743,963 entitled "Linear Natriuretic Peptide Constructs", filed on Mar. 30, 2006; U.S. Provisional Patent Application Ser. No. 60/743,964 entitled "Linear Natriuretic Peptide Constructs with Prosthetic Groups", filed on Mar. 30, 2006; U.S. Provisional Patent Application Ser. No. 60/743,960 entitled "Cyclic Natriuretic Peptide Constructs", filed on Mar. 30, 2006; U.S. Provisional Patent Application Ser. No. 60/743,961 entitled "Cyclic Natriuretic Peptide Constructs with Prosthetic Groups", filed on Mar. 30, 2006; and U.S. Provisional Patent Application Ser. No. 61/102,407 entitled "Amide Linkage Cyclic Natriuretic Peptide Constructions", filed on Oct. 3, 2008. The methods, formulations and uses of this invention may be practiced with a natriuretic peptide construct as disclosed in any one of the foregoing patent applications, and accordingly the specification and claims of each of the foregoing patent applications are incorporated herein by reference as if set forth in full.

The invention provides methods and uses of natriuretic receptor-specific constructs for the prophylaxis or treatment of airway diseases, including but not limited to acute asthma and COPD, by administration of a pharmaceutically effective amount of a construct as described herein. The natriuretic receptor-specific constructs comprise one or more ring-constrained amino acid surrogates, which surrogates may further comprise a conventional amino protected N-terminus, using a protecting group such as Fmoc, and a reactive carboxyl C-terminus, such that they may thus be employed in conventional peptide synthesis methodologies, it being understood that if the amino acid surrogate is at the C-terminus position of the construct, that other than a carboxyl terminus may be employed on such surrogate.

In a related preferred embodiment, the construct further includes at least one prosthetic group. Preferred prosthetic groups include polymeric groups comprising repeat units including one or more carbon and hydrogen atoms, and optionally other atoms, including oxygen. Such polymeric groups are preferably water-soluble polymers, and are preferably poly(alkylene oxide), poly(vinyl pyrrolidone), poly(vinyl alcohol), polyoxazoline or poly(acryloylmorpholine). A preferred poly(alkylene oxide) is poly(ethylene glycol) (PEG), optionally derivatized with a linking group.

In one particularly preferred embodiment, the invention employs a construct, comprising an amino acid sequence which binds to a natriuretic peptide receptor, wherein one or more amino acid residues in such amino acid sequence which binds to a natriuretic peptide receptor is substituted with an amino acid surrogate of formula I. In one aspect, the amino acid sequence which binds to a natriuretic peptide receptor is, prior to substitution, H-Met-cyclo(Cys-His-Phe-Gly-Gly-Arg-Met-Asp-Arg-Ile-Ser-Cys)-Tyr-Arg-NH$_2$ (SEQ ID NO:1).

In yet another aspect the invention employs a construct that binds to a receptor for a natriuretic peptide, including a receptor for ANP or BNP, and includes at least one amino acid surrogate of formula I or II, but which construct is not homologous to any known peptide that binds to a receptor for a natriuretic peptide.

In one embodiment, the invention employs a cyclic construct of formula III:

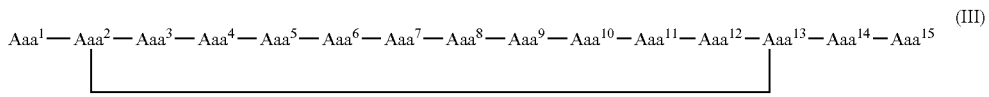

where $Aaa^1$ is an L- or D-isomer of an α-amino acid or β-amino acid or an α, α-disubstituted amino acid derived from an α-amino acid, including where $Aaa^1$ is an L- or D-isomer of an α-amino acid or β-amino acid including or derived from Nle, Ala, Leu, Ile, Val, Arg, Phe, Lys, Tyr, Asp, Nva, Met, Met(O), or Met(O$_2$), or an α, α-disubstituted amino acid derived from Nle, Ala, Leu, Ile, Val, Arg, Phe, Lys, Tyr, Asp, Nva, Met, Met(O), or Met(O$_2$), including all (R) or (S) configurations of α, α-disubstituted amino acids where the substituents are different, or $Aaa^1$ is an acyl comprising a $C_2$ to $C_{18}$ linear alkyl, a $C_3$ to $C_{17}$ branched alkyl, a $C_2$ to $C_{18}$ linear alkenyl or alkynyl or a $C_3$ to $C_{18}$ branched alkenyl or alkynyl, or $Aaa^1$ is an amino acid surrogate of the structure:

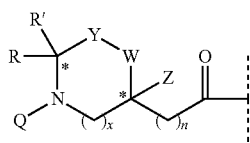

wherein the broken line indicates a peptide bond; R and R' are independently H, a linear or branched $C_1$ to $C_6$ aliphatic chain, —(CH$_2$)$_y$—S—CH$_3$, —(CH$_2$)$_y$—S(=O)—CH$_3$, —(CH$_2$)$_y$—S(O$_2$)—CH$_3$, a bond and a cyclopropane, cyclobutane, cyclopentane, or cyclohexane ring, or a $C_1$ to $C_3$ aliphatic chain and a cyclopropane, cyclobutane, cyclopentane, or cyclohexane ring; x is 1 or 2; Y is CH$_2$ or C=O; W is CH$_2$, NH or NR'''; Z is H or CH$_3$; Q is —H, —(CH$_2$)$_m$—N(v$_3$)(v$_4$), —(CH$_2$)$_m$—CH$_3$, —(CH$_2$)$_m$—O(v$_3$), —(CH$_2$)$_m$—C(=O)—(v$_3$), —(CH$_2$)$_m$—C(=O)—O—(v$_3$), —(CH$_2$)$_m$—S(v$_3$), —C(=O)—(CH$_2$)$_m$—CH$_3$, —C(=O)—(CH$_2$)$_m$—N(v$_3$)(v$_4$), —C(=O)—(CH$_2$)$_m$—C(=O)—(v$_3$), —C(=O)—(CH$_2$)$_m$—O(v$_3$), or —C(=O)—(CH$_2$)$_m$—S(v$_3$); R''' is an acyl, a $C_1$ to $C_{17}$ linear or branched alkyl chain, a $C_2$ to $C_{19}$ linear or branched alkyl acyl chain, a $C_1$ to $C_{17}$ linear or branched omega amino aliphatic, or a $C_1$ to $C_{17}$ linear or branched omega amino aliphatic acyl; n is 0, 1 or 2; m is 0 to 17; y is 1 to 5; v$_3$ and v$_4$ are each independently H, a $C_1$ to $C_{17}$ linear or branched alkyl chain or a $C_2$ to $C_{19}$ linear or branched alkyl acyl chain, on the proviso that if one of v$_3$ or v$_4$ is an alkyl acyl chain, then the other of v$_3$ or v$_4$ is H; and the carbon atoms marked with an asterisk can have any stereochemical configuration;

$Aaa^2$ and $Aaa^{13}$ are the same or different, and are each L- or D-isomer amino acid residues forming a cyclic bridge through the side chains of each of $Aaa^2$ and $Aaa^{13}$, wherein the linking group of the cyclic bridge is —S—S—, —S—CH$_2$—S—, —S—CH$_2$—, —CH$_2$—S—, —C(=O)—NH—, —NH—C(=O)—, —CH$_2$—NH—, —NH—CH$_2$—, —CH$_2$—S(O)$_n$— where n is 1 or 2, —S(O)$_n$—CH$_2$— where n is 1 or 2, —CH$_2$—CH$_2$—, —CH=CH— (E or Z), —C≡C—, —C(=O)—O—, —O—(=O)—, —C(=O)—CH$_2$—, —CH$_2$—C(=O)—, —O—C(=O)—NH—, —NH—C(=O)—O—, or —NH—C(=O)—NH—;

$Aaa^3$ is an L- or D-isomer of an α-amino acid or β-amino acid including or derived from His, Ala, Ser, Thr, Lys, HLys, Orn, Cys, HCys, Dap, or Dab, or an α, α-disubstituted amino acid derived from His, Ala, Ser, Thr, Lys, HLys, Orn, Cys, HCys, Dap, or Dab, including all (R) or (S) configurations of α, α-disubstituted amino acids where the substituents are different, or $Aaa^3$ is an amino acid surrogate of the structure:

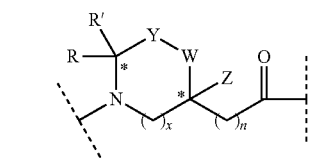

where R and R' are independently H or an amino acid side chain moiety of His, Ala, Ser, Thr, Lys, HLys, Orn, Cys, HCys, Dap, or Dab or a derivative of an amino acid side chain moiety of His, Ala, Ser, Thr, Lys, HLys, Orn, Cys, HCys, Dap, or Dab; x is 1 or 2; Y is CH$_2$ or C=O; W is CH$_2$, NH or NR'''; Z is H or CH$_3$; R''' is an acyl, a $C_1$ to $C_{17}$ linear or branched alkyl chain, a $C_2$ to $C_{19}$ linear or branched alkyl acyl chain, a $C_1$ to $C_{17}$ linear or branched omega amino aliphatic, or a $C_1$ to $C_{17}$ linear or branched omega amino aliphatic acyl; and n is 0, 1 or 2;

$Aaa^4$ is an L- or D-isomer of an α-amino acid or β-amino acid including or derived from substituted or unsubstituted Phe, HPhe or Pgl, or Tyr, Leu, Ile, Val, Ala, Nle, Nva or Tle, or an α, α-disubstituted amino acid derived from substituted or unsubstituted Phe, HPhe or Pgl, or Tyr, Leu, Ile, Val, Ala, Nle, Nva or Tle, including all (R) or (S) configurations of α, α-disubstituted amino acids where the substituents are different, or $Aaa^4$ is an amino acid surrogate as for $Aaa^3$ where R and R' are independently H or an amino acid side chain moiety of substituted or unsubstituted Phe, HPhe or Pgl, or Tyr, Leu, Ile, Val, Ala, Nle, Nva or Tle or a derivative of an amino acid side chain moiety of substituted or unsubstituted Phe, HPhe or Pgl, or Tyr, Leu, Ile, Val, Ala, Nle, Nva or Tle;

Aaa⁵ is Gly, Sar, an L- or D-isomer of an α-amino acid or β-amino acid including or derived from Ala, or Aib, which is the α, α-disubstituted amino acid derived from Ala, or Aaa⁵ is an amino acid surrogate as for Aaa³ where R and R' are independently H or —CH₃;

Aaa⁶ is Gly, Sar, an L- or D-isomer of an α-amino acid or β-amino acid including or derived from Ala, or Aib, or Aaa⁶ is an amino acid surrogate as for Aaa³ where R and R' are independently H or —CH₃;

Aaa⁷ is an L- or D-isomer of an α-amino acid or β-amino acid including or derived from Arg, His, Ala, Ser, HSer, Thr, Lys, HLys, Orn, Cys, HCys, Cit, Abu, Dap, or Dab, or an α, α-disubstituted amino acid derived from Arg, His, Ala, Ser, HSer, Thr, Lys, HLys, Orn, Cys, HCys, Cit, Abu, Dap, or Dab, including all (R) or (S) configurations of α, α-disubstituted amino acids where the substituents are different, or Aaa⁷ is an amino acid surrogate as for Aaa³ where R and R' are independently H or an amino acid side chain moiety of Arg, His, Ala, Ser, HSer, Thr, Lys, HLys, Orn, Cys, HCys, Abu, Dap, or Dab or a derivative of an amino acid side chain moiety of Arg, His, Ala, Ser, HSer, Thr, Lys, HLys, Orn, Cys, HCys, Abu, Dap, or Dab;

Aaa⁸ is Gly, an L- or D-isomer of an α-amino acid or β-amino acid including or derived from Nle, Ile, Leu, Val, Phe, Ala, Nva, Met(O), Met(O₂), or Tle, or an α, α-disubstituted amino acid derived from Nle, Ile, Leu, Val, Phe, Ala, Nva, Met(O), Met(O₂), or Tle, including all (R) or (S) configurations of α, α-disubstituted amino acids where the substituents are different, or Aaa⁸ is an amino acid surrogate as for Aaa³ where R and R' are independently H or an amino acid side chain moiety of Nle, Ile, Leu, Val, Phe, Ala, Nva, Met(O), Met(O₂), or Tle, or a derivative of an amino acid side chain moiety of Nle, Ile, Leu, Val, Phe, Ala, Nva, Met(O), Met(O₂), or Tle;

Aaa⁹ is an L- or D-isomer of an α-amino acid or β-amino acid including or derived from Asp, Glu, His, Ala, Ser, Thr, Lys, HLys, Cys, HCys, Met(O), Met(O₂), Orn, Dap, or Dab, or an α, α-disubstituted amino acid derived from Asp, Glu, His, Ala, Ser, Thr, Lys, HLys, Cys, HCys, Met(O), Met(O₂), Orn, Dap, or Dab, including all (R) or (S) configurations of α, α-disubstituted amino acids where the substituents are different, or Aaa⁹ is an amino acid surrogate as for Aaa³ where R and R' are independently H or an amino acid side chain moiety of Asp, Glu, His, Ala, Ser, Thr, Lys, HLys, Cys, HCys, Met(O), Met(O₂), Orn, Dap, or Dab or a derivative of an amino acid side chain moiety of Asp, Glu, His, Ala, Ser, Thr, Lys, HLys, Cys, HCys, Met(O), Met(O₂), Orn, Dap, or Dab;

Aaa¹⁰ is an L- or D-isomer of an α-amino acid or β-amino acid including or derived from Arg, His, Ala, Ser, Thr, Lys, HLys, Cys, HCys, Cit, Met(O), Orn, Dap, or Dab, or an α, α-disubstituted amino acid derived from Arg, His, Ala, Ser, Thr, Lys, HLys, Cys, HCys, Cit, Met(O), Orn, Dap, or Dab, including all (R) or (S) configurations of α, α-disubstituted amino acids where the substituents are different, or Aaa¹⁰ is an amino acid surrogate as for Aaa³ where R and R' are independently H or an amino acid side chain moiety of Arg, His, Ala, Ser, Thr, Lys, HLys, Cys, HCys, Met(O), Orn, Dap, or Dab or a derivative of an amino acid side chain moiety of Arg, His, Ala, Ser, Thr, Lys, HLys, Cys, HCys, Met(O), Orn, Dap, or Dab;

Aaa¹¹ is Gly or a D- or L-isomer of an α-amino acid or β-amino acid including or derived from Nle, Ile, Leu, Val, Phe, Ala, Nva, Cys, HCys, Abu or Tle, or an α, α-disubstituted amino acid derived from Nle, Ile, Leu, Val, Phe, Ala, Nva, Cys, HCys, Abu or Tle, including all (R) or (S) configurations of α, α-disubstituted amino acids where the substituents are different, or Aaa¹¹ is an amino acid surrogate as for Aaa³ where R and R' are independently H or an amino acid side chain moiety of Nle, Ile, Leu, Val, Phe, Ala, Nva, Cys, HCys, Abu or Tle or a derivative of an amino acid side chain moiety of Nle, Ile, Leu, Val, Phe, Ala, Nva, Cys, HCys, Abu or Tle;

Aaa¹² is Gly, an L- or D-isomer of an α-amino acid or β-amino acid including or derived from Ser, Nle, Ile, Leu, Val, Phe, Ala, Nva, Arg, Lys, Orn, Cys, HCys, Abu or Tle, or an α, α-disubstituted amino acid derived from Ser, Nle, Ile, Leu, Val, Phe, Ala, Nva, Arg, Lys, Orn, Cys, HCys, Abu or Tle, including all (R) or (S) configurations of α, α-disubstituted amino acids where the substituents are different, or Aaa¹² is an amino acid surrogate as for Aaa³ where R and R' are independently H or an amino acid side chain moiety of Ser, Nle, Ile, Leu, Val, Phe, Ala, Nva, Arg, Lys, Orn, Cys, HCys, Abu or Tle or a derivative of an amino acid side chain moiety of Ser, Nle, Ile, Leu, Val, Phe, Ala, Nva, Arg, Lys, Orn, Cys, HCys, Abu or Tle;

Aaa¹⁴ is an L- or D-isomer of an α-amino acid or β-amino acid including or derived from substituted or unsubstituted Phe, HPhe or Pgl, or Tyr, Leu, Ile, Val, Ala, Lys, Orn, Nle, Nva or Tle, or an α, α-disubstituted amino acid derived from substituted or unsubstituted Phe, HPhe or Pgl, or Tyr, Leu, Ile, Val, Ala, Lys, Orn, Nle, Nva or Tle, including all (R) or (S) configurations of α, α-disubstituted amino acids where the substituents are different, or Aaa¹⁴ is an amino acid surrogate of the structure of formula II as for Aaa³ where R and R' are independently H or an amino acid side chain moiety of substituted or unsubstituted Phe, HPhe or Pgl, or Tyr, Leu, Ile, Val, Ala, Lys, Orn, Nle, Nva or Tle or a derivative of an amino acid side chain moiety of substituted or unsubstituted Phe, HPhe or Pgl, or Tyr, Leu, Ile, Val, Ala, Lys, Orn, Nle, Nva or Tle; and Aaa¹⁵ is a D- or L-isomer of an α-amino acid or β-amino acid including or derived from Ala, Arg, Orn, Lys, Ala, Dap, Dab, HArg, or HLys, or an α, α-disubstituted amino acid derived from Ala, Arg, Orn, Lys, Ala, Dap, Dab, HArg, or HLys, including all (R) or (S) configurations of α, α-disubstituted amino acids where the substituents are different, or Aaa¹⁵ is an amino acid surrogate of the structure:

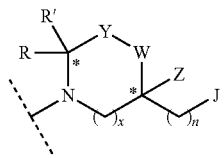

wherein the broken line indicates a peptide bond; at least one of R and R' is —(CH₂)$_y$—R" and if one, the remaining of R and R' is H, where R" is:

—NH₂,
—NH—C(=NH)—NH₂,
—NH—(CH₂)$_y$—NH₂,
—NH—C(=O)—NH₂,
—C(=O)—NH₂,
—C(=O)—NH—CH₃,
—C(=O)—NH—(CH₂)$_y$—NH₂,
—NH—C(=NH)—NH-Me,
—NH—C(=NH)—NH-Et,
—NH—C(=NH)—NH—Pr,
—NH—C(=NH)—NH—Pr-i,
—NH—C(=O)—CH₃,
—NH—C(=O)—CH₂—CH₃,
—NH—C(=O)—CH—(CH₃)₂,

—NH—C(=O)—O—CH₃,
—NH—C(=O)—O—CH₂—CH₃,
—NH—C(=O)—O—C—(CH₃)₃,
—NH—C(=O)—NH—CH₃,
—NH—C(=N—C(=O)—O—C—(CH₃)₃)—NH—C(=O)—O—C—(CH₃)₃,
—N(C(=O)—O—C—(CH₃)₃)—C(=NH)—NH—C(=O)—O—C—(CH₃)₃,

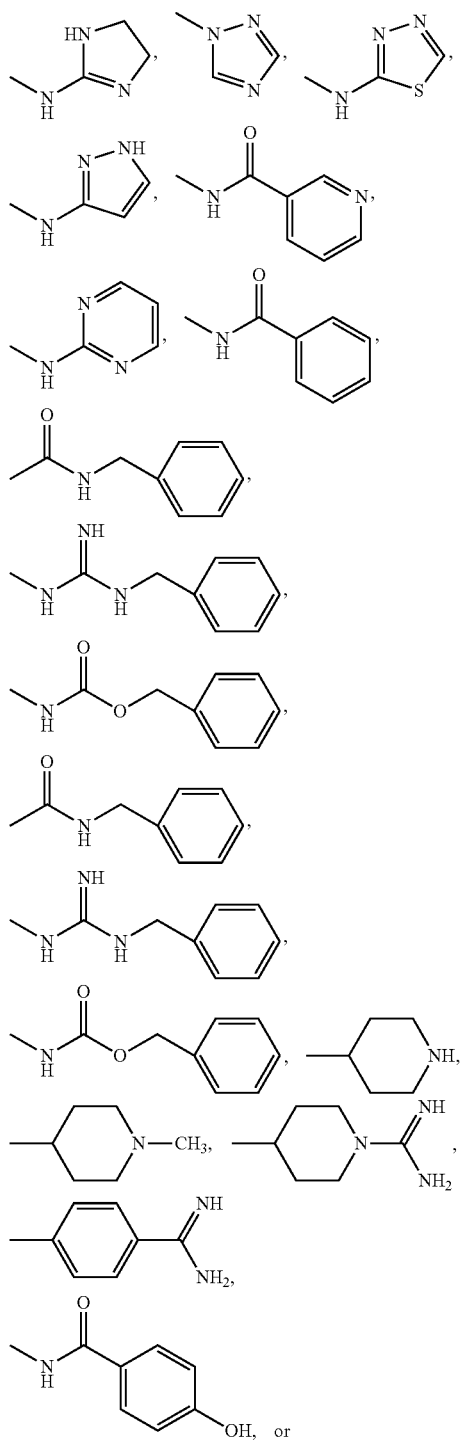

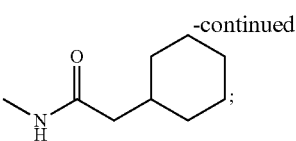

x is 1 or 2; Y is $CH_2$ or C=O; W is $CH_2$, NH or NR'''; Z is H or $CH_3$; J is —H, —$(CH_2)_m$—OH, —C(=O)—$CH_2)_m$—OH, —C(=O)—$CH_2)_m$—N$(v_1)(v_2)$, —C(=O)—O—$(CH_2)_m$—$CH_3$, —O—$(CH_2)_m$—$CH_3$, —O—$(CH_2)_m$—N$(v_1)(v_2)$, —O—$(CH_2)_m$—OH, —C(=O)—NH—$(CH_2)_m$—$CH_3$, —C(=O)—NH—$(CH_2)_m$—N$(v_1)(v_2)$, —C(=O)—NH—$(CH_2)_m$—S$(v_1)$, —C(=O)—N—$((CH_2)_m$—N$(v_1)(v_2))_2$, —C(=O)—NH—CH(—C(=O)—OH)—$(CH_2)_m$—N$(v_1)(v_2)$, —C(=O)—NH—$(CH_2)_m$—NH—C(=O)—CH(N$(v_1)(v_2))((CH_2)_m$—N$(v_1)(v_2))$, —C(=O)—NH—CH(—C(=O)—N$(v_1)(v_2))$—$(CH_2)_m$—N$(v_1)(v_2)$, an omega amino aliphatic, terminal aryl or aralkyl group, any single natural or unnatural α-amino acid, β-amino acid or α,α-disubstituted amino acid in combination with one of the foregoing groups defining J, or any single natural or unnatural α-amino acid, β-amino acid or α,α-disubstituted amino acid, including all (R) and (S) configurations of any of the foregoing; R''' is an acyl, a $C_1$ to $C_{17}$ linear or branched alkyl chain, a $C_2$ to $C_{19}$ linear or branched alkyl acyl chain, a $C_1$ to $C_{17}$ linear or branched omega amino aliphatic, or a $C_1$ to $C_{17}$ linear or branched omega amino aliphatic acyl; $v_1$ and $v_2$ are each independently H or a $C_1$ to $C_{17}$ linear or branched alkyl chain; n is 0, 1 or 2; m is 0 to 17; y is 1 to 5; and the carbon atoms marked with an asterisk can have any stereochemical configuration;

on the proviso that at least one of $Aaa^1$, $Aaa^3$ through $Aaa^{12}$, $Aaa^{14}$ or $Aaa^{15}$ is an amino acid surrogate.

A related embodiment of formula III provides a construct where one or more of $Aaa^1$, $Aaa^3$ to $Aaa^{12}$, $Aaa^{14}$ or $Aaa^{15}$ is an amino acid surrogate as defined above, and where a prosthetic group, as hereafter defined, is attached to a reactive group of a side chain of an amino acid residue at one or more of $Aaa^1$, $Aaa^3$ to $Aaa^{12}$, $Aaa^{14}$ or $Aaa^{15}$, to a reactive R or R' group of an amino acid surrogate at $Aaa^3$ to $Aaa^{12}$ or $Aaa^{14}$, directly or through a Q group to the terminal amine of an amino acid surrogate at $Aaa^1$, to a reactive terminal carboxyl of an amino acid surrogate at $Aaa^{15}$, or to a reactive group forming a part of J of an amino acid surrogate at $Aaa^{15}$. The reactive group to which the one or more prosthetic groups are covalently bonded may be a primary amine, a secondary amine, a carboxyl group, a thiol group or a hydroxyl group. In one aspect, the prosthetic group may be covalently bound to a reactive amine in position $Aaa^1$, $Aaa^3$, $Aaa^7$, $Aaa^{10}$, $Aaa^{12}$, or $Aaa^{15}$, or a combination of the foregoing. In another aspect, the prosthetic group may be covalently bound to a reactive carboxyl in position $Aaa^9$ or $Aaa^{15}$, or both. In another aspect, the prosthetic group may be covalently bound to a reactive thiol in position $Aaa^3$, $Aaa^7$, $Aaa^9$, $Aaa^{10}$, $Aaa^{11}$, or $Aaa^{12}$, or a combination of the foregoing.

In a preferred aspect of the construct of formula III, one, two or three of $Aaa^1$ to $Aaa^{15}$ (excluding $Aaa^2$ and $Aaa^{13}$) are an amino acid surrogate of one of the foregoing formulas. In a first particularly preferred aspect, one of $Aaa^1$, $Aaa^5$ and $Aaa^{15}$ is an amino acid surrogate. In a second particularly preferred aspect, two of $Aaa^1$, $Aaa^5$ and $Aaa^{15}$ are amino acid surrogates. In a third particularly preferred aspect, each of $Aaa^1$, $Aaa^5$ and $Aaa^{15}$ are amino acid surrogates. In another particularly preferred aspect, one, two or three of $Aaa^1$, $Aaa^5$ and $Aaa^{15}$ are amino acid surrogates, and the construct is a cyclic construct formed by disulfide bond formation through the side chains of Aaa² and Aaa¹³. In another particularly preferred aspect, where two or more of Aaa¹ to Aaa¹⁵ are amino acid surrogates the amino acid surrogates are not contiguous, which is to say that each amino acid surrogate is separate from each other amino acid surrogate by at least one amino acid residue being interposed therebetween in the primary sequence.

In yet another preferred embodiment, in the construct of formula III at least one of Aaa³, Aaa⁵, Aaa⁶, Aaa⁷, Aaa⁹, Aaa¹⁰, or Aaa¹² is an L- or D-isomer of Ala, preferably an L-isomer of Ala.

In a particularly preferred embodiment, the construct of formula III is a natriuretic receptor-specific construct of formula IV:

(SEQ ID NO: 3)

(IV)

Hept-Cys-His-Phe-D-Ala-Gly-Arg-D-Nle-Asp-Arg-Ile-Ser-Cys-Tyr or a pharmaceutically acceptable salt of the construct of formula IV.

In yet another embodiment, the invention provides methods for the prophylaxis or treatment of airway diseases, including but not limited to acute asthma and COPD, utilizing a construct of formula III further comprising one or more non-peptide bonds. Non-peptide bonds may be employed to decrease the susceptibility of a construct of the invention to degradation, such as improving the in vivo stability of constructs towards tryptic-like proteases by replacing the native peptide bond before each Lys or Arg residue with a non-peptide bond, such as an isostere of an amide, a substituted amide or a peptidomimetic linkage. In one specific embodiment, native peptide bonds are replaced with peptide bonds having a reversed polarity. In general, any non-peptide bond may be employed, and may be utilized between any two residues. A non-peptide bond includes bonds in which the carbon atom participating in the bond between two residues is reduced from a carbonyl carbon to a methylene carbon, such as a non-peptide bond —$CH_2$—NH— or its isostere —NH—$CH_2$—, or the use of other bonds such as —$CH_2$—S—, —$CH_2$—O—, or —C(=O)—$CH_2$— or an isostere of any of the foregoing, or —$CH_2$—$CH_2$— or —CH=CH—. In general, non-peptide bonds include an imino, ester, hydrazine, semicarbazide, oxime, or azo bond.

The constructs defined above may include one or more prosthetic groups. Prosthetic groups may be employed to modulate the residence time in circulation, to modulate bioavailability, modulate immunogenicity of constructs, or the like. In general, prosthetic groups "modulate" by increasing the residence time, bioavailability or the like, as the case may be, but prosthetic groups may optionally decrease residence time, bioavailability or the like. A "prosthetic group" thus includes any compound conjugated, such as by a covalent bond, to a construct of any formula, for purposes of improving pharmacokinetic or pharmacodynamic properties of the construct. Preferred prosthetic groups include polymeric groups, comprising repeat units which in turn comprise one or more carbon and hydrogen atoms, and optionally other atoms, including oxygen atoms. Such polymeric groups are preferably water-soluble polymers, and are preferably poly (alkylene oxide), poly(vinyl pyrrolidone), poly(vinyl alcohol), polyoxazoline or poly(acryloylmorpholine). A preferred poly(alkylene oxide) is poly(ethylene glycol) (PEG). In addition to PEG, other poly(alkylene glycol) polymers may be employed, such as poly(propylene glycol) and poly (butylene glycol).

In one embodiment, the prosthetic group is one or more PEG polymers covalently bound to a reactive group of the construct. The PEG polymer, or other prosthetic group, may be covalently bound to a reactive group on the side chain of one or more amino acid residues, or may be covalently bound to a reactive group on an amino acid surrogate. Such reactive groups of an amino acid surrogate may include a group covalently bound, directly or through one or more intermediates, to Q or J, or may include a reactive group forming a part of R or R'.

If PEG is employed as the prosthetic group, the PEG polymer may have a molecular weight of from about 200 MW to about 50000 MW. The PEG polymer may be linear, and if linear, may be monofunctional, with a reactive group at one end and a non-reactive group at the other end, homobifunctional, with the same reactive group at each end, or heterobifunctional, with a different reactive group at each end. Alternatively, the PEG polymer may be branched, having generally a "Y"-shaped configuration, multi-armed, such as with two, three, four or eight arms, or other configurations known in the art. The PEG polymer preferably has at least one derivatized reactive group for linking to one or more defined groups on the construct of formula III, preferably by means of a covalent bond. The derivativized reactive group may link to, for example, an amine, hydroxyl, thiol, or carboxyl group on a construct, including on a terminal group of an amino acid residue, on a side chain of an amino acid residue, on a Q group of a surrogate, on a J group of a surrogate, or on an R or R' group of a surrogate.

The PEG polymer preferably has, at one end, an end-cap group, such as a hydroxyl, alkoxy, substituted alkoxy, alkenoxy, substituted alkenoxy, alkynoxy, substituted alkynoxy, aryloxy or substituted aryloxy. The PEG polymer further preferably has, at at least one other end, a derivatized reactive group. In one embodiment, the PEG polymer is a linear or branched polyether with a terminal hydroxyl group, such as a monomethoxy PEG, which is derivatized with a linking group, such as an amine, maleimide or carboxylic acid. The available reactive groups of the construct dictate the derivatized linking group employed on the PEG polymer. Thus, in one embodiment, the N-terminal amine of the construct is employed, using a carboxylic acid derivatized PEG. In another embodiment, the C-terminal amine of the construct is employed, again using a carboxylic acid derivatized PEG. In yet another embodiment, if a Lys residue or homolog thereof is present in the construct, either the α or ε amino group thereof may be employed, again using a carboxylic acid derivatized PEG. Maleimide derivatized PEG may be employed with either a reactive thiol or hydroxyl group on the construct. Similarly, amine derivatized PEG may be employed with a reactive carboxyl group on any terminal group or side chain of an amino acid residue, on a Q group of a surrogate, on a J group of a surrogate, or on an R or R' group of a surrogate.

Thus, in one aspect, PEG is activated with one or more electrophilic groups and may be employed for coupling to amino groups of the construct, including coupling to an ε amino group of a side chain or an N-terminal or C-terminal amine. Representative electrophilic reactive groups include succinimidyl α-methylbutanoate and other α-methylbutyric acid esters, as disclosed in U.S. Pat. Nos. 5,672,662 and 6,737,505, and may be be used with proteins, as disclosed in U.S. Patent Application Publication 2004/0235734. Alternatively, succinimidyl propionate may be employed as a reactive group, as disclosed in U.S. Pat. No. 5,567,662, or N-hydroxysuccinimide may be employed with a branched PEG, as disclosed in U.S. Pat. No. 5,932,462. The teachings of each of the foregoing patents and patent applications are incorporated by reference as if set forth in full.

In another aspect, PEG polymers are provided with one or more reactive aldehyde groups, and employed for coupling to a terminal primary amine, such as an N-terminal or C-terminal amine. In another aspect, PEG polymers are provided with one or more thiol-reactive groups, such as a maleimide, orthopyridyldisulfide, or thiol group, and are employed for coupling to a reactive thiol in the construct of formula III, such as a reactive thiol in a cysteine side chain or a reactive thiol in a Q group of a construct.

In one aspect, any of the methods, conjugates or schemes as disclosed in International Patent Publication No. WO 2004/047871, or any reference cited therein, may be employed with the constructs of this invention. The teaching of the foregoing patent applications is incorporated by reference as if set forth in full.

In general, some form of chemical modification may be employed to make an active PEG derivative with a reactive group. The reactive group may be an active carbonate, an active ester, an aldehyde, or tresylate. In part, the reactive group of the PEG determines the amino acid terminal group or side chain moiety to which the PEG derivative is bound. In general, site specific PEGylation is preferred, in part because the resulting construct is homogeneous, minimizing loss of biological activity and reducing immunogenicity.

In one embodiment, the PEG has a molecular weight of from about 200 MW to about 50,000 MW, more preferably from about 2,000 MW to about 20,000 MW. In another embodiment, monomethoxy PEG, such as of the formula $CH_3$—$O(CH_2$—$CH_2$—$O)_n$—$CH_2$—$CH_2$—OH or $CH_3$—O($CH_2$—$CH_2$—$O)_n$—H, where n is any integer from 2 to about 1200, is employed, preferably derivatized with an amine, maleimide or carboxylic acid linking group.

In another embodiment, the prosthetic group, such as PEG, is conjugated to a construct by means of an enzymatically labile linker as described in Veronese F M and Pasut G. Pegylation, "Successful approach to drug delivery." *Drug Discovery Today* 10:1451-1458 (2005), and the methods disclosed therein are incorporated here by reference.

In another embodiment, the prosthetic group employed is a polymer with both a lipophilic moiety and a hydrophilic polymer moiety, as disclosed in U.S. Pat. Nos. 5,359,030 and 5,681,811. In a related embodiment, the prosthetic group employed is an oligomer conjugate with a hydrophilic component, such as a PEG polymer, and a lipophilic component, such as a branched fatty acid or alkyl chain, linked by a hydrolyzable bond, such as an ester bond, as disclosed in U.S. Pat. No. 6,309,633. In another related embodiment, the prosthetic group employed is an oligomer that includes poly(propylene glycol), and preferably at least two poly(propylene glycol) subunits, as disclosed in U.S. Pat. No. 6,858,580. The teachings of each of the foregoing patents and patent applications are incorporated by reference as if set forth in full.

In yet another embodiment, the teachings of U.S. Published Patent Application 2004/0203081 are incorporated here by reference, including specifically teachings relating to prosthetic groups, referred to in such application as "modifying moieties," attached to various natriuretic compounds, and specifically oligomeric structures having a variety of lengths and configurations. In a related embodiment, the teachings of International Patent Publication WO 2004/047871 are incorporated by reference, including teachings related to "modifying moieties" attached by means of "modifying moiety conjugation sites" to natriuretic molecules binding to NPRA, it being understood that similar methods could be employed with natriuretic molecules binding to other natriuretic receptors.

Certain terms as used throughout the specification and claims are defined as follows.

The "construct" and "amino acid residue sequences" employed in this invention can be a) naturally-occurring, b) produced by chemical synthesis, c) produced by recombinant DNA technology, d) produced by biochemical or enzymatic fragmentation of larger molecules, e) produced by methods resulting from a combination of methods a through d listed above, or f) produced by any other means for producing peptides or amino acid sequences.

By employing chemical synthesis, a preferred means of production, it is possible to introduce various amino acids which do not naturally occur into the construct, modify the N- or C-terminus, and the like, thereby providing for improved stability and formulation, resistance to protease degradation, and the like, and to introduce one or more amino acid surrogates into the construct.

The term "peptide" as used throughout the specification and claims is intended to include any structure comprised of two or more amino acids, including chemical modifications and derivatives of amino acids. The amino acids forming all or a part of a peptide may be naturally occurring amino acids, stereoisomers and modifications of such amino acids, non-protein amino acids, post-translationally modified amino acids, enzymatically modified amino acids, and the like. The term "peptide" also includes dimers or multimers of peptides. A "manufactured" peptide includes a peptide produced by chemical synthesis, recombinant DNA technology, biochemical or enzymatic fragmentation of larger molecules, combinations of the foregoing or, in general, made by any other method.

The term "amino acid side chain moiety" used in this invention, including as used in the specification and claims, includes any side chain of any amino acid, as the term "amino acid" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition. A "derivative of an amino acid side chain moiety" as hereafter defined is included within the definition of an amino acid side chain moiety.

The "derivative of an amino acid side chain moiety" is a modification to or variation in any amino acid side chain moiety, including a modification to or variation in either a naturally occurring or unnatural amino acid side chain moiety, wherein the modification or variation includes: (a) adding one or more saturated or unsaturated carbon atoms to an existing alkyl, aryl, or aralkyl chain; (b) substituting a carbon in the side chain with another atom, preferably oxygen or nitrogen; (c) adding a terminal group to a carbon atom of the side chain, including methyl (—$CH_3$), methoxy (—$OCH_3$), nitro (—$NO_2$), hydroxyl (—OH), or cyano (—C≡N); (d) for side chain moieties including a hydroxy, thiol or amino groups, adding a suitable hydroxy, thiol or amino protecting group; or (e) for side chain moieties including a ring structure, adding one or ring substituents, including hydroxyl, halogen, alkyl, or aryl groups attached directly or through an ether linkage. For amino groups, suitable amino protecting groups include, but are not limited to, Z, Fmoc, Boc, Pbf, Pmc and the like.

The "amino acids" used in embodiments of the present invention, and the term as used in the specification and claims, include the known naturally occurring protein amino acids, which are referred to by both their common three letter abbreviation and single letter abbreviation. See generally *Synthetic Peptides: A User's Guide* G. A. Grant, editor, W. H. Freeman & Co., New York (1992), the teachings of which are incorporated herein by reference, including the text and table set forth at pages 11 through 24. An "amino acid" includes conventional α-amino acids and further includes β-amino acids, α, α-disubstituted amino acids and N-substituted amino acids wherein at least one side chain is an amino acid side chain moiety as defined herein. An "amino acid" further includes N-alkyl α-amino acids, wherein the N-terminus amino group has a $C_1$ to $C_6$ linear or branched alkyl substituent. It may thus be seen that the term "amino acid" includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V. J., Al-obeidi F., Kazmierski W., *Biochem. J.* 268:249-262 (1990); and Toniolo C., *Int. J. Peptide Protein Res.* 35:287-300 (1990); the teachings of all of which are incorporated herein by reference. In addition, the following abbreviations, including amino acids and protecting and modifying groups thereof, have the meanings given:

Abu—gamma-amino butyric acid
12-Ado—12-amino dodecanoic acid
Aib—alpha-aminoisobutyric acid
6-Ahx—6-amino hexanoic acid
Amc—4-(aminomethyl)-cyclohexane carboxylic acid
8-Aoc—8-amino octanoic acid
Bip—biphenylalanine
Boc—t-butoxycarbonyl
Bzl—benzyl
Bz—benzoyl
Cit—citrulline
Dab—diaminobutyric acid
Dap—diaminopropionic acid
Dip—3,3-diphenylalanine
Disc—1,3-dihydro-2H-isoindolecarboxylic acid
Et—ethyl
Fmoc—fluorenylmethoxycarbonyl
Hept—heptanoyl ($CH_3$—$(CH_2)_5$—C(=O)—)
Hex—hexanoyl ($CH_3$—$(CH_2)_4$—C(=O)—)
HArg—homoarginine
HCys—homocysteine
HLys—homolysine
HPhe—homophenylalanine
HSer—homoserine
Me—methyl
Met(O)—methionine sulfoxide
Met($O_2$)—methionine sulfone
Nva—norvaline
Pgl—phenylglycine
Pr—propyl
Pr-i—isopropyl
Sar—sarcosine
Tle—tert-butylalanine
Z—benzyloxycarbonyl In the listing of constructs according to the present invention, conventional amino acid residues have their conventional meaning as given in Chapter 2400 of the *Manual of Patent Examining Procedure*, $8^{th}$ Ed. Thus, "Nle" is norleucine; "Asp" is aspartic acid; His is histidine; "Arg" is arginine; "Trp" is tryptophan; "Lys" is lysine; "Gly" is glycine; "Pro" is proline; "Tyr" is tyrosine, "Ser" is serine and so on. All residues are in the L-isomer configuration unless the D-isomer is specified, as in "D-Ala" for D-alanine.

A single amino acid, including stereoisomers and modifications of naturally occurring protein amino acids, non-protein amino acids, post-translationally modified amino acids, enzymatically synthesized amino acids, derivatized amino acids, an α, α-disubstituted amino acid derived from any of the foregoing (i.e., an α, α-disubstituted amino acid wherein at least one side chain is the same as that of the residue from which it is derived), a β-amino acid derived from any of the foregoing (i.e., a β-amino acid which other than for the presence of a β-carbon is otherwise the same as the residue from which it is derived) and the like, including all of the foregoing, is sometimes referred to herein as a "residue."

An "α, α-disubstituted amino acid" includes any α-amino acid having a further substituent in the α-position, which substituent may be the same as or different from the side chain moiety of the α-amino acid. Suitable substituents, in addition to the side chain moiety of the α-amino acid, include $C_1$ to $C_6$ linear or branched alkyl. Aib is an example of an α, α-disubstituted amino acid. While α, α-disubstituted amino acids can be referred to using conventional L- and D-isomeric references, it is to be understood that such references are for convenience, and that where the substituents at the α-position are different, such amino acid can interchangeably be referred to as an α, α-disubstituted amino acid derived from the L- or D-isomer, as appropriate, of a residue with the designated amino acid side chain moiety. Thus (S)-2-Amino-2-methylhexanoic acid can be referred to as either an α, α-disubstituted amino acid derived from L-Nle or as an α, α-disubstituted amino acid derived from D-Ala. Whenever an α, α-disubstituted amino acid is provided, it is to be understood as including all (R) and (S) configurations thereof.

An "N-substituted amino acid" includes any amino acid wherein an amino acid side chain moiety is covalently bonded to the backbone amino group, optionally where there are no substituents other than H in the α-carbon position. Sarcosine is an example of an N-substituted amino acid. By way of example, sarcosine can be referred to as an N-substituted amino acid derivative of Ala, in that the amino acid side chain moiety of sarcosine and Ala is the same, methyl.

The term "amino acid surrogate" includes a molecule disclosed herein which is a mimic of a residue, including but not limited to piperazine core molecules, keto-piperazine core molecules and diazepine core molecules. Unless otherwise specified, an amino acid surrogate is understood to include both a carboxyl group and amino group, and a group corresponding to an amino acid side chain, or in the case of an amino acid surrogate of glycine, no side chain other than hydrogen. Thus an amino acid surrogate includes a molecule of the general formula of formula I or II given above. An amino acid surrogate further includes molecules of any of the following structures, it being understood that for convenience such structures are given as the isolated surrogate, not including any protecting group and not bound by one or two peptide bonds to one or two amino acid residues forming a part of a construct of the invention:

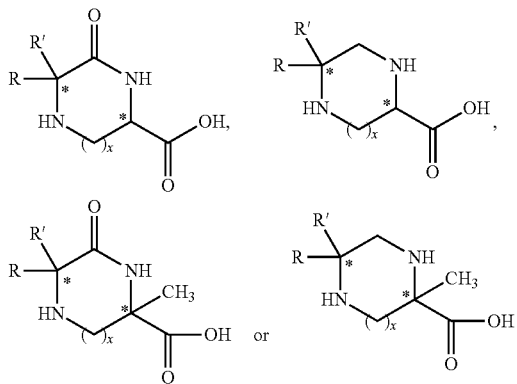

where R, R', x and the asterisks are as defined for the surrogate of formula I. An amino acid surrogate further includes molecules of any of the following structures, again it being understood that for convenience such structures are given as the isolated surrogate, not including any protecting group and not bound by one or two peptide bonds to one or two amino acid residues forming a part of a construct of the invention:

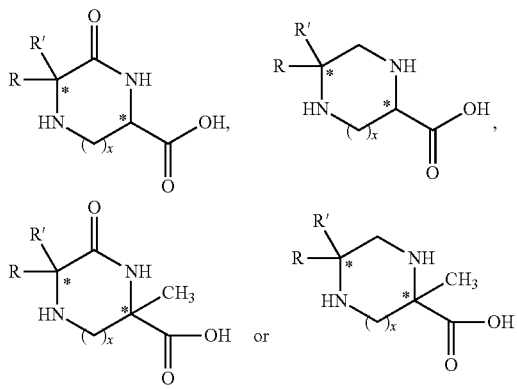

where R, R', x and the asterisks are as defined for the surrogate of formula I. For purposes of synthesis, either the carboxyl group or the amino group of any amino acid surrogate is preferably protected by a protecting group, such that it is not reactive while the protecting group is present, and similarly any reactive group forming a part of R or R' may similarly be protected by a protecting group. It will be appreciated that the surrogates of the present invention have more than one asymmetric center, and therefore are capable of existing in more than one stereoisomeric form. Some of the compounds may also exist as geometric isomers and rotamers. Furthermore, some compounds of the invention may also have conformational axial chirality resulting in atropisomers. The invention extends to each of these forms individually and to mixtures thereof, including racemates. In one aspect, surrogate isomers may be separated conventionally by chromatographic methods or by use of a resolving agent. In another aspect, individual surrogate isomers, or enantiomerically pure surrogates, are prepared by synthetic schemes, such as those disclosed herein or variants of such schemes, employing asymmetric synthesis using chiral intermediates, reagents or catalysts.

The term "C-terminus capping group" includes any terminal group attached through the terminal ring carbon atom or, if provided, terminal carboxyl group, of the C-terminus of a construct. The terminal ring carbon atom or, if provided, terminal carboxyl group, may form a part of a residue, or may form a part of an amino acid surrogate. In a preferred aspect, the C-terminus capping group forms a part of an amino acid surrogate which is at the C-terminus position of the construct. The C-terminus capping group includes, but is not limited to, —$(CH_2)_n$—OH, —$(CH_2)_n$—C(=O)—OH, —$(CH_2)_m$—OH, —$(CH_2)_n$—C(=O)—N($v_1$)($v_2$), —$(CH_2)_n$—C(=O)—$(CH_2)_m$—N($v_1$)($v_2$), —$(CH_2)_n$—O—$(CH_2)_m$—$CH_3$, —$(CH_2)_n$—C(=O)—NH—$(CH_2)_m$—$CH_3$, —$(CH_2)_n$—C(=O)—NH—$(CH_2)_m$—N($v_1$)($v_2$), —$(CH_2)_n$—C(=O)—N(($CH_2)_m$—N($v_1$)($v_2$))$_2$, —$(CH_2)_n$—C(=O)—NH—CH(—C(=O)—OH)—$(CH_2)_m$—N($v_1$)($v_2$), —C(=O)—NH—$(CH_2)_m$—NH—C(=O)—CH(N($v_1$)($v_2$))(($CH_2)_m$—N($v_1$)($v_2$)), or —$(CH_2)_n$—C(=O)—NH—CH(—C(=O)—$NH_2$)—$(CH_2)_m$—N($v_1$)($v_2$), including all (R) or (S) configurations of the foregoing, where $v_1$ and $v_2$ are each independently H, a $C_1$ to $C_{17}$ linear or branched alkyl chain, m is 0 to 17 and n is 0 to 2; or any omega amino aliphatic, terminal aryl or aralkyl, including groups such as methyl, dimethyl, ethyl, propyl, isopropyl, butyl, isobutyl, pentyl, hexyl, allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc or 8-Aoc, or any single natural or unnatural α-amino acid, β-amino acid or α, α-disubstituted amino acid, including all (R) or (S) configurations of the foregoing, optionally in combination with any of the foregoing non-amino acid capping groups. In the foregoing, it is to be understood that, for example, —C(=O)—NH—$(CH_2)_m$—NH—C(=O)—CH(N($v_1$)($v_2$))(($CH_2)_m$—N($v_1$)($v_2$)) is:

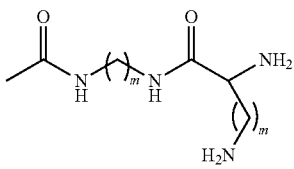

The term "N-terminus capping group" includes any terminal group attached through the terminal amine of the N-terminus of a construct. The terminal amine may form a part of a residue, or may form a part of an amino acid surrogate. In a preferred aspect, the N-terminus capping group forms a part of an amino acid surrogate which is at the N-terminus position of the construct. The N-terminus capping group includes, but is not limited to, any omega amino aliphatic, acyl group or terminal aryl or aralkyl including groups such as methyl, dimethyl, ethyl, propyl, isopropyl, butyl, isobutyl, pentyl, hexyl, allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc or 8-Aoc, or alternatively an N-terminus capping group is —(CH$_2$)$_m$—NH(v$_3$), —(CH$_2$)$_m$—CH$_3$, —C(=O)—(CH$_2$)$_m$—CH$_3$, —C(=O)—(CH$_2$)$_m$—NH(v$_3$), —C(=O)—(CH$_2$)$_m$—C(=O)—OH, —C(=O)—(CH$_2$)$_m$—C(=O)-(v$_4$), —(CH$_2$)$_m$—C(=O)—OH, —(CH$_2$)$_m$—C(=O)—(v$_4$), C(=O)—(CH$_2$)$_m$—O(v$_3$), —(CH$_2$)$_m$—O(v$_3$), C(=O)—(CH$_2$)$_m$—S(v$_3$), or —(CH$_2$)$_m$—S(v$_3$), where v$_3$ is H or a C$_1$ to C$_{17}$ linear or branched alkyl chain, and v$_4$ is a C$_1$ to C$_{17}$ linear or branched alkyl chain and m is 0 to 17.

A phenyl ring is "substituted" when the phenyl ring includes one or more substituents independently comprising hydroxyl, halogen, alkyl, or aryl groups attached directly or through an ether linkage. Where the phenyl ring is so substituted, the amino acid residue may be referred to as substituted, as in substituted Phe, substituted HPhe or substituted Pgl.

The term "alkene" includes unsaturated hydrocarbons that contain one or more double carbon-carbon bonds. Examples of alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of alkyl radicals include methyl, ethyl, propyl, isopropyl, butyl, sec-butyl, tertiary butyl, pentyl, isopentyl, hexyl, isohexyl, and the like.

The term "alkynyl" includes a linear monovalent hydrocarbon radical of two to six carbon atoms or a branched monovalent hydrocarbon radical of three to six carbon atoms containing at least one triple bond; examples thereof include ethynyl, propynal, butynyl, and the like.

The term "aryl" includes a monocyclic or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of aryl groups include phenyl, biphenyl, naphthyl, 1-naphthyl, and 2-naphthyl, derivatives thereof, and the like.

The term "aralkyl" includes a radical —R$^a$R$^b$ where R$^a$ is an alkylene (a bivalent alkyl group) and R$^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

The term "acyl" includes a group R—C(=O)—, where R is an organic group. An example is the acetyl group CH$_3$—C(=O)—, referred to herein as "Ac".

A peptide or aliphatic moiety is "acylated" when an aryl, alkyl or substituted alkyl group as defined above is bonded through one or more carbonyl {—(C=O)—} groups. A peptide is most usually acylated at the N-terminus.

An "omega amino aliphatic" includes an aliphatic moiety with a terminal amino group. Examples of omega amino aliphatics include 7'-amino-heptanoyl and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

An "amide" includes compounds that have a trivalent nitrogen attached to a carbonyl group (—C(=O)—NH$_2$), such as for example methylamide, ethylamide, propylamide, and the like.

An "imide" includes compounds containing an imido group (—C(=O)—NH—C(=O)—).

An "amine" includes compounds that contain an amino group (—NH$_2$).

A "nitrile" includes compounds that are carboxylic acid derivatives and contain a (—CN) group bound to an organic group.

The term "halogen" is intended to include the halogen atoms fluorine, chlorine, bromine and iodine, and groups including one or more halogen atoms, such as —CF$_3$ and the like.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a construct of the present invention and a pharmaceutically acceptable carrier.

The term "EC$_{50}$" is intended to include the molar concentration of an agonist which produced 50% of the maximum possible response for that agonist. By way of example, a construct which, at a concentration of 72 nM, produces 50% of the maximum possible response for that construct as determined in a cGMP assay, has an EC$_{50}$ of 72 nM. Unless otherwise specified, the molar concentration associated with an EC$_{50}$ determination is in nanomoles (nM).

The term "Ki (nM)" is intended to include the equilibrium receptor binding affinity representing the molar concentration of a competing compound that binds to half the binding sites of a receptor at equilibrium in the absence of a competitor. In general, the Ki is inversely correlated to the affinity of the compound for the receptor, such that if the Ki is low, the affinity is high. Ki may be determined using the equation of Cheng and Prusoff (Cheng Y., Prusoff W. H., *Biochem. Pharmacol.* 22: 3099-3108, 1973):

$$Ki = \frac{EC_{50}}{1 + \frac{[ligand]}{K_d}}$$

where "ligand" is the concentration of ligand, which may be a radioligand, and K$_d$ is an inverse measure of receptor affinity which produces 50% receptor occupancy. Unless otherwise specified, the molar concentration associated with a Ki determination is nM.

The chemical naming protocol and structure diagrams used herein employ and rely on the chemical naming features as utilized by the ChemDraw program (available from Cambridgesoft Corp., Cambridge, Mass.). In particular, certain compound names were derived from the structures using the Autonom program as utilized by Chemdraw Ultra or ISIS base (MDL Corp.). In general, structure diagrams do not depict hydrogen atoms associated with carbon atoms other than in terminal groups and other special circumstances.

Certain structure diagrams and drawings herein, such as those included in Tables 1 and 2, depict constructs composed of amino acid surrogates and amino acid residues, with the surrogates identified by structure diagrams and the amino acid residues identified by a three letter abbreviation. Unless otherwise specified, it is understood that the bond between the surrogate and residue, or between the residue and surrogate, or between a surrogate and residues on both the N-terminus and C-terminus side thereof, is a conventional peptide bond, —C(=O)—NH— or, in the case where the peptide bond is to the ring nitrogen on the N-terminus of the surrogate, —C(=O)—N—. In general, in the depiction of such bonds the atoms of the amino acid surrogate are depicted (e.g., —C(=O)— or —N), but atoms of the amino acid residue are not depicted.

Formulation and Utility

The constructs disclosed herein can be used for both medical applications and animal husbandry or veterinary applications. Typically, the construct, or a pharmaceutical composition including the construct, is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

The methods and uses disclosed herein may be employed for the prophylaxis or treatment of airway diseases, including but not limited to acute asthma and chronic obstructive pulmonary disease (COPD).

Airway diseases include any inflammatory pulmonary condition, disease or syndrome. Exemplary inflammatory pulmonary conditions include infection-induced pulmonary conditions such as those associated with viral, bacterial, fungal, parasite or prion infections; allergen induced pulmonary conditions; pollutant induced pulmonary conditions such as asbestosis, silicosis, or berylliosis; gastric aspiration induced pulmonary conditions, immune dysregulation, genetically induced inflammatory pulmonary conditions such as cystic fibrosis, and physical trauma induced pulmonary conditions, such as ventilator injury. These inflammatory pulmonary conditions also include asthma, emphysema, bronchitis, COPD, sarcoidosis, histiocytosis, lymphangiomyomatosis, acute lung injury, acute respiratory distress syndrome, chronic lung disease, bronchopulmonary dysplasia, community-acquired pneumonia, nosocomial pneumonia, ventilator-associated pneumonia, sepsis, viral pneumonia, influenza infection, parainfluenza infection, human metapneumovirus infection, respiratory syncitial virus infection and aspergillus or other fungal infections.

In one aspect, there is provided a method for the treatment of an airway diseases that results from or is related to COPD, also known as chronic obstructive airway diseases, including but not limited to diseases characterized by the pathological limitation of airflow in the airway that is not fully reversible, such as for example chronic bronchitis, emphysema, pneumoconiosis, pulmonary neoplasms and other lung disorders. This method may be employed to treat COPD which is not responsive, or not adequately responsive, to treatment with existing drugs, such as with a bronchodilator, a corticosteroid, an expectorant or a methylxanthine, typically delivered by means of an inhaler or a nebulizer. Alternatively, the method of this invention, and the uses of the constructs herein, may be used to treat COPD without regard to whether the COPD is responsive, or adequately responsive, to treatment with existing drugs.

In another aspect, there is provide a method for the treatment of asthma, including acute asthma, brochial asthma, pediatric asthma, severe asthma or chronic asthma, which is not responsive, or not adequately responsive, to treatment with a beta-agonist. Thus the patient may, by way of example and not limitation, have asthma that is not responsive, or not adequately responsive, to a conventional "rescue inhaler" or other inhalation device device delivering a beta-agonist such as albuterol (VENTOLIN, PROVENTIL®), formoterol (FORADIL®), levalbuterol (XOPENEX®), metaproterenol (ALUPENT®), pirbuterol (MAXAIR®) or salmeterol (SEREVENT®).

In a related aspect, there is provide a method for the treatment of asthma, including acute asthma, brochial asthma, pediatric asthma, severe asthma or chronic asthma, which is not responsive, or not adequately responsive, to treatment with a drug, substance or method intended to treat or alleviate symptoms of any form of asthma. Thus the patient may, by way of example and not limitation, have asthma that is not responsive, or not adequately responsive, to an anticholinergic agent, typically intended to enhance beta-agonist effectiveness, such as ipratrpium (ATROVENT®) or tiotropium (SPIRIVA®). Alternatively, the patient may, by way of example and not limitation, have asthma that is not responsive, or not adequately responsive, to an inhaled or systemically-administered corticosteroid, such as inhaled corticosteroids such as beclomethasone (QVAR®), budesonide (PULMICORT®), flunisolide (AEROBID®), fluticasone (FLOVENT®) or triamcinolone (AZMACORT®). Alternatively, the patient may, by way of example and not limitation, have asthma that is not responsive, or not adequately responsive, to a leukotriene inhibitor such as montelukast (SINGULAIR®), zafirlukast (ACCOLATE®) or zileuton (ZYFLO®). Alternatively, the patient may, by way of example and not limitation, have asthma that is not responsive, or not adequately responsive, to a methylxanthine such as theophylline (THEO-24®, THEO-DUR®). Alternatively, the patient may, by way of example and not limitation, have asthma that is not responsive, or not adequately responsive, to a mast cell inhibitor, such as cromolyn sodium (INTAL®) or nedocromil (TILADE®). Alternatively, the patient may, by way of example and not limitation, have asthma that is not responsive, or not adequately responsive, to a monoclonal antibody that binds to human immunoglobulin E such as Omalizumab (XOLAIR®). Alternatively, the patient may, by way of example and not limitation, have asthma that is not responsive, or not adequately responsive, to a combination of one or more of the foregoing and a beta agonist, including but not limited to combination therapy drugs such as ADVAIR® (fluticasone and salmeterol) and SYMBICORT® (budesonide and formoterol). Alternatively, the patient may, by way of example and not limitation, have asthma that is not responsive, or not adequately responsive, to a combination of two or more of the foregoing.

The methods and uses disclosed herein may further be used for the treatment of any airway disease, condition or syndrome for which induction of anti-hypertensive, anti-inflammatory, cardiovascular, renal, and/or endocrine effects are desired. Thus the constructs disclosed herein may be employed to cause desired vasodilation in a patient.

Salt Form of Constructs.

The constructs of this invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include salts of aluminum, ammonium, calcium, copper, ferric, ferrous, lithium, magnesium, manganic, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the construct of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the constructs of this invention are prepared in a suitable solvent from the construct and an excess of an acid, such as hydrochloric, hydrobromic, sulfuric, phosphoric, acetic, trifluoroacetic, citric, tartaric, maleic, succinic or methanesulfonic acid. The acetate salt form is especially useful. Where the constructs of embodiments of this invention include an acidic moiety, suitable pharmaceutically acceptable salts may include alkali metal salts, such as sodium or potassium salts, or alkaline earth metal salts, such as calcium or magnesium salts.

In addition, Applicants have advantageously discovered that certain salt forms of the peptide constructs of the invention, including pamoate, octanoate, decanoate, oleate, stearate, sodium tannate and palmitate salt forms, have an increased circulation half-life, in some cases doubled, versus the corresponding acetate salt form. These salt forms are particularly well-suited for administration by subcutaneous injection or intramuscular injection, especially for chronic treatment, due to the reduced frequency of dosing that may be achieved as a result of the longer half-lives. While not being limited by theory, it is believed the increased half-life is related to a decrease in solubility in comparison to the acetate salt form. The increased half-life salt forms of the peptide constructs of the invention may be manufactured by any method including, for example, ion exchange, mixing a solution of an acetate salt form of a construct with disodium pamoate to form a pamoate suspension, or use of the desired salt during the final purification step(s) in the manufacture of the constructs.

Pharmaceutical Compositions.

Another embodiment of the present invention provides a pharmaceutical composition that includes a construct of this invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The constructs of the several embodiments of the present invention may be formulated or compounded into pharmaceutical compositions that include at least one construct of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, manniton, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a construct of this invention over a period of time. For example, gelatin, sodium carboxymethylcellulose and/or other cellulosic excipients may be included to provide time-release or slower-release formulations, especially for administration by subcutaneous and intramuscular injection.

In general, the actual quantity of constructs administered to a patient will vary between fairly wide ranges depending on the mode of administration, the formulation used, and the response desired.

In practical use, the constructs can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, dermal, transdermal, pulmonary, deep lung, inhalation, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Constructs may be administered parenterally. Solutions or suspensions of these active peptides may be prepared in water suitably mixed with a surfactant such as hydroxy-propylcellulose. Dispersions may also be prepared in glycerol, liquid polyethylene glycols and mixtures thereof in oils. These preparations may optionally contain a preservative to prevent the growth of microorganisms. Lyophilized single unit formulations may also be utilized, which are reconstituted, such as with saline, immediately prior to administration, and thus do not require a preservative.

The pharmaceutical forms suitable for injectable use include, for example, sterile aqueous solutions or dispersions and sterile powders, such as lyophilized formulations, for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

Constructs as disclosed herein may be in an aqueous solution, such as a solution including saline, citrate or other common excipients or preservatives, with delivery by means such as use of a nebulizer. The constructs may also be in a dry or powder formulation, with delivery by means of a powder transport system such as a dry powder inhaler.

In one aspect the methods and uses include administration of a construct directly into an airway or the lung. Intrapulmonary administration may be performed by means of a metered dose inhaler, including a device allowing self-administration of a metered bolus of a construct of this invention when actuated by a patient during inspiration. A metered dose inhaler can comprise the construct in solution in a pressurized canister that contains a propellant. Any of a variety of propellents can be employed, including hydrofluoroalkane propellants utilized with metered dose inhalers and similar devices.

Alternatively, either dry powder inhalation or nebulized aerosols may be employed, which release a dose of the compound as either a powder aerosol or an aerosol created from an acqueous formulation. Dry powder inhalers can be activated upon inhalation by the patient. Nebulizers may employ compressed air or oxygen to form a jet, or may utilize a high frequency ultrasonic wave to form a vapor mist.

In one aspect, the construct may be in a dried and particulate form, for example particles between about 0.5 and 6.0 µm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With micro-particles, the constructs may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 µm.

If in an aqueous solution, certain constructs of the present invention may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, acetate and the like, a 50 mM solution may be employed. In addition to buffering agents, a suitable preservative may be employed, to prevent or limit bacteria and other microbial growth. One such preservative that may be employed is 0.05% benzalkonium chloride.

It is also possible and contemplated that the construct may be in a dried and particulate form. In a preferred embodiment, the particles are between about 0.5 and 6.0 µm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With micro-particles, the constructs may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 µm.

Microparticle size, including mean size distribution, may be controlled by means of the method of making. For micromilling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

Any of a variety of dry powder inhalation formulations and compositions may be employed. This includes, by way of example and not limitation, the systems and methods as disclosed in U.S. Pat. Nos. 7,521,068, 7,803,404 and 7,794,754, U.S. Patent Application Publication 2011/0079318 and International Patent Publication No. WO 2009/088553; microparticle or nanoparticle compositions as disclosed in International Patent Publication Nos. WO 2009/103035, WO 2010/144785 and WO 2010/144789 and U.S. Patent Application Publications 2009/0181100 and 2010/0310660; dry powder pharmaceutical formulations as disclosed in U.S. Pat. No. 7,541,022 and U.S. Patent Application Publication 2010/0300440; and dry powder inhalation devices as disclosed in U.S. Pat. No. 6,182,655, U.S. Patent Application Publication 2010/0065048 and International Patent Publication No. WO 2010/135340.

Applications and Uses.

In one embodiment, there is providing a method which includes administering an amount sufficient to inhibit, reduce or decrease progression, severity, frequency, probability, duration or prevent one or more adverse physiological or psychological symptoms caused by or associated with a chronic or acute condition, disorder or disease caused by or associated with undesirable or abnormal lung or airway inflammation, asthma, or a respiratory, interstitial, or pulmonary disease or disorder. In particular aspects, a condition, disorder or disease is allergic asthma, an acute asthmatic episode, airway constriction, or lung or airway inflammation, or a respiratory, interstitial, or pulmonary disease or disorder.

Invention treatment methods include providing a given subject with an objective or subjective improvement of the condition, disorder or disease, a symptom caused by or associated with the condition, disorder or disease, or the probability or susceptibility of a subject to the condition or a symptom caused by or associated with the condition, disorder or disease. In various embodiments, treatment reduces, decreases, inhibits, delays, eliminates or prevents the probability, susceptibility, severity, frequency, or duration of one or more symptoms caused by or associated with the condition, disorder or disease. In a particular aspect, a method inhibits, reduces or decreases the probability, severity, frequency or duration of a subject from having an acute asthmatic episode (e.g., an acute asthmatic episode caused by an allergen, allergic asthma or exercise). In another particular aspect, a method reduces the probability, severity, frequency or duration, or delays, halts, or prevents, airway constriction. In additional aspects, treatment improves or increases airway dilation. In further aspects, a treatment improves asthma, reduces or inhibits lung or airway inflammation, or reduces or inhibits a symptom caused by or associated with a respiratory, interstitial, or pulmonary disease or disorder.

Candidate subjects for methods of the invention include mammals, such as humans. Candidate subjects for methods of the invention also include subjects that are in need of treatment, e.g., any subject that may benefit from a treatment. Candidate subjects for methods of the invention therefore include subjects that have or are at risk of having a condition, disorder or disease caused by or associated with asthma, lung or airway inflammation, or a respiratory, interstitial, or pulmonary disease or disorder. In particular aspects, a subject has been diagnosed as having asthma, lung or airway inflammation, or a respiratory, interstitial, or pulmonary disease or disorder, or is at risk of having asthma, lung or airway inflammation, or a respiratory, interstitial, or pulmonary disease or disorder.

Routes of Administration.

One preferred route of administration of a construct for prophylaxis or treatment of airway disease is by administration directly into an airway or the lung. By way of example, Intrapulmonary administration may be performed by means of a metered dose inhaler, a device allowing self-administration of a metered bolus of a construct of this invention when actuated by a patient during inspiration. Both dry powder inhalation and nebulized aerosols may be employed for administration into an airway or the lung.

If a construct for prophylaxis or treatment of airway disease is systemically administered, it may be administered by injection, and the injection may be intravenous, subcutaneous, intramuscular, intraperitoneal or other means known in the art. The constructs of this invention may further be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the constructs of this invention are introduced across an epidermal layer of cells may be employed. Administration means may thus include administration through mucous membranes, buccal administration, oral administration, dermal administration, inhalation administration, pulmonary administration, nasal administration, urethral administration, vaginal administration, and the like.

In one aspect, a construct of this invention is administered by means of a time-release injectable formulation, such as a construct of this invention in a formulation with a PEG, poly(ortho ester) or PLGA polymer. In another aspect, a construct of this invention is administered by means of an automated delivery device providing subcutaneous delivery, either continuous or intermittent. Any of the foregoing methods and formulations are particularly applicable for treatment of chronic conditions or syndromes, including airway diseases such as asthma or COPD.

Therapeutically Effective Amount.

In general, in the methods and uses of this invention the actual quantity of a construct administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus, a therapeutically effective amount includes an amount of a construct or pharmaceutical composition of this invention that is sufficient to induce a desired effect, including but not limited to inhibition of airway reactivity, inhibition of airway inflammation or airway remodeling.

Methods of the invention can be practiced by administration or contact with any dose amount, frequency, delivery route or timing of a construct as disclosed herein. In particular embodiments, a subject is administered or contacted construct as disclosed herein one, two, three, four or more times hourly, daily, biweekly, weekly, monthly or annually. In additional embodiments, an amount administered is about 0.00001 mg/kg, to about 10,000 mg/kg, about 0.0001 mg/kg, to about 1000 mg/kg, about 0.001 mg/kg, to about 100 mg/kg, about 0.01 mg/kg, to about 10 mg/kg, about 0.1 mg/kg, to about 1 mg/kg body weight, one, two, three, four, or more times per hour, day, biweekly, week, month or annually. In further embodiments, the amount administered is less than about 0.001 mg/kg, such as between about 0.0001 and 0.0005 mg/kg, administered one, two, three, four, or more times per hour, day, biweekly, week, month or annually. In particular aspects, the amount is administered substantially contemporaneously with, or within about 1-60 minutes, hours, or days of the onset of a symptom caused by or associated with asthma, lung or airway inflammation, or a respiratory, interstitial, or pulmonary disease or disorder.

Combination Therapy

It is also possible and contemplated that the methods and uses of this invention include use of constructs in combination with other drugs or agents. In certain embodiments, an effective amount of one or more constructs is administered in combination with an effective amount of one or more therapies used for preventing, treating, managing, or ameliorating asthma. Non-limiting examples of therapies for asthma include anti-cholinergics (e.g., ipratropium bromide and oxitropium bromide), beta-2 agonists (e.g., albuterol (PROVENTIL® or VENTOLIN®), bitolterol (TOMALATEL®), fenoterol, formoterol, isoetharine, metaproterenol, pibuterol (MAXAIR®), salbutamol, salbutamol terbutaline, and salmeterol, terbutlaine (BRETHAIREL®)), corticosteroids (e.g., prednisone, beclomethasone dipropionate (VANCERIL® or BECLOVENT®), triamcinolone acetonide (AZMACORF®), flunisolide (AEROBID®), and fluticasone propionate (FLOVENT®)), leukotriene antagonists (e.g., montelukast, zafirluckast, and zileuton), theophylline (THEO-DUR®, UNIDU® tablets, and SLO-BID® Gyrocaps), and salmeterol (SEREVENT®), cromolyn, and nedorcomil (INTAL® and TILADE®)), IgE antagonists, IL-4 antagonists (including antibodies), IL-5 antagonists (including antibodies), PDE4 inhibitors, NF-Kappa-B inhibitors, IL-13 antagonists (including antibodies), CpG, CD23 antagonists, selectin antagonist (e.g., TBC 1269), mast cell protease inhibitors, tryptase kinase inhibitors (e.g., GW-45, GW-58, and genisteine), phosphatidylinositide-3' (PI3)-kinase inhibitors (e.g., calphostin C), other kinase inhibitors (e.g., staurosporine), C2a receptor antagonists (including antibodies), and supportive respiratory therapy, such as supplemental and mechanical ventilation. In certain embodiments, the method comprises administration of an effective amount of a construct in combination of one or more supportive measures to a subject to prevent, treat, manage, or ameliorate asthma or one or more symptoms thereof. Non-limiting examples of supportive measures include humidification of air by ultrasonic nebulizer, aerolized racemic epinephrine, oral dexamethasone, intravenous fluids, intubation, fever reducers (e.g., ibuprofen and acetametaphine), and antibiotic, anti-viral, or anti-fungal therapy (i.e., to prevent or treat secondary respiratory infections).

In general a construct of this invention, including the construct of formula IV, may be used in combination with a long acting beta agonist, a short acting beta agonist, a long acting muscarinic antagonist, a short acting muscarinic antagonist, a bifunctional muscarinic antagonist and beta agonist, or a corticosteroid. In one aspect, a construct of this invention, including the construct of formula IV, is formulated with one of the foregoing in a formulation adapted for administration directly into an airway or the lung, such as by inhalation therapy. Thus by way of example a construct of formula IV can be combined with one or more of an inhaled corticosteroid, an inhaled muscarinic antagonist or an inhaled beta agonist. In another aspect, a construct of this invention, including the construct of formula IV, is formulated with one of the foregoing in a formulation adapted for parenteral administration. Thus by way of example a construct of formula IV can be combined with one or more of a parenteral form of a steroid, such as hydrocortisone, methylprednisolone or dexamethasone, for administration by subcutaneous, intramuscular or intravenous means.

Synthetic Methods of Amino Acid Surrogates

The following examples of methods of synthesis of amino acid surrogates utilized in the invention are intended to be exemplary, and it is to be understood that variations thereon may be undertaken by one of skill in the art, and such variations are intended to be included herein.

Method A:

(2-Fmoc-amino-3-R'—O-propylamino)-2-substituted acetic acid methyl esters (10) were prepared by reductive amination of Fmoc O-protected serinal (9) with α-amino esters (2), using either sodium cyanoborohydride or sodium triacetoxyborohydride as the reducing agent. The Fmoc O-protected serinal (9) required for the reductive amination was prepared according to method D, either by reduction of the ester (12) by di-isobutylaluminun hydride, by oxidation of Fmoc O-protected serinol (13) with Dess-Martin periodinane, or by reduction of the Fmoc O-protected serine Weinreb amide (14) with lithium aluminum hydride. The preferred method for the preparation of Fmoc O-protected serinals (9) was the reduction of the Weinreb amide analog. (2-Fmoc-amino-3-R'—O-propylamino)-2-substituted acetic acid methyl esters (10) were then N and O deprotected, cyclized, and Fmoc protected to give 3-substituted 6-hydroxymethyl-piperazin-2-ones (6), which were then oxidized to the final product as described in method A.

The protecting group (R') on the hydroxyl group of Fmoc-O-protected serinal (9) used in the synthesis depends on the nature of the side chain R of the amino ester. When R contained no functional groups, the side chain of Fmoc serine was protected as the ′Bu ether. When R contained functional groups, the side chain of Fmoc serine was protected as the trityl ether.

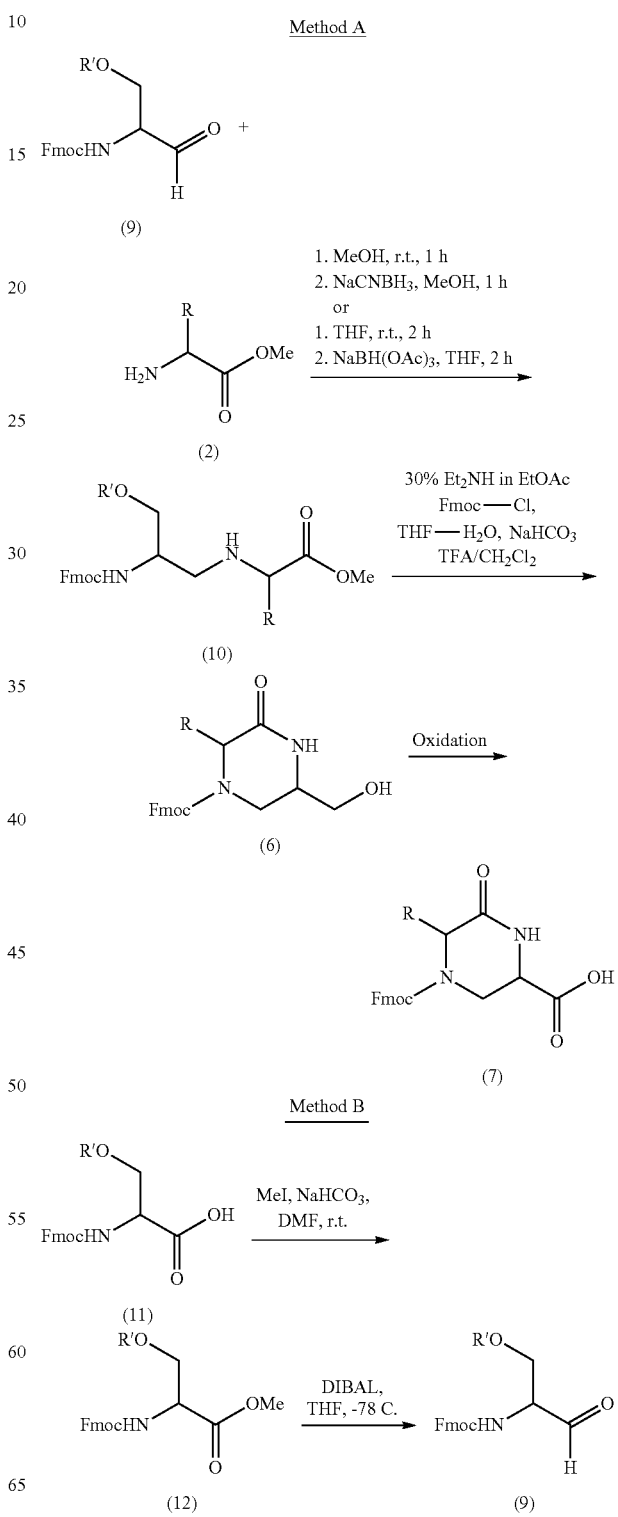

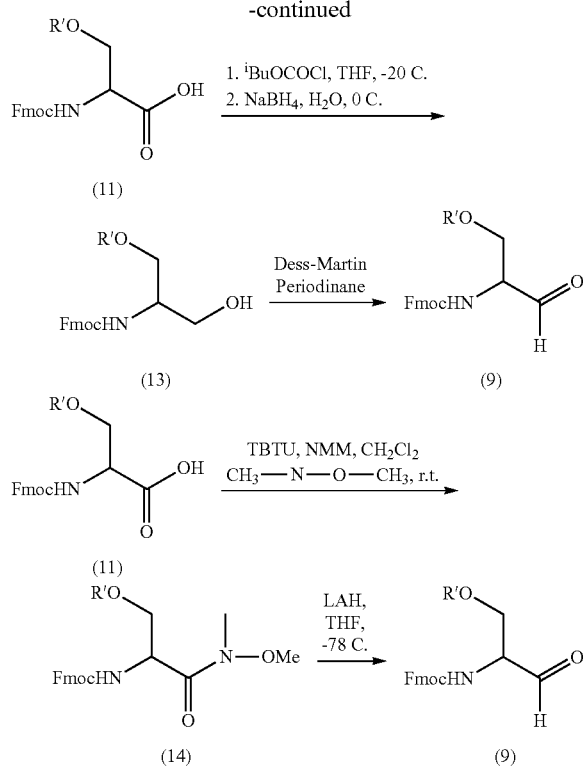

Method B:

Synthesis of various Fmoc-O-protected serinals (9). Synthesis of Fmoc-O—R' serine methyl ester (12): A slight suspension of 80 mmol of Fmoc O—R' serine (11), 10.0 g (120 mmol) of solid sodium bicarbonate, and 10.0 mL (160 mmol) of iodomethane in 80 mL of dry dimethylformamide, kept under nitrogen, was stirred at room temperature overnight. The reaction mixture was then poured over 500 mL of water, and the solid filtered. The solid was redissolved in 800 mL of ethyl acetate, and washed with 1×200 mL of water, dried over magnesium sulfate, and concentrated. No purification was required.

| R' | Analytical Data for Compounds (12) |
|---|---|
| $^t$Bu | $^1$H NMR δ (CDCl$_3$): 1.14 (s, 9H, $^t$Bu), 3.57-3.70 (m, 1H, CH$_2$—O), 3.75 (s, 3H, O—CH$_3$), 3.79-3.83 (m, 1H, CH$_2$—O), 4.01-4.50 (a series of multiples, 4H), 5.64-5.68 (d, 1H, NH), 7.28-7.78 (8H, fulvene), yield = 93% $t_R$ = 7.8 min. |
| Trt | $^1$H NMR δ (CDCl$_3$): 3.42-3.48 (m, 1H, CH$_2$—O), 3.59-3.66 (m, 1H, CH$_2$—O), 3.81 (s, 3H, CH$_3$—O), 4.10-4.18 (m, 1H, CH), 4.36-4.42 (m, 2H, CH$_2$—O), 4.50-4.57 (m, 1H, CH—N), 5.73-5.78 (d, 1H, NH), 7.22-7.82 (8H, fulvene), yield = quant., $t_R$ = 9.04 min. |

Synthesis of Fmoc-O—R' serinol (13): To a solution of 10.0 mmol of Fmoc O—R' serine (11) in 50 mL of dry tetrahydrofuran, kept at −20° C. under nitrogen, was added 1.77 mL (12.7 mmol) of triethyl amine, followed by the slow addition of 1.57 mL (12.0 mmol) of isobutylchloroformate. The mixture was stirred for 30 minutes, and then poured slowly over an ice-cold solution of 3.77 g (99.6 mmol) of sodium borohydride in 10 mL of water, keeping the temperature below 5° C. The reaction was stirred at 0° C. for 15 minutes, and then quenched with 1N hydrochloric acid solution. The reaction mixture was diluted with 100 mL of ethyl acetate, and the layers separated. The organic layer was washed with 2×25 mL of 1N hydrochloric acid solution, 2×25 mL of water, dried over magnesium sulfate and concentrated. The compounds were purified by silica gel column chromatography.

| R' | Analytical Data for Compounds (13) |
|---|---|
| $^t$Bu | $^1$H NMR δ (CDCl$_3$): 1.14 (s, 9H, $^t$Bu), 2.90-2.95 (d, ½H, CH$_2$—O), 3.63 (d, 2H, CH$_2$—O), 3.65-3.93 (m, 3H, CH$_2$—O), 4.20-4.35 (t, 1H, CH), 4.35-4.45 (d, 2H, CH$_2$), 5.50-5.57 (d, 1H, NH), 7.26-7.8 (8H, fulvene), yield = 85%, $t_R$ = 6.42 min. |
| Trt | $^1$H NMR δ (CDCl$_3$): 3.24-3.32 (br. d, 1H, CH$_2$—O), 3.30-3.45 (br. m, 1H, CH$_2$—O), 3.60-3.987 (br. m, 3H, CH$_2$—O, and CH—N), 4.13-4.22 (br. m, 1H, CH), 4.32-4.40 (br. d, 2H, CH$_2$), 5.24-5.32 (br. d, 1H, NH), 7.16-7.76 (23H, fulvene, and Trt), yield = 92%, $t_R$ = 8.39 min. |

Synthesis of Fmoc-O—R' serine Weinreb amide (14): A suspension of 20.2 mmol of Fmoc O—R' serine (11), 6.98 g (21.6 mmol) of 2-(1H-benzotriazol-1-yl)-1,1,3,3-tetramethyluronium tetrafluoroborate (TBTU), and 2.5 mL (22.7 mmol) of N-methyl-morpholine in 80 mL of dry dichloromethane was stirred at room temperature under nitrogen for 20 minutes, and then 3.02 g (31 mmol) of N,O-di-methyl-hydroxylamine hydrochloride and 3.3 mL (30 mmol) of N-methyl-morpholine were added, and the suspension stirred at room temperature overnight. The solution formed was then concentrated to dryness, repartitioned between 200 mL of ethyl acetate and 100 mL of water, washed with 2×40 mL of 1N hydrochloric acid solution and then 2×40 mL of saturated sodium bicarbonate solution, dried over magnesium sulfate, and concentrated. No purification was required.

| R' | Analytical Data for Compounds (14) |
|---|---|
| $^t$Bu | $^1$H NMR δ (CDCl$_3$): 1.45 (s, 9H, $^t$Bu), 3.30 (s, 3H, CH$_3$—N), 3.55-3.7 (m, 2H, CH$_2$—O), 3.76 (s, 3H, CH$_3$—O), 4.19-4.26 (m, 1H, CH), 4.30-4.38 (m, 2H, CH$_2$—O), 4.82-4.91 (broad m, 1H, CHN), 5.68-5.75 (d, 1H, NH), 7.2-7.8 (8H, fulvene), yield = quant., $t_R$ = 6.59 min. |
| Trt | $^1$H NMR δ (CDCl$_3$): 3.24 (s, 3H, CH$_3$N), 3.34-3.46 (m 2H, CH$_2$O), 3.62 (s, 3H, CH$_3$O), 4.15-4.37 (two m, CH$_2$, CH), 4.86-4.98 (m 1H, CHN), 5.80-5.86 (d, 1H, NH), 7.18-7.8 (a series of m, 23H, Trt and fulvene), yield = quant., $t_R$ = 8.0 min. |

Synthesis of Fmoc-O—R' serinal (9) from ester (12): To a solution of 3.5 mmol of (12) in 5 mL of tetrahydrofuran, kept at −78° C. under nitrogen, was added slowly 10 mL of 1N diisobutyl aluminum hydride (DIBAL) solution, stirred for 15 minutes, and quenched by the slow addition of a saturated solution of sodium and potassium tartrate. The reaction was allowed to warm up to room temperature, diluted with 50 mL of ethyl acetate, and 50 mL of a saturated solution of sodium and potassium tartrate was added. The layers were separated, and the aqueous layer re-extracted with 1×50 mL of ethyl acetate. The organic layers were combined, dried over magnesium sulfate, and concentrated. Compounds (9) were used without further purification in the next step.

| R' | Analytical Data for Compounds (9) |
|---|---|
| $^t$Bu | $^1$H NMR δ (CDCl$_3$): 1.16 (s, 9H, $^t$Bu), 3.59-3.66 (dd, 1H, CH$_2$O), 3.90-3.98 (dd, 1H, CH$_2$O), 4.20-4.27 (t, 1H, CH), 4.32-4.45 (two m, 3H, CHN, and CH$_2$O), 5.64-5.74 (br. d, 1H, NH), 7.28-7.35 (m, 2H, fulvene), 7.36-7.44 (m, 2H, fulvene), 7.58-7.65 (d, 2H, fulvene), 7.73-7.78 (d, 2H, fulvene), 9.62 (s, 1H, CHO). |
| Trt | $^1$H NMR δ (CDCl$_3$): 3.53-3.61 (dd, 1H, CH$_2$O), 3.66-3.75 (dd, 1H, CH$_2$O), 4.33-4.47 (two m, 4H, CHN, CH, and CH$_2$), |

| R' | Analytical Data for Compounds (9) |
|---|---|
| | 5.66-5.75 (d, 1H, NH), 7.20-7.81 (a series of m, 23H, Trt, and fulvene), 9.6 (s, 1H, CHO). |

Synthesis of Fmoc-O—R' serinal (9) from alcohol (13): To a solution of 80 mmol of Fmoc-O—R' serinol (13) in 200 mL of dry dichloromethane, kept at room temperature under nitrogen, was added 88 mmol of Dess-Martin periodinane, and the reaction was stirred for 2.5 hours and quenched by addition of 400 mL of 10% aqueous sodium thiosulfate solution. The layers were separated, and the organic layer concentrated, diluted with 300 mL of ethyl ether, and washed three times with a saturated aqueous bicarbonate solution containing 10% sodium thiosulfate, dried over magnesium sulfate, and concentrated.

Synthesis of Fmoc-O—R' serinal (9) from Weinreb amide (14): To a solution of 8.8 g (20.2 mmol) of crude Fmoc-O—R' serine Weinreb amide intermediate (14) in 60 mL of dry tetrahydrofuran, cooled to −78° C. under nitrogen, was added 30 mL of 1N lithium aluminum hydride solution in tetrahydrofuran. The solution was stirred for 15 minutes and then quenched by the slow addition of 30 mL of a 1.4N solution of potassium hydrogen sulfate. After warming up to room temperature, the solid was filtered and the filtrate concentrated to dryness. The residue was repartitioned between 50 mL of ethyl acetate and 25 mL of 1N hydrochloric acid solution. The layers separated, and the organic layer was dried over magnesium sulfate, filtered, and concentrated.

Synthesis of (2-Fmoc-amino-3-R'—O-propylamino)-2-substituted acetic acid methyl ester (10): compounds (10) were prepared by reductive amination using sodium cyanoborohydride or sodium triacetoxyborohydride as the reducing agent.

Sodium cyanoborohydride method: To a solution of 8.5 mmol of (2) hydrochloride salt in 20 mL of methanol, kept at room temperature under nitrogen, was added 2.3 mmol of solid potassium hydroxide, and the mixture stirred for 25 minutes. A solution of Fmoc-O—R' serinal (9) in 10 mL of methanol was added to the above suspension, and the reaction mixture was stirred for 1 hour. A solution of 8.5 mL of 1N sodium cyanoborohydride in tetrahydrofuran was added slowly, and the reaction stirred for another 1 hour, filtered, and concentrated. The residue was partitioned between ethyl acetate and water, and the organic layer washed with 1×20 mL of saturated sodium bicarbonate, dried over sodium sulfate, and concentrated.

Sodium triacetoxyborohydride method: A suspension of 21 mmol of (2) hydrochloride salt, and 2.9 mL (21 mmol) of triethyl amine in 50 mL of dry tetrahydrofuran, was stirred at room temperature for 45 min, and then a solution of ~20 mmol crude Fmoc-(O—R')-serinal (9) in 30 mL of tetrahydrofuran was added, followed by 1.7 g of 4 A powdered molecular sieves, and the suspension was stirred for an additional 2 h. 6.4 g (30 mmol) of solid sodium triacetoxyborohydride was added, and the suspension stirred at room temperature overnight. The suspension was diluted with methanol, the molecular sieves filtered, and the filtrate concentrated. The residue was partitioned between 100 mL of ethyl acetate and 50 mL of water. The organic layer was dried over sodium sulfate, filtered, and concentrated.

Compounds (10) were purified by silica gel column chromatography.

| R' | R | Analytical Data for Compounds (10) |
|---|---|---|
| tBu | 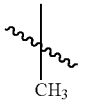 | $^1$H NMR δ (CDCl$_3$): 1.17 (s, 9H, tBu), 1.26-1.32 (d, 3H, CH$_3$), 2.68-2.80 (br. m, 2H, CH$_2$N), 3.32-3.56 (two br. m, 2H, CH$_2$O), 3.72 (s, 3H, CH$_3$O), 3.66-3.82 (m, 1H, CHN), 4.18-4.28 (t, 1H, CH), 4.30-4.46 (d, 2H, CH$_2$), 5.34-5.44 (br. d, 1H, NH), 7.25-7.44 (two m, 4H, fulvene), 7.59-7.64 (d, 2H, fulvene), 7.74-7.79 (d, 2H, fulvene), yield = 57%, $t_R$ = 4.93 min, (M$^+$ + 1) = 455.67. |
| tBu | 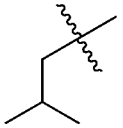 [SMILES: *CC(C)C] | $^1$H NMR δ (CDCl$_3$): 0.88-0.98 (br. t, 6H CH$_3$), 1.21 (s 9H, tBu), 1.26-1.34 (m, 2H, CH$_2$), 1.44-1.54 (m, 1H, CH), 2.58-2.86 (two m, 1H, CH$_2$N), 3.25-3.35 (m, 1H, CH$_2$N), 3.37-3.58 (two m, 2H, CH$_2$O), 3.72-3.80 (br. m, 1H, CHN), 4.14-4.31 (m, 1H, CH), 4.32-4.45 (br. d, 2H, CH$_2$O), 5.34-5.44 (br. d, 1H, NH), 7.30-7.84 (a series of m, 8H, fulvene), yield = 50%, $t_R$ = 5.66 min, (M$^+$ + 1) = 511.67. |
| tBu | 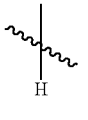 | $^1$H NMR δ (CDCl$_3$): 1.17 (s, 9H, tBu), 2.68-2.78 (m, 1H, CH$_2$N), 2.82-2.92 (m, 1H, CH$_2$N), 3.35-3.55 (m, 4H, CH$_2$N, and CH$_2$O), 3.73 (s, 3H, CH$_3$O), 3.75-3.85 (m, 1H, CHN), 4.20-4.28 (m, 1H, CH), 4.32-4.48 (m, 2H, CH$_2$), 5.40-5.50 (d, 1H, NH), 7.28-7.8 (a series of m, 8H, fulvene), yield = 44%, $t_R$ = 5.02 min, (M$^+$ + 1) = 441.50. |
| tBu | 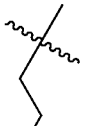 | $^1$H NMR δ (CDCl$_3$): 0.84-0.92 (br. t, 3H, CH$_3$), 1.17 (s, 9H, tBu), 1.28-1.35 (m, 4H, CH$_2$), 1.48-1.84 (two m, 2H, CH$_2$), 2.62-2.82 (m, 2H, CH$_2$N), 3.20-3.33 (m, 1H, CHN), 3.35-3.54 (two m, 2H, CH$_2$O), 3.72 (s, 3H, CH$_3$O), 3.64-3.80 (m, 1H, CHN), 4.20-4.28 (t, 1H, CH), 4.32-4.42 (m, 2H, CH$_2$O), 5.34-5.44 (br. d, 1H, NH), 7.25-7.79 (a series of m, 8H, fulvene), yield = 65%, $t_R$ = 5.85 min, (M$^+$ + 1) = 441.27. |
| Trt |  | $^1$H NMR δ (CDCl$_3$): 2.36-2.63 (br. m, 2H, CH$_2$CO), 2.65-2.90 (br. m, 2H, CH$_2$N), 3.05-3.20 (br. m, 2H, CH$_2$O), 3.50-3.64 (br. m, 1H, CHN), 3.68 & 3.69 (two s, 3H, CH$_3$O), 3.82-3.94 (br. m, 1H, CHN), 4.12-4.21 (br. m, 1H, CH), 4.24-4.43 (br. m, 2H, CH$_2$O), 4.90-4.98 (br. d, 1H, NH), 7.15-7.80 (a series of m, 23H, fulvene and Trt), yield = 39%, $t_R$ = 8.13 min, (M$^+$ + 1) = 926.99. |
| Trt |  | $^1$H NMR δ (CDCl$_3$): 1.68-1.82 (m, 1H, CH$_2$), 1.85-1.99 (m, 1H, CH$_2$), 2.12-2.37 (m, 2H, CH$_2$CO), 2.58-2.96 (a series of four m, 2H, CH$_2$N), 3.08-3.28 (br. m, 2H, CH$_2$O), 3.66 & 3.67 (two s, 3H, CH$_3$O), 3.76-3.89 (br. m, 1H, CHN), 4.15-4.24 (br. m, 1H, CH), 4.28-4.41 (br. d, 2H, CH$_2$O), 5.10-5.22 (br. d, 1/2H, NH), 5.28-5.35 (br. d, 1/2H, NH), 7.15-7.80 (a series of m, 23H, fulvene, and Trt), yield = 43%, $t_R$ = 8.10 min, (M$^+$ + 1) = 940.97. |
| Trt |  | $^1$H NMR δ (CDCl$_3$): 1.43 (s, 6H, CH3), 1.46-1.56 (m, 4H, CH$_2$), 2.06 (s, 3H, CH$_3$), 2.50 (s, 3H, CH$_3$), 2.57 (s, 3H, CH$_3$), 2.75-2.80 (m, 1H, CH$_2$N), 2.91 (s, 2H, CH2), 3.12-3.32 (three br. m, 4H, CH$_2$N), 3.68 (s, 3H, CH$_3$O), 4.13-4.21 (t, 1H, CH), 4.28-4.38 (d, 2H, CH$_2$), 5.12-5.23 (br. d, 1H, NH), 5.80-6.12 (two br. m, 2H, NH), 7.18-7.80 (a series of m, 23H, fulvene, and Trt), yield = 68%, $t_R$ = 7.52 min, (M$^+$ + 1) = 997.91. |

-continued

| R' | R | Analytical Data for Compounds (10) |
|---|---|---|
| Trt | 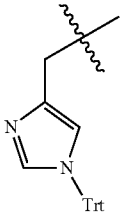 | $^1$H NMR δ (CDCl$_3$): 2.75-2.98 (two m, 2H, CH$_2$N), 3.06-3.18 (m, 1H, CH$_2$N), 3.22-3.33 (m, 1H, CH$_2$N), 3.57 & 3.60 (two s, 3H, CH$_3$O), 3.80-3.92 (m, 1H, CHN), 4.00-4.08 (m, 1H, CH), 4.18-4.30 (br. d, 2H, CH$_2$),7.00-7.80 (a series of m, 25H, fulvene, Trt, and Imidazole), yield = 57%, $t_R$ = 7.59 min, (M$^+$ + 1) = 949.79. |
| Trt | 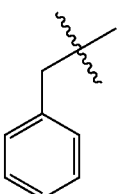 | $^1$H NMR δ (CDCl$_3$): 1.26 & 1.27 (two s, 9H, $^t$Bu), 2.50-2.61 (dd, 1H, CH$_2$—Ph), 2.76-2.86 (m, 2H, CH$_2$—Ph, and CH$_2$N), 2.92-3.20 (m, 1H, CH$_2$N), 2.92-3.20 (m, 2H, CH$_2$O), 3.32-3.46 (m, 1H, CH$_2$O), 3.59 (s, 3H, CH$_2$O), 3.79-3.88 (m, 1H, CHN), 4.18-4.28 (m, 1H, CH), 4.30-4.37 (br. d, 2H, CH$_2$O), 5.18-5.26 (br. d, 1H, NH), 6.80-6.88 (d, 2H, Ph), 6.96-7.02 (d, 2H, Ph), 7.18-7.80 (a series of m, 23H, fulvene, and Trt), yield = 23%. |
| Trt | 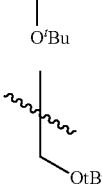 | $^1$H NMR δ (CDCl$_3$): 1.11 (s, 9H, $^t$Bu), 2.54-2.74 (two m, 2H, CH$_2$N), 3.02-3.58 (six m, 6H, CH$_2$O, CH$_2$N, and CHN), 3.70 (s, 3H, CH$_2$O), 3.83-3.93 (m, 1H, CHN), 4.15-4.29 (m 1H, CH), 4.34-4.37 (d, 2H, CH$_2$), 5.46-5.53 (br. d, 1H, NH), 7.18-7.79 (a series of m, 23H, fulvene, and Trt), yield = 45%, (M$^+$ + 1) = 713.42. |
| $^t$Trt | 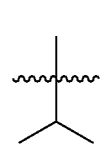 [SMILES: *C(C)C] | $^1$H NMR δ (CDCl$_3$): 0.80-0.92 (m, 7H, CH$_3$), 1.75-1.90 (br. m, 1H, CH), 2.6-4.36 (a series of m, 9H, CH$_2$O, CH$_2$N, CHN), 3.68 (s, 3H, CH$_3$O), 5.5 (d, 0.5H, CH), 7.23-7.77 (m, 24H, fulvene and Trt), yield = 72% (3 steps), $t_R$ = 6.86 min, (M$^+$ + 1) = 669.10. |

Synthesis of 4-Fmoc-6-hydroxymethyl-3-substituted-piperazin-2-one (6): For the preparation of compounds (6) three steps were required: (a) Fmoc deprotection with concomitant cyclization, (b) Fmoc protection, and (c) hydroxyl group deprotection.

Fmoc group removal and cyclization: A solution of 10 mmol of cyclic compound in 30 mL of 30% diethyl amine in ethyl acetate solution was stirred at room temperature overnight, and then concentrated to dryness.

(a) Fmoc protection: To a biphasic solution of 10 mmol of compound in 20 mL of tetrahydrofuran and 10 mL of water, was added 2.52 g (30 mmol) of solid sodium bicarbonate, followed by 3.36 g (13 mmol) of Fmoc-Cl. The mixture was stirred for 3 hours, diluted with ethyl acetate, the layers separated, and the organic layer washed with water, dried over magnesium sulfate, and concentrated.

(b) Hydroxyl group deprotection: For compounds containing a $^t$Bu ether protecting group: The compounds were deprotected with a solution of 90% trifluoroacetic acid in dichloromethane for 1-2 hours, and then concentrated to dryness. The residue was dissolved in ethyl acetate and washed with a saturated solution of sodium bicarbonate, dried over magnesium sulfate, and then concentrated. For compounds containing a Trt ether protecting group: the compounds were deprotected by adding a solution of 1-10% trifluoroacetic acid in dichloromethane containing 2-10% tri-isopropyl silane. The reaction was instantaneous. The solution was then neutralized by pouring it into a saturated solution of sodium bicarbonate. The layers were separated, dried over sodium sulfate, and concentrated.

Compounds (6) were purified by silica gel column chromatography.

| R | Analytical Data for Compounds (6) |
|---|---|
|  | $^1$H NMR δ (CDCl$_3$): 1.17-1.35 (br. m, 3H, CH$_3$), 2.64-2.82 (t, 1H, CH$_2$N), 3.2-3.8 (two br. m, 3H, CH$_2$O, CH$_2$N), 4.18-4.44 (br. t, 1H, CH), 4.64-4.90 (br. d, 2H, CH$_2$O), 6.70-6.86 (br. s, 1H, NH), 7.22-7.82 (a series of m, 8H, fulvene), yield = 72%, $t_R$ = 4.64 min, (M$^+$ + 1) = 367.32. |
|  | $^1$H NMR δ (CDCl$_3$): 0.64-1.02 (m, 6H, CH$_3$), 1.45-1.63 (m, 3H, CH$_2$, and CH), 2.65-2.84 (m, 1H, CH$_2$N), 2.89-3.76 (a series of br. m, 5H, CH$_2$O, and CHN), 4.17-4.28 (br. m, 1H, CH), 4.48-4.82 (three br. m, CH$_2$O, NH, and OH), 6.95-7.82 (a series of br. m, 8H, fulvene), yield = 51%, $t_R$ = 5.43 min, (M$^+$ + 1) = 409.08. |
|  | $^1$H NMR δ (CDCl$_3$): 3.17-3.78 (a series of br. m, 5H, CH$_2$O, CH$_2$N, and CHN), 421-4.27 (t, 1H, CH), 4.42-4.68 (br. peak, 2H, CH$_2$O), 6.62 (br. s, 1H, NH), 7.28-7.81 (a series of m, 8H, fulvene), yield = 67%, $t_R$ = 4.50 min, (M$^+$ + 1) = 353.45. |
|  | $^1$H NMR δ (CDCl$_3$): 0.72-0.90 (br. peak, 3H, CH$_3$), 1.0-1.40 (br. peak, 4H, CH$_2$), 1.48-1.90 (three br. peaks, 2H, CH$_2$), 2.68-2.80 (t, 1H, CH$_2$N), 3.10-3.70 (four br. peaks, 4H, CH$_2$O, CHN, and CH$_2$N), 4.15-4.25 (br. peak, 1H, CH), 4.54-4.62 (br. d, 2H, CH$_2$O), 7.25-7.80 (a series of m, 8H, fulvene), yield = 72%, $t_R$ = 5.77 min, (M$^+$ + 1) = 408.95. |
|  | $^1$H NMR δ (CDCl$_3$): 2.50-3.38 (four overlapping br. m, 7H, CH$_2$—CO, CH$_2$N, CH$_2$O, and CHN), 3.42-3.64 (m, 1/2 H, CHN), 3.70-3.88 (m, 1/2H, CHN), 4.16-4.23 (br. d, 1H, CH), 4.48-4.68 (br. m, 2H, CH$_2$O), 4.94-5.05 (br. d, 1H, NH), 6.95-7.80 (a series of m, 23H, fulvene and Trt), yield = 83%, $t_R$ = 7.04 min, (M$^+$ + 1) = 652.61. |
|  | $^1$H NMR δ (CDCl$_3$): 1.67-1.78 (br. m, 1H, CH$_2$), 1.81-2.0 (br. m, 1H, CH$_2$), 2.10-2.43 (br. m, 2H, CH$_2$—CO), 2.58-2.81 (br. m, 2H, CH$_2$N), 3.02-3.66 (a series of br. m, 4H, CH$_2$O, and CHN), 4.17-4.23 (br. m, 1H, CH), 4.40-4.80 (br. m, 2H, CH$_2$O), 7.15-7.80 (a series of m, 23H, fulvene, and Trt), yield = 80%, $t_R$ = 7.04 min, (M$^+$ + 1) = 666.66. |
|  | $^1$H NMR δ (CDCl$_3$): 1.43 (s, 6H, CH$_3$), 1.50-1.60 (br. m, 4H, CH$_2$), 2.10 (s, 3H, CH$_3$), 2.48 (s, 3H, CH$_3$), 2.55 (s, 3H, CH$_3$), 2.92 (s, 2H, CH$_2$), 3.08-3.47 (two m, 3H, CH$_2$O, and CH$_2$N), 3.57-3.97 (a series of m, 3H, CH$_2$O, and CHN), 4.15-4.25 (br. m, 1H, CH), 4.44-4.74 (br. m, 2H, CH$_2$), 7.20-7.80 (a series of br. m, 8H, fulvene), yield = 91%, $t_R$ = 6.05 min, (M$^+$ + 1) = 704.71. |
|  | $^1$H NMR δ (CDCl$_3$): 2.14-2.56 (two m, 2H, CH$_2$—Im), 2.90-3.90 (a series of m, 4H, CH$_2$N, and CH$_2$O), 4.0-4.74 (a series of m, 4H, CHN, CH, CH$_2$), 7.0-7.80 (a series of multiples, 25H, fulvene, Im, and Trt), yield = 64%, $t_R$ = 5.27 min, (M$^+$ + 1) = 675.08. |

| R | Analytical Data for Compounds (6) |
|---|---|
| *p-OtBu-benzyl* | ¹H NMR δ (CDCl₃): 1.29 (s, 9H, ᵗBu) 2.47-2.74 (a series of m, 2H, CH₂Ph), 2.90-3.04 (m, 1H, CH₂Ph), 3.06-3.45 (three m, 6H, CH₂O, and CH₂N), 3.89-4.29 (three m, 2H, CH, and CHN), 4.32-4.42 (m, 1H, CHN), 4.56-4.66 (m, 2H, CH₂), 6.81-7.80 (a series of m, 12 H, fulvene, and Ph), yield = 71%, (M⁺ + 1) = 515.81. |
| *CH(CH₃)CH₂OtBu* | ¹H NMR δ (CDCl₃): 1.00 & 1.10 (two s, 9H, ᵗBu), 3.0-3.74 (four br. m, 7H, CH₂O, CH₂N, and CHN), 3.86-4.26 (a series of m, 2H, CHN, and CH), 4.42-4.68 (br. d, 2H, CH₂), 7.26-7.80 (a series of br. m, 8H, fulvene), yield = 55%, (M⁺ + 1) = 439.08. |

Synthesis of 4-Fmoc-5-substituted-6-oxo-piperazine-2-carboxylic acid (7): Compounds (7) were prepared as described in method A. Compounds (7) were purified by silica gel column chromatography.

| R | Analytical Data for Compounds (7) |
|---|---|
| CH₃ | ¹H NMR δ (CDCl₃): 1.08-1.20 (br. peak, 1.5H, CH₃), 1.30-1.38 (br. peak, 1.5H, CH₃), 2.86-3.07 (br. m, 1H, CH₂N), 3.83-3.97 (br. m, 1H, CH₂N), 4.18-4.37 (a series of br. peaks, 2H, CH and CHN), 4.40-4.74 (two br. peaks, 3H, CH₂O, and CHN), 7.28-7.82 (a series of m, 8H, fulvene), 8.92-9.10 (br. s, 1H, CO₂H), yield = 51%, $t_R$ = 4.80 min, (M⁺ + 1) = 381.57. |
| *isobutyl* | ¹H NMR δ (CDCl₃): 0.40-1.60 (a series of br. peaks, 9H, CH, CH₂, and CH₃), 2.81-3.09 (br. peak, 1H, CH₂N), 3.68-3.80 (br. peak, 2H, CHN), 3.96-4.32 (br. peak, 2H, CH, and CNH), 4.48-4.68 (br. peak, CH₂O), 7.26-7.84 (a series of m, 8H, fulvene), yield = 50%, $t_R$ = 5.57 min, (M⁺ + 1) = 423.15. |
| H | ¹H NMR δ (CDCl₃): 3.77-3.99 (m, 1H, CHN), 3.90-4.35 (a series of m, 5H, CH₂N, CH), 4.44-4.57 (d, 2H, CH₂), 7.3-7.82 (a series of m, 8H, fulvene), yield = 48%, $t_R$ = 4.58 min, (M⁺ + 1) = 367.30. |
| *sec-butyl* | ¹H NMR δ (CDCl₃): 0.69-1.90 (a series of br. peaks, CH₂, and CH₃), 2.85-3.05 (br. peak, 2H, CH₂N), 3.65-3.95 (two br. peaks, 1H, CHN), 4.00-4.40 (two br. peaks, CH₂N, and CH), 4.41-4.74 (br. peak, 3H, CH₂O, and CHN), 7.20-7.80 (a series of br. m, 8H, fulvene), yield = 70%, $t_R$ = 5.93 min, (M⁺ + 1) = 423.42. |
| *CH₂CH₂C(O)NHTrt* | ¹H NMR δ (CDCl₃): 2.51-3.06 (a series of m, 2H, CH₂—CO), 3.85-4.86 (a series of m, 7H, CH₂N, CHN, CH, and CH₂O), 7.0-7.78 (a series of br. m, 23H, fulvene and Trt), yield = 30%, $t_R$ = 7.04 min, (M⁺ + 1) = 666.79. |

| R | Analytical Data for Compounds (7) |
|---|---|
| *CH₂CH₂CH₂C(O)NHTrt* | ¹H NMR (CDCl₃): 1.74-2.46 (a series of br. m, 4H, CH₂—CO, and CH₂), 3.78-4.06 (two m, 2H, CH₂N), 4.16-4.68 (a series of br. m, 5H, CHN, CH, and CH₂O), 7.14-7.82 (a series of br. m, 23H, fulvene, and Trt), yield = 47%, $t_R$ = 7.11 min, (M⁺ + 1) = 680.33. |
| *arginine Pbf* | ¹H NMR δ (CDCl₃): 1.08-1.60 (a series of br. peaks, 8H, CH₂) and CH₃), 2.12 (s, 3H, CH₃), 2.48 (s, 3H, CH₃), 2.57 (s, 3H, CH₃), 2.92 (s, 2H, CH₃), 3.10-3.25 (br. m, 2H, CH₂N), 3.82-4.28 (a series of br. m, 4H, CH₂N, CHN, CH), 4.40-4.70 (br. m, 3H, CHN, and CH₂O), 7.20-7.80 (a series of br. m, 8H, fulvene), yield = 42%, $t_R$ = 6.15 min, (M⁺ + 1) = 718.69. |
| *p-OtBu-benzyl* | ¹H NMR δ (CDCl₃): 1.28 & 1.34 (two s, 9H, ᵗBu), 2.42-3.64 (a series of br. m, 5H, CH₂N, CHN, and CH₂Ph), 4.0-4.76 (a series of br. m, 4H, CHN, CH, and CH₂O), 6.60-6.96 (br. m, 4H, Ph), 7.20-7.80 (a series of br. m, 8H, fulvene), yield = 67%, (M⁺ + 1) = 529.17. |
| *CH(CH₃)CH₂OtBu* | ¹H NMR δ (CDCl₃): 0.96- & 1.10 (two s, 9H, ᵗBu), 3.04-3.18 (br. m, 0.5H, CH₂N), 3.30-3.94 (four br. m, 3.5H, CH₂N, and CH₂O), 3.98-4.32 (br. m, 2H, CH, and CHN), 4.33-4.74 (two br. m, 3H, CHN, CH₂O), 7.28-7.80 (a series of m, 8H, fulvene), yield = 60%, (M⁺ + 1) = 453.37. |

Method C:

Diphenylmethyl 3-Fmoc-amino-4-(methoxycarbonyl-substituted-methylamino)-butyrates (41) were prepared by reductive amination of diphenylmethyl 3-Fmoc-amino-4-oxo-butyrate (40) with α-amino esters (2), using either sodium cyanoborohydride or sodium triacetoxyborohydride as the reducing agent. The diphenylmethyl 3-Fmoc-amino-4-oxo-butyrate (40) required for the reductive amination was prepared by lithium aluminum hydride reduction of the Weinreb amide derivative (39), which was formed from commercially available Fmoc-aspartic acid α-allyl ester derivative (38) by protection of the β-ester under Mitsunobu conditions. The allyl ester was removed using palladium (0) catalyst, followed by Weinreb amide formation using TBTU as the coupling agent. Diphenylmethyl 3-Fmoc-amino-4-(methoxycarbonyl-substituted-methylamino)-butyrate (41) was then Fmoc deprotected, cyclized, diphenylmethyl ester removed by hydrogenation, followed by Fmoc protection to give the final product (4-Fmoc-5-substituted-6-oxo-piperazin-2-yl)-acetic acid (37).

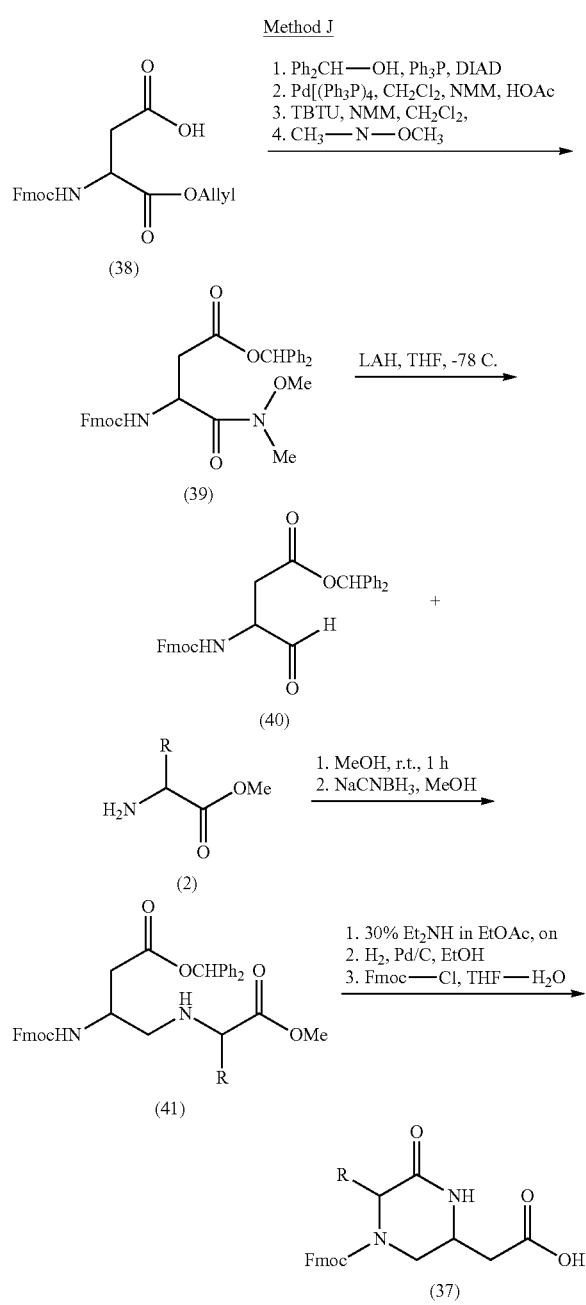

Method J at 37:2:1, containing 1.5 g (1.3 mmol) of tetrakis triphenylphosphine palladium (0), and the solution stirred at room temperature overnight, concentrated to dryness, and partitioned between 100 mL of ethyl acetate and 30 mL of water. The layers were separated, and the organic layer washed with 1×50 mL of water, dried over sodium sulfate, and concentrated. The residue was suspended in 20 mL of dry dichloromethane, and 1.65 mL (15 mmol) of N-methyl morpholine, and 4.07 g (12.7 mmol) of TBTU were added, and the suspension stirred at room temperature for 20 minutes, followed by the addition of 1.65 mL (15 mmol) of N-methyl morpholine, and 1.52 g (15.6 mmol) of N,O-dimethyl hydroxylamine hydrochloride salt. The suspension was stirred at room temperature for 2 hours, concentrated, partitioned between 100 mL of ethyl acetate and 50 mL of water. The organic layer was washed with 1×30 mL of water, 1×30 mL of saturated sodium bicarbonate solution, and 1×30 mL of 1N hydrochloric acid solution, dried over sodium sulfate, and concentrated. The product was purified by silica gel column chromatography. $^1$H NMR δ (CDCl$_3$) 2.76-2.88 (dd, 1H, CH$_2$CO), 2.89-3.00 (dd, 1H, CH$_2$CO), 3.16 (s, 3H, CH$_3$N), 3.70 (s, 3H, CH$_3$O), 4.14-4.22 (dd, 1H, CH), 4.28-4.40 (t, 2H, CH$_2$), 5.07-5.16 (dd, 1H, CHN), 5.69-5.76 (d, 1H, CHO), 7.24-7.8 (a series of m, 18H, fulvene, and Ph); HPLC t$_R$=7.08, (M$^+$+Na$^+$)=587.03.

Synthesis of Diphenylmethyl 3-Fmoc-amino-4-oxo-butyrate (40): Compound (40) is prepared using a procedure similar to the one described for compound (9).

Synthesis of Diphenylmethyl 3-Fmoc-amino-4-(methoxy-carbonyl-substituted-methylamino)-butyrate (41): Compounds (41) were prepared using a procedure similar to the one described for compound (10), but using compound (40) as the aldehyde.

| R | Analytical Data for Compounds (41) |
|---|---|
| ![structure with HN, =NH, NHPbf] | $^1$H NMR δ (CDCl$_3$) 1.2-1.7 (m, 4H, CH$_2$), 1.42 (s, 3H, CH$_3$Ph), 1.60 (s, 6H, CH$_3$Ph), 2.07 (s, 2H, CH$_2$), 2.52 (s, 3H, CH$_3$Ph), 2.58 (s, 3H, CH$_3$—Ph), 2.08-2.80 (a series of m, 2H, CH$_2$CO), 3.0-3.2 (m, 2H, CH$_2$N), 3.64 (s, 3H, CH$_3$O), 3.96-4.10 (m, 1H, CHN), 4.20-4.28 (m, 1H, CH), 4.28-4.40 (br. m, 2H, CH$_2$), 5.82-6.18 (m, 1H, CHO), 7.24-7.80 (a series of m, 18H, fulvene, and Ph), HPLC t$_R$ = 6.53, (M$^+$ + 1) = 930.56. |

Synthesis of Fmoc-Asp-(OCHPh$_2$) Weinreb amide (39): To a solution of 5.1 g (13.0 mmol) of Fmoc-aspartic acid α-allyl ester (38) in 30 mL of dry tetrahydrofuran, containing 3.4 g (13 mmol) of triphenylphosphine, and 2.41 g (13.1 mmol) of diphenylmethanol, kept at 0° C. under nitrogen, was added slowly 2.6 mL (13.4 mmol) of diisopropyl azodicarboxylate. The ice bath was removed, and the reaction stirred at room temperature overnight, concentrated to dryness, and then purified by silica gel column chromatography. $^1$H NMR δ (CDCl$_3$) 2.96-3.06 (dd, 1H, CH$_2$CO), 3.15-3.26 (dd, 1H, CH$_2$CO), 4.18-4.76 (a series of m, 3H, CH, CH$_2$), 5.14-5.32 (m, 1H, CHN), 5.76-5.86 (m, 1H, CHO), 7.20-7.80 (a series of m, 18H, fulvene, and Ph); HPLC t$_R$=7.68 min, (M$^+$+Na$^+$)= 583.90.

The product (9.8 mmol) was then dissolved in 40 mL of a dichloromethane:acetic acid: N-methyl morpholine solution Synthesis of (4-Fmoc-5-substituted-6-oxo-piperazin-2-yl)-acetic acid (37): A solution of 10 mmol of compound (41) in 30 mL of 30% diethylamine in ethyl acetate was stirred at room temperature for 3 hours. The solution was then concentrated to dryness, redissolved in 2×30 mL of ethyl acetate, and reconcentrated. The residue dissolved in 50 mL of ethanol, and 20 mL of 1N hydrochloric acid solution, and hydrogenated at room temperature and atmospheric pressure overnight, filtered through celite, and concentrated to dryness. The residue was dissolved in 20 mL of tetrahydrofuran, and 10 mL of water, and 2.52 g (30 mmol) of solid sodium bicarbonate was added, followed by the addition of 3.3 g (13 mmol) of Fmoc-Cl. The mixture was stirred for 3 hours, diluted with 100 mL of ethyl acetate, the layers separated, and the organic layer washed with 2×50 mL of water, dried over magnesium sulfate, and concentrated. The product was purified by silica gel column chromatography.

| R | Analytical Data for Compounds (37) |
|---|---|
| 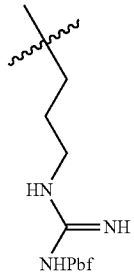 | $^1$H NMR δ (CDCl$_3$) 1.2-1.6 (m, and s, 7H, CH$_2$, CH$_3$Ph), 2.10 (s, 2H, CH$_2$), 2.46 (s, 3H, CH$_3$—Ph), 2.56 (s, 3H, CH$_3$—Ph), 2.46-2.63 (br. m, 2H, CH$_2$CO), 3.0-3.95 (3 br. m, 5H, CH$_2$N, CHN), 4.10-4.30 (br. m, 1H, CH), 4.40-4.80 (br. m, 3H, CHN, CH$_2$), 7.22-7.80 (a series of m, 8H, fulvene), HPLC t$_R$ = 5.73, (M$^+$ + 1) 732.24. |

Synthesis of Constructs of the Invention

The constructs as disclosed in the several embodiments of this invention may be readily synthesized by any known conventional procedure for the formation of a peptide linkage between amino acids. Such conventional procedures include, for example, any solution phase procedure permitting a condensation between the free alpha amino group of an amino acid residue having its carboxyl group or other reactive groups protected and the free primary carboxyl group of another amino acid residue having its amino group or other reactive groups protected. In a preferred conventional procedure, the constructs of this invention may be synthesized by solid-phase synthesis and purified according to methods known in the art. The amino acid surrogates of the present invention may be incorporated into constructs of this invention by methods substantially similar to or identical to those employed with residues. Any of a number of well-known procedures utilizing a variety of resins and reagents may be used to prepare the constructs of this invention.

The process for synthesizing the constructs may be carried out by a procedure whereby each amino acid or amino acid surrogate in the desired sequence is added one at a time in succession to another amino acid residue or amino acid surrogate or by a procedure whereby peptide fragments with the desired amino acid sequence, which may include one or more amino acid surrogates, are first synthesized conventionally and then condensed to provide the desired construct. The resulting construct is cyclized to yield a cyclic construct of the invention.

Solid phase peptide synthesis methods are well known and practiced in the art. In such methods the synthesis of constructs of the invention can be carried out by sequentially incorporating the desired amino acid residues or amino acid surrogates one at a time into the growing peptide chain according to the general principles of solid phase methods. These methods are disclosed in numerous references, including Merrifield R. B., Solid phase synthesis (Nobel lecture). *Angew. Chem.* 24:799-810 (1985) and Barany et al., *The Peptides, Analysis, Synthesis and Biology*, Vol. 2, Gross E. and Meienhofer J., Eds. Academic Press, 1-284 (1980).

In chemical syntheses of constructs, reactive side chain groups of the various amino acid residues or amino acid surrogates are protected with suitable protecting groups, which prevent a chemical reaction from occurring at that site until the protecting group is removed. Also common is the protection of the alpha amino group of an amino acid residue or amino acid surrogate while that entity reacts at the carboxyl group, followed by the selective removal of the alpha amino protecting group to allow a subsequent reaction to take place at that site. Specific protecting groups have been disclosed and are known in solid phase synthesis methods and solution phase synthesis methods.

Alpha amino groups may be protected by a suitable protecting group, including a urethane-type protecting group, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz); aliphatic urethane-type protecting groups, such as t-butyloxycarbonyl (Boc), diisopropylmethoxycarbonyl, isopropoxycarbonyl, and allyloxycarbonyl. Fmoc is preferred for alpha amino protection.

Guanidino groups may be protected by a suitable protecting group, such as nitro, p-toluenesulfonyl (Tos), Z, pentamethylchromanesulfonyl (Pmc), adamantyloxycarbonyl, pentamethyldihydrobenzofuran-5-sulfonyl (Pbf), Fmoc and Boc. Pbf is one preferred protecting group for Arg. Other preferred protecting groups include Z, Fmoc, and Boc. It is to be understood that particularly guanidino protecting groups may be cleaved and removed during the synthetic process, or may alternatively not be cleaved or removed, in which event the side chain with the protecting group forms a derivative of an amino acid side chain moiety as defined herein. Particularly where the protecting group is labile, and may be removed by some mechanism in vivo upon administration to a patient, the construct becomes a "prodrug", which is to say a construct that is a drug precursor which, following administration to a patient, is converted to the desired drug form in vivo via some chemical or physiological process (e.g., a prodrug on being brought to physiological pH or through enzyme action is converted to the desired drug form).

The constructs of the invention described herein can be prepared using solid phase synthesis, either manually or by means of an automated peptide synthesizer, using programming modules as provided by the manufacturer and following the protocols set forth by the manufacturer, or by modifications of the manufacturers's protocols to improve the yield of difficult couplings.

Solid phase synthesis is commenced from the C-terminal end of the construct by coupling a protected α-amino acid, α-amino acid surrogate or α-amino alcohol mimetic to a suitable resin. Such starting material is prepared by attaching an α-amino-protected amino acid or α-amino-protected amino acid surrogate by an ester linkage to a p-benzyloxybenzyl alcohol (Wang) resin or a 2-chlorotrityl chloride resin, by an amide bond between an Fmoc-Linker, such as p-[(R, S)-α-[1-(9H-fluor-en-9-yl)-methoxyformamido]-2,4-dimethyloxybenzyl]-phenoxyacetic acid (Rink linker) to a benzhydrylamine (BHA) resin, or by other means well known in the art, such as by attaching an α-amino-protected alcohol mimetic to 3,4-dihydro-2H-pyran-2yl-methanol linker attached to chloromethyl polystyrene resin. Fmoc-Linker-BHA resin supports are commercially available and generally used when feasible. The resins are carried through repetitive cycles as necessary to add amino acids sequentially. The alpha amino Fmoc protecting groups are removed under basic conditions. Piperidine, piperazine, diethylamine, or morpholine (20-40% v/v) in N,N-dimethylformamide (DMF) may be used for this purpose.

Following removal of the alpha amino protecting group, the subsequent protected amino acids or amino acid surrogates are coupled stepwise in the desired order to obtain an intermediate, protected peptide-resin. The activating reagents used for coupling of the amino acids in the solid phase synthesis of the peptides are well known in the art. After the construct is synthesized, if desired, the orthogonally protected side chain protecting groups may be removed using methods well known in the art for further derivatization of the construct.

Reactive groups in a construct can be selectively modified, either during solid phase synthesis or after removal from the resin. For example, constructs can be modified to obtain N-terminus modifications, such as acetylation, while on resin, or may be removed from the resin by use of a cleaving reagent and then modified. Methods for N-terminus modification, such as acetylation, or C-terminus modification, such as amidation or introduction of an N-acetyl group, are known in the art. Similarly, methods for modifying side chains of amino acids are well known to those skilled in the art of peptide synthesis. The choice of modifications made to reactive groups present on the construct will be determined, in part, by the characteristics that are desired in the construct.

The construct are, in one embodiment, cyclized prior to cleavage from the resin. For cyclization through reactive side chain moieties, the desired side chains are deprotected, and the construct suspended in a suitable solvent and a cyclic coupling agent added. Suitable solvents include, for example DMF, dichloromethane (DCM) or 1-methyl-2-pyrrolidone (NMP). Suitable cyclic coupling reagents include, for example, 2-(1H-benzotriazol-1-yl)-1,1,3,3-tetramethyluronium tetrafluoroborate (TBTU), 2-(1H-benzotriazol-1-yl)-1,1,3,3-tetramethyluronium hexafluorophosphate (HBTU), benzotriazole-1-yl-oxy-tris(dimethylamino)phosphonium-hexafluorophosphate (BOP), benzotriazole-1-yl-oxy-tris(pyrrolidino)phosphoniumhexafluorophosphate (PyBOP), 2-(7-aza-1H-benzotriazol-1-yl-1,1,3,3-tetramethyluronium tetrafluoroborate (TATU), 2-(2-oxo-1(2H)-pyridyl)-1,1,3,3-tetramethyluronium tetrafluoroborate (TPTU) or N,N'-dicyclohexylcarbodiimide/1-hydroxybenzotriazole (DCCI/HOBt). Coupling is conventionally initiated by use of a suitable base, such as N,N-diisopropylethylamine (DIPEA), sym-collidine or N-methylmorpholine (NMM).

Following cleavage of constructs from the solid phase following synthesis, the construct can be purified by any number of methods, such as reverse phase high performance liquid chromatography (RP-HPLC), using a suitable column, such as a $C_{18}$ column. Other methods of separation or purification, such as methods based on the size or charge of the construct, can also be employed. Once purified, the construct can be characterized by any number of methods, such as high performance liquid chromatograph (HPLC), amino acid analysis, mass spectrometry, and the like.

Constructs of the present invention with a substituted amide derivative C-terminus, typically an N-alkyl group, are prepared by solid phase synthesis commenced from the C-terminal end of the construct by coupling a protected alpha amino acid or amino acid surrogate to a suitable resin. Such methods for preparing substituted amide derivatives on solid phase have been described in the art. See, for example, Barn D. R., Morphy J. R., Rees D. C. Synthesis of an array of amides by aluminum chloride assisted cleavage of resin-bound esters. *Tetrahedron Lett.* 37, 3213-3216 (1996); DeGrado W. F. Kaiser E. T. Solid-phase synthesis of protected peptides on a polymer bound oxime: Preparation of segments comprising the sequences of a cytotoxic 26-peptide analogue. *J. Org. Chem.* 47:3258-3261 (1982). Such starting material can be prepared by attaching an alpha amino-protected amino acid or amino acid surrogate by an ester linkage to a p-benzyloxybenzyl alcohol (Wang) resin by well known means. The peptide chain is grown with the desired sequence of amino acids or amino acid surrogates, the product cyclized and resin-treated with a solution of appropriate amine and aluminum choride (such as methyl amine, dimethyl amine, ethylamine, and so on) in dichloromethane. The resulting amide derivative construct is released in solution from the resin. The resin is filtered and the amide derivative construct recovered by concentration of solvent followed by precipitation with ether. The crude construct is dried and remaining amino acid side chain protective groups cleaved using trifluoroacetic acid (TFA) in the presence of water and triisopropylsilane (TIS). The final product is precipitated by adding cold ether and collected by filtration. Final purification is by RP-HPLC using a $C_{18}$ column.

In one preferred method, the constructs of formula III are synthesized by the following methods. Each of the constructs has one or two amino acid surrogates based on a keto-piperazine structure. The amino acid surrogates are synthesized as described above. The constructs are synthesized using Fmoc chemistry. A manual synthetic approach is used for couplings immediately before and after incorporation of the keto-piperazine amino acid surrogate.

The following protocol was employed to attach an amino acid surrogate to resin, such as where the amino acid surrogate was in a terminal position. Rink amide resin (loading at 0.3 mmol/g, Advanced ChemTech) was allowed to swell in DMF for 30 minutes. Fmoc deprotection of the resin was accomplished using 20% piperidine/DMF for 20 minutes. Coupling of the resin with the selected Fmoc-protected keto-piperazine amino acid surrogate (2 eq) was accomplished by overnight incubation in DMF with PyBop (2 eq) and DIEA (4 eq). If following Kaiser testing a positive result was obtained, the coupling reaction was conducting a second time. Acetylation was carried out using $Ac_2O$ (10 eq) and pyridine (20 eq) in DMF.

The following protocol was employed to attach a keto-piperazine amino acid surrogate to peptide-resin. Coupling was carried out by mixing Fmoc-protected keto piperzine amino acid surrogate (2 eq), TBTU (2 eq) and DIEA (4 eq) in DMF and allowing to incubate overnight, again with a repeat of the coupling reaction if a positive Kaiser test obtained. Acetylation was carried out using $Ac_2O$ (10 eq) and pyridine (20 eq) in DMF.

The following protocol was employed to couple an Fmoc-protected amino acid to a keto-piperazine amino acid surrogate on solid phase. In most instances at least two coupling cycles were needed, and frequently three cycles were employed. In a typical cycle Fmoc-protected amino acid (4 eq) was mixed with HOAt (4 eq) and DIC (4 eq) in DMF. The resulting mixture was then mixed overnight in a SPE tube with a keto-piperazine amino acid surrogate attached directly or through intermediates to resin.

Couplings between amino acids that were not directly adjacent to a keto-piperazine amino acid surrogate in the sequence were conducted using standard protocols for solid phase peptide synthesis. The following protecting groups were employed: Boc for Lys and Orn, t-Butyl for Tyr and Ser, Trityl for Cys and His, O-t-Butyl for Asp and Pbf for Arg.

Constructs were cleaved from resin employing a mixture of TFA/thioanisole/phenol/$H_2O$/DTT/TIS (87.5/2.5/2.5/5/2.5/11) (5 mL) for 3 hours. The resulting material was filtered and precipitated from cold ether under freezing conditions for one hour. Precipitated cysteinyl peptide was washed with cold ether at least three times before being use in an oxidation step.

For cyclization to form disulfide bonds via air oxidation, crude cysteinyl construct was dissolved in a mixture of acetonitrile and water. The pH of the reaction mixture was adjusted to 7-8 using 5% $NH_4OH$. The resulted solution was stirred slowly with 150 mg granular activated carbon for 2 days. Completion of cyclization was confirmed by LC-MS analysis before proceeding to the next process step. After cyclization, solid carbon was filtered from solution. The filtrate was lyophilized or dried in a speed-vac to obtain crude cyclic construct.

Certain constructs of the invention, where the surrogate is bound to resin or other peptide solid support and is at the C-terminal position, may be synthesized by means of the following scheme. The following scheme is exemplified by synthesis of the construct of formula IV, but it is to be understood that substantially similar methods may be employed for any construct wherein the surrogate is bound to resin or other peptide solid support.

A solution of 21.5 g (MW=717, 30 mmol) of Fmoc-protected surrogate (7) in 160 mL of dimethylformamide was added to the deprotected Sieber amide resin as prepared above, followed by 15.6 g (MW=520.3, 30 mmol) of solid PyBop, and 10.4 mL (MW=129.25, d=0.742, 60 mmol) of diisopropylethylamine, followed by another 40 mL of dimethylformamide. The mixture was agitated overnight with nitrogen bubbling. The resin was filtered, and washed with

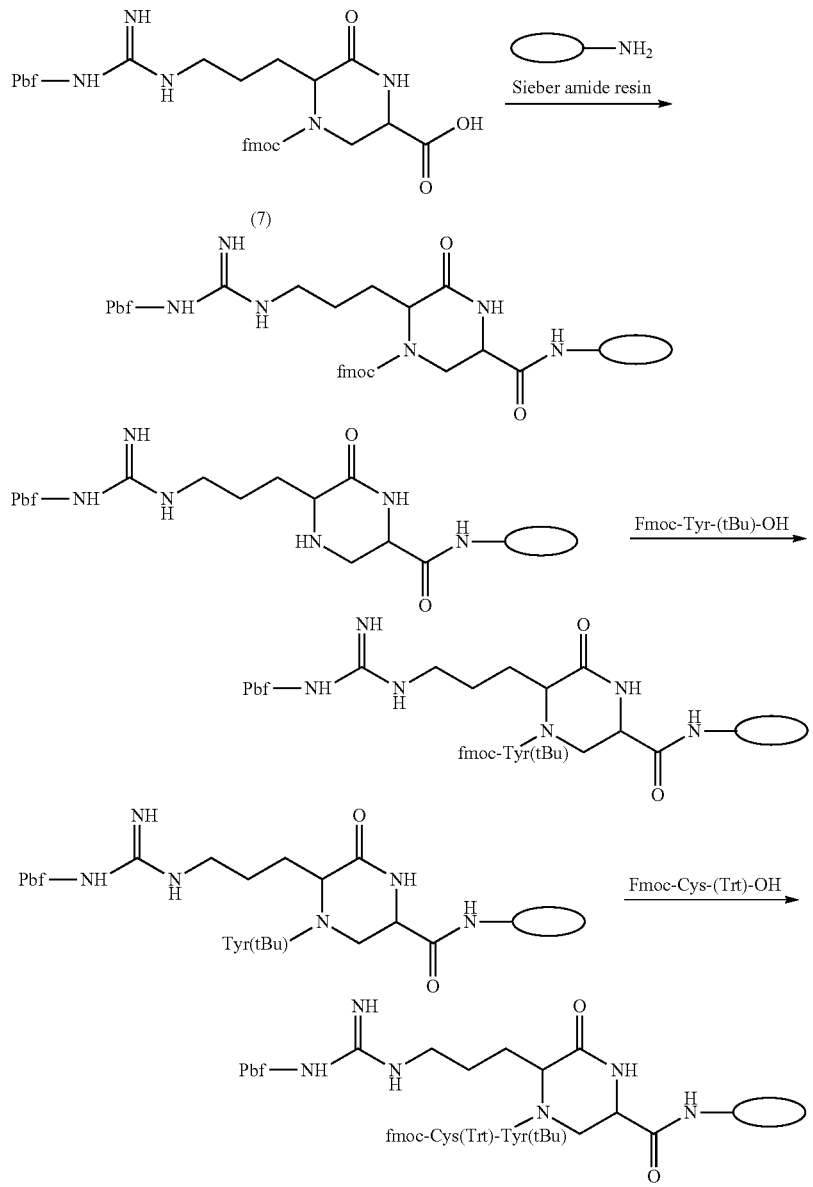

Surrogate (7) is prepared by the scheme of method A above, or any alternative method. Fmoc protected Sieber amide resin was treated by swelling 23.8 g (0.63 mmol/g substitution, 15 mmol) of the resin in 200 mL of a 1:1 mixture of dimethylformamide and dichloromethane for 45 minutes, followed by filtering and washing with 2×125 mL of dimethylformamide. The washed resin was then deprotected with 2×125 mL of 20% piperidine in dimethylformamide for 15 minutes, filtered, and washed with 4×125 mL of dimethylformamide.

4×130 mL of dimethylformamide, capped with 150 mL of capping solution consisting of a 3:2:1 solution of dimethylformamide:acetic anhydride:pyridine for 30 minutes, filtered, and washed with 4×130 mL of dimethylformamide to provide surrogate (7) complexed to resin.

The resulting Fmoc-protected surrogate (7) complexed to resin was deprotected with 2×130 mL of 20% piperidine in dimethylformamide for 15 minutes, filtered, and washed with 4×130 mL of dimethylformamide to yield surrogate (7) complexed to resin. A solution of 27.6 g of Fmoc-Tyr-(tBu)-OH (60 mmol, 4 eq.) in dimethylformamide (200 mL) was added to surrogate (7) complexed to resin, followed by a solution of 24.8 g of HCTU (60 mmol, 4 eq.), and 20.8 mL (120 mmol, 8 eq.) of diisopropylethylamine in DMF to a final volume of 200 mL and coupled overnight with nitrogen bubbling. The resulting Fmoc-Tyr-(tBu)-surrogate (7)-resin was isolated by filtration and washed with 2×130 mL of dimethylformamide.

methanol, 4×130 mL of diethyl ether, and dried under vacuum to give product. The weight increase was quantitative.

100 mL of cleavage reagent consisting of a 81.5:5:5:5:2.5:1 solution of trifluoroacetic acid:phenol:thioanisole:water:DDT:triisopropyl silane was added to 32 g (~6.4 mmol) of the following linear construct:

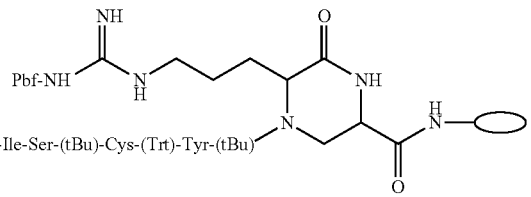
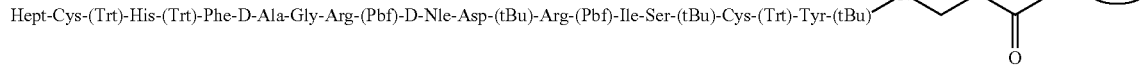

In order to ensure complete coupling, the product was again treated with a solution of 27.6 g of Fmoc-Tyr-(tBu)-OH (MW=459.6, 60 mmol, 4 eq.) in dimethylformamide to a final volume of 200 mL followed by a solution of 24.8 g of HCTU (60 mmol, 4 eq.), and diisopropylethylamine (20.8 mL, 120 mmol, 8 eq.) in DMF to a final volume of 200 mL and coupled overnight with nitrogen bubbling. The resin was filtered, and washed with 2×130 mL of dimethylformamide. HPLC and LC/MS showed that coupling between surrogate (7)-resin and Fmoc-Tyr-(tBu)-OH was complete.

The resulting Fmoc-Tyr-(tBu)-surrogate (7)-resin was then capped with 150 mL of capping solution as above for 30 minutes. The resin was then filtered, washed with 4×130 mL of dimethylformamide, 4×130 mL of dichloromethane, 2×130 mL of MeOH, 2×130 mL of diethyl ether, and dried under vacuum to give 36.7 g.

Thereafter each succeeding amino acid may be coupled. Before the coupling of the first amino acid, resulting Fmoc-Tyr-(tBu)-surrogate (7)-resin was swollen for 45 minutes with 200 mL of a 1:1 solution of dimethylformamide:dichloromethane. Each amino acid (Fmoc-AA-OH) was coupled by repeating the following cycle. The terminal amino acid residue was deprotected with 2×125 mL of 20% piperidine in dimethylformamide for 15 minutes, filtered and washed with 4×125 mL of dimethylformamide. The beads were checked by ninhydrin test. A solution of Fmoc-AA-OH (60 mmol, 4 eq.) in dimethylformamide to a final volume of 200 mL was added to resin, followed by a solution of HBTU (60 mmol, 4 eq.), and (120 mmol, 8 eq.) of N-methylmorpholine in DMF to a final volume of 200 mL [concentration of Fmoc-AA-OH=150 mM solution] and coupled for 30 minutes with nitrogen bubbling (coupling reaction checked by ninhydrin test). When the ninhydrin test was negative, the resin was filtered, and washed with 4×130 mL of dimethylformamide. After all amino acids had been coupled, the resin was washed with 4×130 mL of dichloromethane, 4×130 mL of The suspension was allowed to stand at room temperature for 5 minutes and then filtered. Another 100 mL of cleavage reagent was added to the resin, allowed to stand for 5 minutes, and filtered. This process was repeated.

The resulting resin was then washed with 2×40 mL of trifluoroacetic acid. The filtrates were combined and stirred for 2.5 hours at room temperature, and then concentrated under reduced pressure to ~100 mL volume. Cold diethyl ether (1.5 L, pre-cooled to −20° C.) was added to the filtrate, and then placed in the freezer (−20° C.) for 1 hour, filtered through a sintered glass funnel, and the solids washed with 3×200 mL of cold diethyl ether, and then dried under vacuum for 1 hour with the solids triturated every 15 minutes to make sure solvent was removed efficiently. The following construct was obtained (15.4 g) (103% overall crude yield):

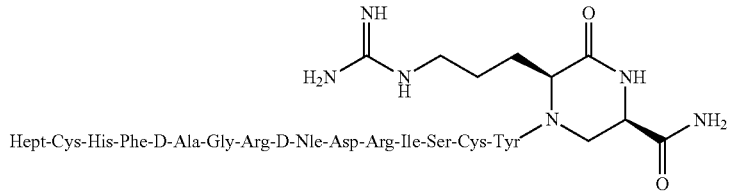

The above construct (15.4 g, 6.4 mmol) was dissolved in 16 L of 30% acetonitrile in water. The pH was adjusted to 8.4 using a solution of 5% ammonium hydroxide. Pulverized activated carbon (15.4 g) was added, and the suspension stirred overnight. The carbon was removed by filtration through celite. The celite was washed 3×100 mL 50% acetonitrile in water. The filtrates were combined, diluted with water to a final concentration of 10% acetonitrile, and loaded in the column for purification. Purification of the trifluoroacetate salt of the resulting construct was performed under the following conditions:

Column: Luna $C_{18}$, 10μ, 50×33 mm
Flow: 70 mL/minute
Solvent A: water containing 0.1% trifluoroacetic acid
Solvent B: acetonitrile containing 0.1% trifluoroacetic acid
Gradient: 5% solvent B for 5 minutes
26% B to 52% B in 30 minutes The pure fractions were combined and lyophilized to give the purified trifluoroacetate salt of the construct. Dowex SBR, LCNG-OH resin (450 g) was suspended in 2 L of water, and gently stirred for 15 minutes, allowed to stand for 15 minutes, and then decanted. The procedure was repeated, and then 0.5 L of water added, and the slurry transferred into a 6×60 cm column. The water was drained, washed with 4 L of water, and ions exchanged with 6.5 L of 20% acetic acid solution. The resin was allowed to stand at room temperature overnight, and then washed with water until the pH of the filtrate was ~4 (8 L of water used). The trifluoroacetate salt of the above construct (11.1 g), as prepared above, was dissolved in 80 mL of water, and loaded to the ion exchange resin, and eluted with water. Fractions containing 79-1 were combined, and 20% acetic acid solution was added to adjust the final concentration to 5% acetic acid, and then lyophilized. The construct of formula IV (10.4 g) was obtained:

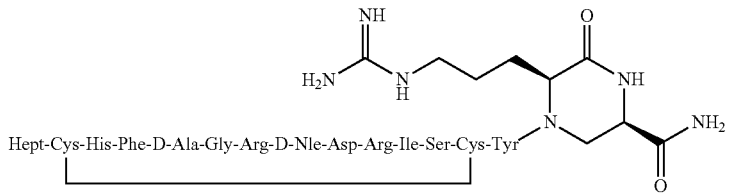

Similar methods may be employed with any construct where the surrogate is bound to resin or other peptide solid support and is at the C-terminal position.

Optional PEGylation of the peptide constructs of the invention may be performed in any manner, such as those described below.

PEGylation of reactive amine groups, such as lysine or ornithine side chains, an omega amino aliphatic in position $Aaa^1$, or an amine group in J of an amino acid surrogate at $Aaa^{15}$, was accomplished by dissolving 0.005 mmol purified construct in 2 mL of dimethylsulfoxide, followed by the addition of 55.5 mg (0.011 mmol, 2 eq) of PEG-5K-OSu (5,000 Da MW methoxy-PEG with a succinimidyl propionate reactive group), with 17.7 µL (0.13 mmol, 20 eq.) of triethyl amine then added, and the slightly cloudy solution stirred at room temperature for 3 hours. Excess PEG-5K-OSu was quenched by the addition of 7 µL (0.111 mmol, 10 eq.) of ethanol amine, and the reaction stirred overnight.

PEGylation of reactive carboxyl groups, such as Asp or Glu side chains or a terminal carboxyl at $Aaa^{15}$ on either a residue or surrogate, is accomplished by coupling PEG-NH$_2$ (PEG-amine), to the construct containing a carboxylate group in the side chain of Asp or Glu or at the C-terminus. The peptide construct (0.005 mmol) is dissolved in DMSO (2 mL), followed by the addition of 55.5 mg (0.011 mmol, 2 eq) of PEG-NH$_2$ and HOBt (0.01 mmol). The coupling is started by the addition of 0.0055 mmole of coupling reagent N-ethyl-N'-(3-dimethylaminopropyl)-carbodiimide (EDAC). The slightly cloudy solution stirred at room temperature overnight. The PEGylated peptide construct is then purified by HPLC.

PEGylation of reactive thiol groups, such as Cys or Hcys side chains or a thiol group in Q of an amino acid surrogate at $Aaa^1$, is accomplished by treating the peptide construct in DMSO with PEG-methyl-maleimide reagent (SunBio, Orinda, Calif.) overnight. The PEGylated peptide construct is then purified by HPLC.

Following PEGylation, the resulting crude mixture was then purified by HPLC, yielding a PEG derivatized construct including one or more amino acid surrogates.

In Vitro and In Vivo Test Systems

Selected constructs were tested in assays to determine binding and functional status. The following assays were employed.

Cell Culture.

A cDNA clone that encodes for human natriuratic peptide receptor A (NPRA) was purchased from Bio S&T Inc. (Montreal, Quebec). The cDNA clone was inserted into the mammalian expression vector pcDNA3.1 (Invitrogen) and transfected into HEK-293 cells. Stable clones were selected by culture of cells in the presence of G418 sulfate. Expression of NPRA was examined by binding of [$^{125}$I]-atrial natriuretic peptide ([$^{125}$I]-ANP) to membrane homogenates prepared from clonal cell lines. HEK-hNPRA cells were maintained in culture at 37° C. in 5% $CO_2$ in Dulbecco's Modified Eagle's Medium (DMEM) supplemented with 10% FBS, G418 sulfate (300 μg/mL) sodium glutamate (0.29 mg/mL), penicillin (100 units/mL) and streptromycin (100 ug/mL).

Competitive Binding Assay.

A competitive inhibition binding assay was performed using crude membrane homogenates prepared from HEK-hNPRA cells. To prepare membrane homogenates, cells were rinsed with phosphate-buffered saline and incubated for 15 minutes at 4° C. in hypotonic lysis buffer (10 mM Tris, pH 7.4+5 mM EDTA). Cells were transferred from plates to polypropylene tubes and homogenized. Homogenates were centrifuged at 25,000×g for 20 minutes. Pellets were resuspended in buffer consisting of 50 mM Tris (pH 7.4) and 1 mM EDTA, homogenized and centrifuged at 25,000×g for 20 minutes. Pellets were resuspended in buffer consisting of 100 mM Tris (pH 7.4) and 10 mM $MgCl_2$ and stored at −80° C. until needed. On the day of an assay, homogenates were thawed and homogenized. Binding of [$^{125}$I]-ANP was carried out in buffer containing 25 mM Hepes (pH 7.4), 100 mM NaCl, 2 mM $CaCl_2$, 5 mM $MgCl_2$, 0.1% BSA and 1 mM 1,10-phenanthroline. Homogenates (1-10 μg protein/well) were incubated with [$^{125}$I]-ANP (25-30 pM) and increasing concentrations of competing ligands in Millipore filter plates for 120 minutes at 4° C. Assays were stopped by addition of cold wash buffer (phosphate-buffered saline) followed by filtration using a vacuum manifold. Bound radioactivity was determined using a gamma counter. Non-specific binding was defined by binding of [$I^{125}$]-hANP to non-transfected HEK293 membranes. Data were analyzed using GraphPad Prism® curve-fitting software.

General Method for Determination of $EC_{50}$.

Functional evaluation of constructs was performed by measuring the accumulation of intracellular cGMP in HEK-293 cells that express recombinant hNPR-A. HEK-NPRA cells were harvested by washing and centrifugation in Cell Dissociation Buffer (Gibco, Life Technologies). Pelleted cells were resuspended in Hank's Balanced Salt Solution (HBSS) containing 10 mM Hepes (pH 7.4), 5 mM $MgCl_2$, 200 mM L-glutamine, 1 mM 1,10-phenanthroline and BSA (0.5 mg/mL). Following centrifugation, cells were resuspended in the above buffer supplemented with 0.5 mM 3-isobutyl-1-methylxanthine (IBMX). Cells (~2×$10^5$/well) were added to each well of a 96-well plate and incubated for 15 minutes at 37° C. Following the pre-incubation period, cells were incubated for an additional 15 minutes in the presence of increasing concentrations of constructs. The reaction was terminated by lysis of the cells with temperature shock. The reaction plate was incubated in a dry ice/ethanol bath for 15 minutes followed by incubation at 90° C. for 10 minutes. Accumulation of cGMP was measured using the cGMP Flashplate RIA (Perkin-Elmer). Data analysis and $EC_{50}$ values were determined by using nonlinear regression analysis with GraphPad Prism® software.

Determination of Mass and Nuclear Magnetic Resonance Analysis.

The mass values of PEG-conjugated constructs were analyzed by MALDI-TOF mass spectrometry (positive ion mode) using alpha-cyano-4-hydroxycinnamic acid (CHCA) as matrix. Methanol was used for sample preparation in construct to matrix ratios of 1:10, 1:20 and 1:30. Alternatively other matrices such as, sinapinic acid (SA) and 2, 5-dihydroxybenzoic acid (DHB), and solvents such acetonitrile—0.1% aqueous TFA can be used for sample preparation. Other determinations of mass values were made using a Waters MicroMass ZQ device utilizing a positive mode. For constructs that were not PEGylated, mass determinations were compared with calculated values and expressed in the form of mass weight plus two divided by two ((M+2)/2), unless otherwise specified.

Proton NMR data was obtained using a Bruker 300 MHz spectrometer. The spectra were obtained after dissolving constructs in a deuteriated solvent such as chloroform, DMSO, or methanol as appropriate.

HPLC measurements were made using a Waters Alliance HT with a YMC Pack Pro $C_{18}$ column (4.6×50 mm, 3µ) eluted at 1 mL/minute in a step-wise procedure. Solvent A (water containing 0.1% trifluoroacetic acid v/v) and solvent B (acetonitrile containing 0.1% trifluoroacetic acid v/v) were used as mobile phases. For analysis of keto piperazine intermediates, the column was equilibrated with 10% B and then B was increased to 90% over a period of 8 minutes. For analysis of peptides, the column was equilibrated with 2% B and then B was increased to 90% over a period of 8 minutes.

EXAMPLE 1

The construct of formula IV having the following structure was synthesized as described above:

EXAMPLE 2

A formulation of the construct of formula IV was made for pharmaceutical use. The construct of formula IV was used in the acetate salt form. The formulation was dispensed into a vial which was stoppered and sealed, with each vial containing:

1 mg of the construct of formula IV, based on peptide weight net of acetate
1.181 mg succinic acid, NF
47.0 mg mannitol, USP
1N NaOH, USP, as needed to adjust pH
1N HCl, USP, as needed to adjust pH
Water for injection, to 1 mL volume The pH of the final product was adjusted to pH 5.75±0.05 with 1N NAOH or 1N HCl, as required. The resulting solution was filtered through a sterile 0.22 micron filter prior to vialing, and was stored at 5° C. until used.

An alternative formulation of the construct of formula IV was made for pharmaceutical use, similar to the formulation above, but additionally including between about 0.02 mg and 0.06 mg of disodium pamoate, such that the resulting solution was a pamoate suspension.

EXAMPLE 3

In a human clinical trial of a subcutaneously administered formulation in which the construct of formula IV was the active pharmaceutical ingredient, the half life of the construct of formula IV was determined to be approximately 3 hours. The construct of formula IV lead to a mean peak increase in plasma cGMP concentration of 1.7 ng/mL at a dose of 0.3 µg/kg of the construct of formula IV as a single, subcutaneous injection.

Cyclic guanosine monophosphate (cGMP) in the plasma samples was extracted using a protein precipitation method. cGMP and internal standard, cyclic adenosine monophosphate (cAMP), were separated using a HPLC technique and detected by an Applied Biosystems API-4000 liquid chromatography-tandem mass spectrometer (LC-MS/MS) with turbo-ion spray ionization (electrospray) in positive ion mode. Positive ions were detected in multiple reaction moni- (SEQ ID NO: 3)

Hept-Cys-His-Phe-D-Ala-Gly-Arg-D-Nle-Asp-Arg-Ile-Ser-Cys-Tyr—[piperazinone-NH$_2$]

The resulting construct had formula of $C_{82}H_{127}N_{27}O_{20}S_2$ as the anhydrous, counter-ion free peptide and a molecular weight of 1875.22, determined as the average mass of the anhydrous, counter-ion free peptide. In the solid state form, the construct is a white to off-white solid with acetate as the associated counter-ion. The specific rotation of the construct as a 1.0% solution in water at 25° C. was found, after correction for construct content, to be:

$[\alpha]_D^{25} = -26.9°$.

toring (MRM) mode with Precursor→Product ion pairs of 346.3→152.1 for cGMP, and 330.0→136.3 for cAMP.

EXAMPLE 4

Natriuretic peptide receptor binding affinity (expressed as $K_i$) of the construct of formula IV (0.01 nM-1 µM) was evaluated using 3 human embryonic kidney (HEK) cell lines expressing recombinant human, dog, or rat NPRA. The $K_i$ values of the construct of formula IV for human, dog, and rat NPRA were 1, 41, and 10 nM, respectively (Table 1).

TABLE 1

Comparison of Affinity ($K_i$) and Functional Potency (cGMP Generation; $EC_{50}$ and $E_{max}$) of the Construct of Formula IV for Human, Dog and Rat NPRA (Expressed in HEK Cell Lines). Results are given as Mean ± Standard Deviation.

| | Binding | | Function (cGMP) | | |
|---|---|---|---|---|---|
| Receptor | Ki (nM) | n | $EC_{50}$ (nM) | $E_{max}$ (% of ANP response) | n |
| Human NPR-A | 1 ± 1 | 45 | 2 ± 4 | 94 ± 8 | 51 |
| Dog NPR-A | 41 ± 26 | 6 | 3 ± 1 | 94 ± 11 | 5 |
| Rat NPR-A | 10 ± 3 | 4 | 14 ± 9 | 98 ± 7 | 47 |

As shown in Table 2, selectivity of the construct of formula IV for NPRA versus the other natriuretic peptide receptors, NPRB and NPRC, were determined in in binding studies in HEK cell lines. The construct of formula IV had a $K_i$ of 7±1 nM (n=4) for human NPRC, which is believed to be primarily a clearance receptor, and which is approximately a 7-fold lower affinity than for NPRA. The construct of formula IV was without effect (in concentrations up to 10 μM) in NPRB functional assays (cGMP generation; n=8).

TABLE 2

Comparison of Affinities ($K_i$) and Functional Potencies (cGMP Generation; $EC_{50}$ and Emax) of the construct of formula IV, hANP (human ANP) and hBNP (human BNP) for hNPRA (human NPRA), hNPRB (human NPRB) and hNPRC (human NPRC) (expressed in HEK cell lines). Results are given as Mean ± Standard Deviation.

| | hNPR-A | | | | | hNPR-B | | | hNPR-C | |
|---|---|---|---|---|---|---|---|---|---|---|
| | Binding | | Function (cGMP) | | | Function (cGMP) | | | Binding | |
| Compound | Ki (nM) | n | $EC_{50}$ (nM) | $E_{max}$ (%) | n | $EC_{50}$ (nM) | $E_{max}$ (%) | n | Ki (nM) | n |
| Construct of Formula IV | 1 ± 1 | 45 | 2 ± 4 | 94 ± 8 | 51 | Not calculable | 1 ± 1 | 8 | 7 ± 1 | 4 |
| hANP | 0.05 ± 0.2 | 6 | 0.4 ± 0.6 | 97 ± 14 | 54 | Not calculable | 6 ± 2 | 5 | 0.05 ± 0.06 | 5 |
| hBNP | 3 ± 2 | 4 | 2 ± 2 | 96 ± 5 | 11 | Not calculable | 9 ± 3 | 7 | 0.7 | 2 |

The natural natriuretic peptides, hANP and hBNP, have equivalent or higher affinity, respectively, for NPRC than NPRA, as compared to the construct of formula IV, which is 7-fold lower.

EXAMPLE 5

Endogenous natriuric peptides, such as hANP, hBNP and hCNP, are rapidly degraded by neutral endopeptidase (NEP). The reported human plasma half-life for hANP, hBNP and hCNP is about 2 minutes, 20 minutes and 2 minutes, respectively (Potter, L. R., Yoder, A. R., Flora, D. R., et al. "Natriuretic peptides: their structures, receptors, physiologic functions and therapeutic applications." *Handbook Exp. Pharmacol.* 191:341-366 (2009)). A comparison was made between the sensitivity of the construct of formula IV and ANP to metabolism by human NEP (hNEP) (substrate concentration 50 μM). After 2-hour exposure to hNEP solution at 37° C., there was minimal degradation of the construct of formula IV (92% remaining; n=5). In contrast, under these conditions ANP was about 90% degraded after 60 minutes and 100% after 2-hours (n=4). Similarly, for CNP there was 39% remaining after 60-min incubation with hNEP, and 1% after 2-hours (n=1). Results are shown in FIG. 1; results in FIG. 1 are expressed as the percent of the starting material, and are either the mean of 1-5 experiments or, where error bars are shown, are the mean±standard deviation.

EXAMPLE 6

Figure 2:
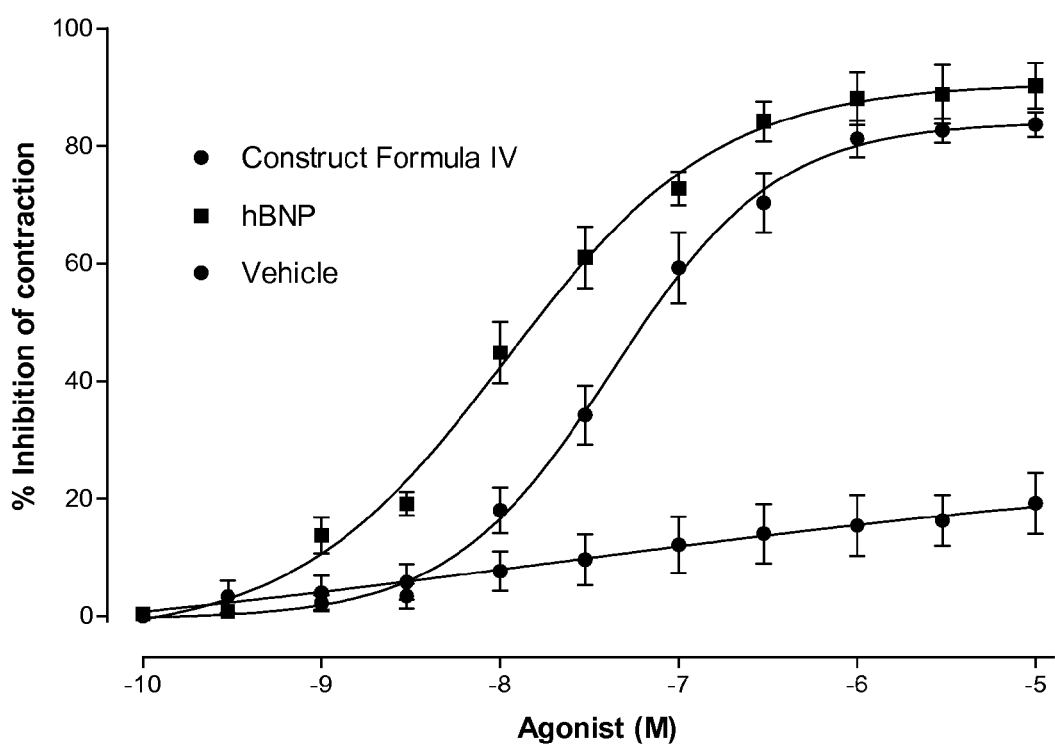
FIG. 2 is a plot of the percent inhibition of contraction of guinea pig trachea precontracted with the muscarinic receptor agonist, carbachol, in response to varying concentrations of the construct of formula IV, hBNP and vehicle control.

The construct of formula IV (0.1 nM-10 μM) produced a concentration-dependent relaxation of guinea pig trachea precontracted with the muscarinic receptor agonist, carbachol, with an $IC_{50}$ of 42.7 nM (n=3). The maximum relaxation elicited by the construct of formula IV was 83.6% of that produced by the positive control, beta2 receptor agonist, salbutamol, as shown in FIG. 2. hBNP (0.1 nM-10 μM) also produced a concentration-dependent relaxation of precontracted guinea pig trachea, with an $IC_{50}$ of 10.7 nM, and a maximum relaxation that was 90.3% of that produced by salbutamol (n=3), as shown in FIG. 2. The potency difference between BNP and the construct of formula IV in this assay (hBNP is about 4-fold more potent) is similar to the differences in binding affinities (hBNP has about 5-fold higher potency) in guinea pig lung preparations. Results in FIG. 2 are expressed as mean±SEM; n=3.

EXAMPLE 7

Male Wistar rats weighing 250±20 g were used. The animals were sacrificed by $CO_2$ overexposure and 3 tracheal rings are isolated from each animal. The tracheal ring tissue was placed under 1 g tension in a 10 mL bath containing Krebs solution pH 7.4 and indomethacin (2.8 μM) at 37° C. and submaximal tonic contraction was induced by 1 μM carbachol after a 45 minute equilibration period. Relaxation in tracheal rings pre-contracted with carbachol (set as 100% control response) was tested with the construct of formula IV in varying concentrations to determine inhibition of contraction. At a concentration of 0.1 μM, the construct of formula IV resulted in inhibition of contraction (relaxation) of 6%, at a concentration of the construct of formula IV of 1 μM resulted in inhibition of contraction (relaxation) of 10%, and at a concentration of the construct of formula IV of 10 μM resulted in inhibition of contraction (relaxation) of 19% (all percentage values are an average of triplicates).

EXAMPLE 8

Figure 3:
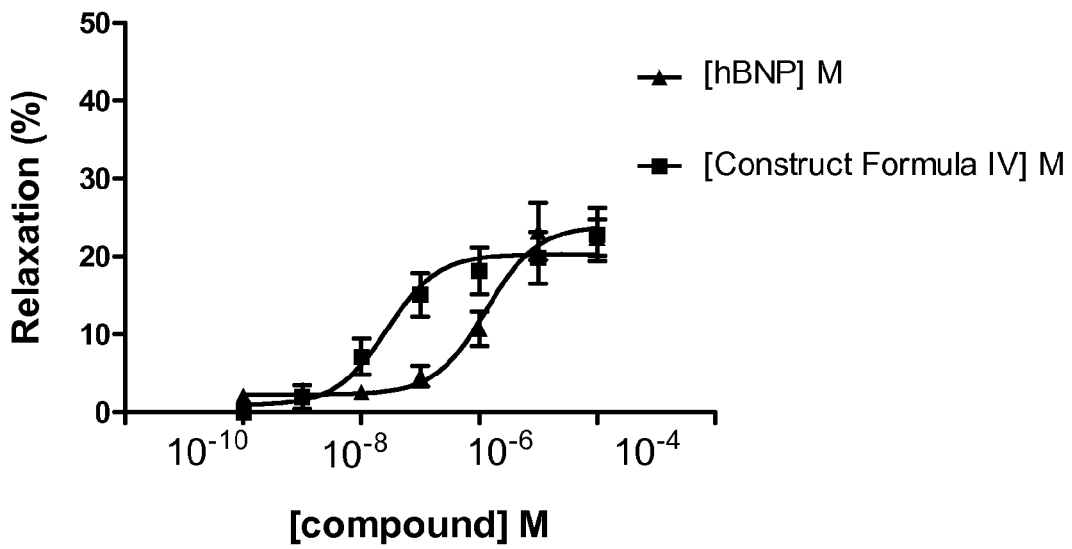
FIG. 3 is a plot of percent relaxation of human lung tissues precontracted with carbachol in response to varying concentrations of the construct of formula IV and hBNP.

The relaxant effects of the construct of formula IV were examined in a novel human precision-cut lung slice preparation method (Cooper, P. R. and Panettieri, R. A. "Steroids completely reverse albuterol-induced $\beta_2$-adrenergic receptor tolerance in human small airways." *J Allergy Clin Immunol.* 2008; 122:734-740 (2009)). Assessment in tissues from 4 human lungs demonstrated that the construct of formula IV (0.1 nM-100 µM) produced a potent, concentration-dependent but small relaxation of tissues precontracted with carbachol (1 µM), as shown in FIG. 3). The $IC_{50}$ (of the maximum relaxation induced by the construct of formula IV) for the construct of formula IV was 32 nM and the maximum relaxation, obtained at 1 µM, was 22% of the contractile response to carbachol. hBNP (0.1 nM-100 µM) also relaxed precontracted human lung preparations with an $IC_{50}$ of 1.3 µM, and a maximal relaxation 23% of the carbachol-induced contractile response (n=2). Thus, the construct of formula IV is 30-fold more potent and as effective as the natural ligand, hBNP, in relaxing this in vitro human lung preparation. Isoprenaline (100 µM), the full beta$_2$-receptor agonist, produced about 75% relaxation of carbachol-induced contraction. FIG. 3 depicts comparison of the relaxant effects of the construct of formula IV and hBNP in human lung slice preparations contracted with carbachol. The results are the Mean±SEM from at least 4 sections from 4 (construct of formula IV) or 2 (hBNP) separate lungs.

EXAMPLE 9

Figure 4A:
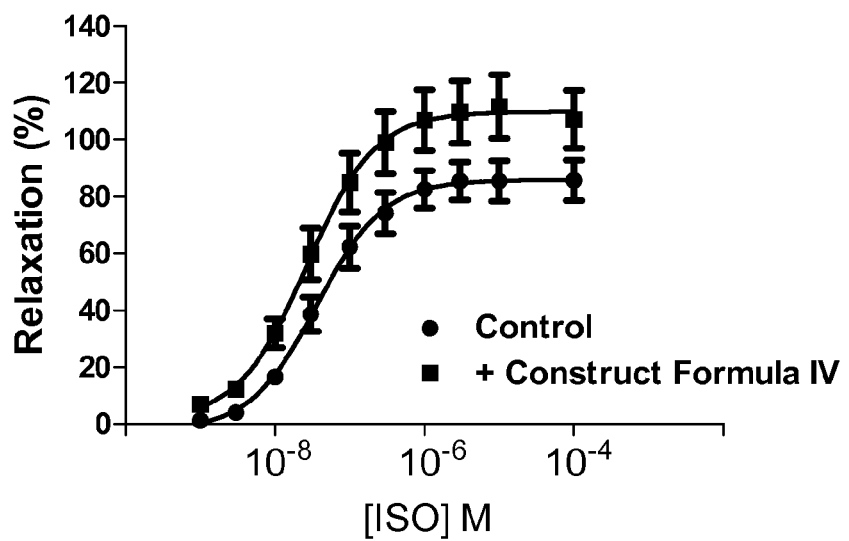
FIGS. 4A and 4B are plots of percent relaxation of human lung tissues precontracted with carbachol and treated with isoproterenol and the construct of formula IV (FIG. 4A) or isoproterenol and hBNP (FIG. 4B).
Figure 4B:
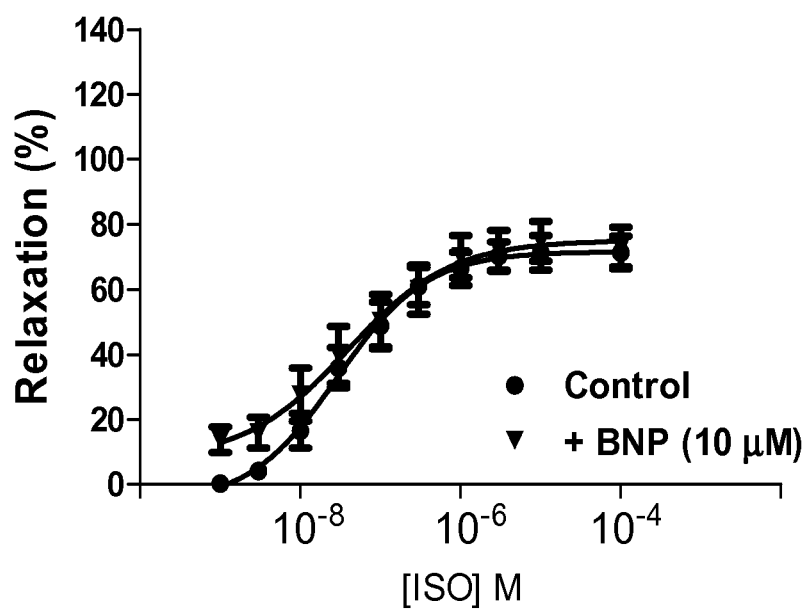
Figure 5:
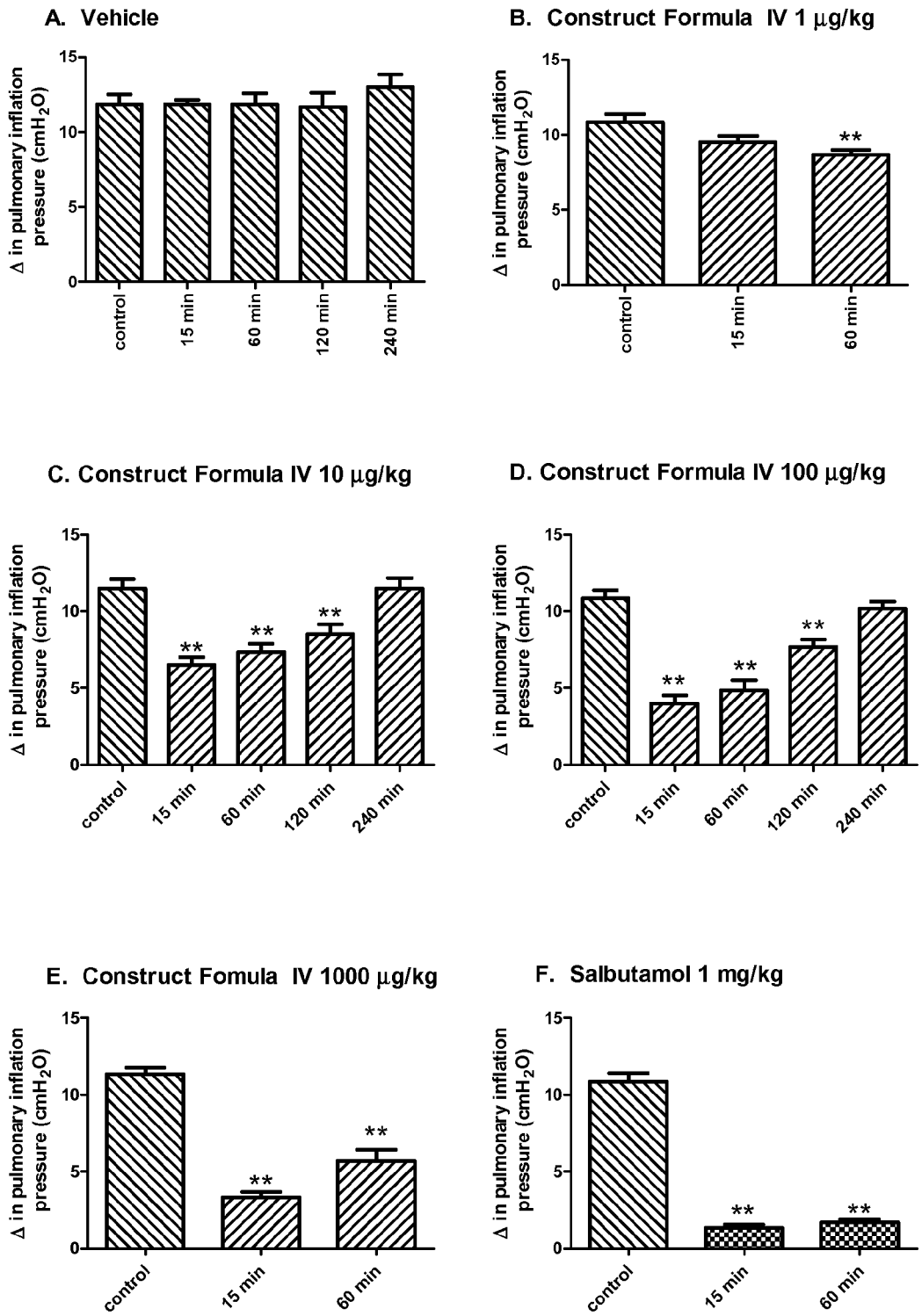
FIGS. 5A through 5F are column bar graphs of changes in pulmonary inflation pressure (cm H$_2$O) in guinea pigs administered the muscarinic receptor agonist methacholine with intratracheal delivery of vehicle (FIG. 5A), varying concentrations of the construct of formula IV (FIGS. 5B through 5E; 1, 10, 100 and 1000 μg/kg), and salbutamol (FIG. 5F; 1000 μg/kg).

Using the methods of Example 8, it was found that the construct of formula IV (10 µM; n=4) potentiated the relaxant effects of isoproterenol in human lung preparations precontacted with carbachol, whereas hBNP (10 µM; n=3) had no such effect, as shown in FIG. 4A and FIG. 4B. FIG. 4A shows the effect of the construct of formula IV on human lung preparations precontacted with carbachol, while FIG. 4B shows the effect of hBMP on human lung preparations pre-contacted with carbachol. Isoproterenol-mediated bronchodilatation was 88.2±3.4% in the absence of the construct of formula IV (10 µM) and 108.5±5.0% in its presence (n=4; P=0.04).

EXAMPLE 10

Studies were conducted with intratracheal (IT) delivery of the construct of formula IV in anesthetized guinea pigs (Dunkin Hartley) challenged with the muscarinic receptor agonist, methacholine. The construct of formula IV (1-1000 µg/kg, IT, n=6) produced a dose-dependent inhibition of the bronchoconstrictor response evoked by aerosol challenge with methacholine (10 µg/mL) challenge, as shown in FIG. 5A through FIG. 5F. For doses of 10, 100 and 1000 µg/kg (FIGS. 5C, 5D and 5C, respectively) a significant (P<0.05) maximum inhibition of 43±4%, 63±5% and 70±3%, respectively, was observed after 15 minutes pretreatment with construct of formula IV. The inhibition was maintained for all doses after the 60 minute pretreatment time. The duration of action of 10 µg/kg and 100 µg/kg doses of the construct of formula IV was explored (FIGS. 4C and 4D). For both doses the inhibition extended to 120 minutes post-administration, although it was reduced, with inhibitory effect absent after 240 minutes pretreatment. Administration of the positive control beta$_2$-receptor agonist, salbutamol (1000 µg/kg, IT, n=6) significantly inhibited (by 87%) the bronchoconstrictor response evoked by methacholine (10 µg/mL) challenge, reaching a maximum inhibition of 87±2% after 15 minutes (FIG. 4F).

EXAMPLE 11

A patient with an acute asthma attack or COPD is administered a formulation including the construct of formula IV, including a formulation such as described in Example 2, by means of subcutaneous injection.

EXAMPLE 12

A patient with an acute asthma attack or COPD is administered a formulation including the construct of formula IV, including a formulation such as described in Example 2, by means of inhalation of a nebulized solution.

EXAMPLE 13

A patient with an an acute asthma attack or COPD is administered a formulation including the construct of formula IV by means of a drug powder inhaler.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above and/or in the attachments, and of the corresponding application(s), are hereby incorporated by reference.

What is claimed is:

1. A method of treatment of acute asthma or chronic obstructive pulmonary disease (COPD), comprising administering to a patient in need of such treatment a pharmaceutically effective amount of a composition comprising the construct of formula IV:

(IV)

Hept-Cys-His-Phe-D-Ala-Gly-Arg-D-Nle-Asp-Arg-Ile-Ser-Cys-Tyr

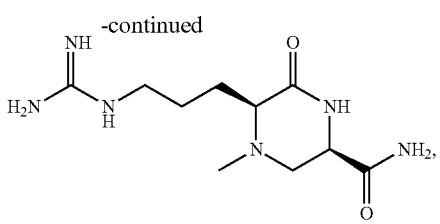

or a pharmaceutically acceptable salt of the construct of formula IV.

2. The method of claim 1 wherein the method is a method of treatment of acute asthma.

3. The method of claim 1 wherein the method is a method of treatment of COPD.

4. The method of claim 1 wherein administering to the patient comprises airway administration of a nebulized or dry powder composition.

5. The method of claim 1 wherein administering to the patient comprises airway administration.

6. A method of treatment of acute asthma or COPD, comprising the steps of diagnosing a patient with acute asthma or COPD;

administering to the patient diagnosed with acute asthma or COPD a pharmaceutically effective amount of a composition comprising the construct of formula IV:

(IV)

Hept-Cys-His-Phe-D-Ala-Gly-Arg-D-Nle-Asp-Arg-Ile-Ser-Cys-Tyr or a pharmaceutically acceptable salt of the construct of formula IV.

7. The method of claim 6 wherein the patient is diagnosed with acute asthma.

8. The method of claim 6 wherein the patient is diagnosed with COPD.

9. The method of claim 6 wherein administering to the patient comprises airway administration of a nebulized or dry powder composition.

10. The method of claim 6 wherein administering to the patient comprises airway administration.

\* \* \* \* \*